(12) United States Patent
Williams et al.

(10) Patent No.: US 12,005,186 B2
(45) Date of Patent: Jun. 11, 2024

(54) CLOSED LOOP OXYGEN CONTROL

(71) Applicant: FISHER & PAYKEL HEALTHCARE LIMITED, Auckland (NZ)

(72) Inventors: Rhys Matthew James Williams, Auckland (NZ); Russel William Burgess, Auckland (NZ); David Martin Russell, Auckland (NZ); Anton Kim Gulley, Auckland (NZ); Charles Grady Cantrell, Auckland (NZ); Yi Lin Huang, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 148 days.

(21) Appl. No.: 16/753,947

(22) PCT Filed: Oct. 5, 2018

(86) PCT No.: PCT/NZ2018/050137
§ 371 (c)(1),
(2) Date: Apr. 6, 2020

(87) PCT Pub. No.: WO2019/070136
PCT Pub. Date: Apr. 11, 2019

(65) Prior Publication Data
US 2021/0361899 A1 Nov. 25, 2021

Related U.S. Application Data

(60) Provisional application No. 62/596,722, filed on Dec. 8, 2017, provisional application No. 62/569,429, filed on Oct. 6, 2017.

(51) Int. Cl.
*A61M 16/00* (2006.01)
*A61M 16/06* (2006.01)
(Continued)

(52) U.S. Cl.
CPC .... *A61M 16/0003* (2014.02); *A61M 16/0051* (2013.01); *A61M 16/0066* (2013.01);
(Continued)

(58) Field of Classification Search
CPC .............. A61M 16/00; A61M 16/0003; A61M 16/0051; A61M 16/0066; A61M 16/022;
(Continued)

(56) References Cited

U.S. PATENT DOCUMENTS

| 4,326,513 A | 4/1982 | Schulz et al. |
| 5,365,922 A * | 11/1994 | Raemer ................. A61B 5/097 |
| | | 128/204.23 |

(Continued)

FOREIGN PATENT DOCUMENTS

| EP | 2474334 A1 | 7/2012 |
| EP | 2682147 A2 | 1/2014 |

(Continued)

OTHER PUBLICATIONS

International Search Report and Written Opinion od rhe International Searchinf Authority for International Application No. PCT/NZ2018/050137, dated Jan. 25, 2019, in 25 pages.

*Primary Examiner* — Joseph D. Boecker
(74) *Attorney, Agent, or Firm* — Knobbe, Martens, Olson & Bear, LLP

(57) ABSTRACT

The present disclosure provides for a flow therapy apparatus that can implement one or more closed loop control systems to control the flow of gases of a flow therapy apparatus. The flow therapy apparatus can monitor blood oxygen saturation (SpO2) of a patient and control the fraction of oxygen delivered to the patient (FdO2). The flow therapy apparatus can automatically adjust the FdO2 in order to achieve a targeted SpO2 value for the patient.

17 Claims, 32 Drawing Sheets

(51) Int. Cl.
*A61M 16/08* (2006.01)
*A61M 16/10* (2006.01)
*A61M 16/12* (2006.01)
*A61M 16/16* (2006.01)
*A61M 16/20* (2006.01)

(52) U.S. Cl.
CPC ...... *A61M 16/026* (2017.08); *A61M 16/0672* (2014.02); *A61M 16/0816* (2013.01); *A61M 16/105* (2013.01); *A61M 16/125* (2014.02); *A61M 16/161* (2014.02); *A61M 16/201* (2014.02); *A61M 2016/003* (2013.01); *A61M 2016/1025* (2013.01); *A61M 2205/3375* (2013.01); *A61M 2205/583* (2013.01); *A61M 2230/005* (2013.01); *A61M 2230/06* (2013.01); *A61M 2230/205* (2013.01); *A61M 2230/42* (2013.01); *A61M 2230/435* (2013.01)

(58) Field of Classification Search
CPC ............ A61M 16/024; A61M 16/0666; A61M 16/0672; A61M 16/107; A61M 16/12; A61M 16/122; A61M 16/125; A61M 16/202; A61M 16/203; A61M 2016/0033; A61M 2016/1005; A61M 2016/102; A61M 2016/1025; A61M 2205/3375; A61M 2230/205; A61M 2230/435; A61B 5/0833

See application file for complete search history.

(56) References Cited

U.S. PATENT DOCUMENTS

| | | | |
|---|---|---|---|
| 5,706,801 A * | 1/1998 | Remes | A61M 16/0672 128/204.22 |
| 6,142,149 A | 11/2000 | Steen | |
| 6,512,938 B2 | 1/2003 | Claure et al. | |
| 6,644,312 B2 | 11/2003 | Berthon-Jones et al. | |
| 6,671,529 B2 | 12/2003 | Claure et al. | |
| 6,761,165 B2 | 7/2004 | Strickland, Jr. | |
| 6,796,305 B1 | 9/2004 | Banner et al. | |
| 6,845,773 B2 | 1/2005 | Berthon-Jones et al. | |
| 6,954,702 B2 | 10/2005 | Pierry et al. | |
| 7,008,380 B1 | 3/2006 | Rees et al. | |
| 7,066,173 B2 | 6/2006 | Banner et al. | |
| 7,089,937 B2 | 8/2006 | Berthon-Jones et al. | |
| 7,183,552 B2 | 2/2007 | Russell | |
| 7,210,478 B2 | 5/2007 | Russell | |
| 7,222,624 B2 | 5/2007 | Rashad et al. | |
| 7,415,297 B2 | 8/2008 | Al-Ali et al. | |
| 7,432,508 B2 | 10/2008 | Daniels et al. | |
| 7,527,054 B2 | 5/2009 | Misholi | |
| 7,606,668 B2 | 10/2009 | Pierry et al. | |
| 7,684,931 B2 | 3/2010 | Pierry et al. | |
| 7,802,571 B2 | 9/2010 | Tehrani | |
| 8,066,647 B2 | 11/2011 | Armitstead | |
| 8,080,798 B2 | 12/2011 | Russell | |
| 8,122,883 B2 | 2/2012 | Banner et al. | |
| 8,186,346 B2 | 5/2012 | Knight et al. | |
| 8,221,319 B2 | 7/2012 | Lovejoy | |
| 8,333,194 B2 | 12/2012 | Lewis et al. | |
| 8,333,199 B2 | 12/2012 | Landis et al. | |
| 8,397,725 B2 | 3/2013 | Slaker et al. | |
| 8,509,869 B2 | 8/2013 | Baker, Jr. et al. | |
| 8,522,782 B2 | 9/2013 | Lewis et al. | |
| 8,528,552 B2 | 9/2013 | Von Blumenthal | |
| 8,544,467 B2 | 10/2013 | Berthon-Jones et al. | |
| 8,585,607 B2 | 11/2013 | Klap et al. | |
| 8,640,699 B2 | 2/2014 | Baker, Jr. et al. | |
| 8,640,700 B2 | 2/2014 | Baker, Jr. et al. | |
| 8,667,963 B2 | 3/2014 | Sherman et al. | |
| 8,670,811 B2 | 3/2014 | O'Reilly | |
| 8,676,285 B2 | 3/2014 | Doyle et al. | |
| 8,689,788 B2 | 4/2014 | Rabi | |
| 8,721,542 B2 | 5/2014 | Al-Ali et al. | |
| 8,734,360 B2 | 5/2014 | Klap et al. | |
| 8,770,192 B2 | 7/2014 | Tham | |
| 8,789,530 B2 | 7/2014 | Amjad et al. | |
| 8,821,418 B2 | 9/2014 | Meger et al. | |
| 8,852,094 B2 | 10/2014 | Al-Ali et al. | |
| 8,882,684 B2 | 11/2014 | Halperin et al. | |
| 8,998,830 B2 | 4/2015 | Halperin et al. | |
| 9,022,034 B2 | 5/2015 | Slaker et al. | |
| 9,089,657 B2 | 7/2015 | Kimm et al. | |
| 9,220,856 B2 | 12/2015 | Martin et al. | |
| 9,233,218 B2 | 1/2016 | Chapman et al. | |
| 9,254,368 B2 | 2/2016 | Von Blumenthal et al. | |
| 9,364,623 B2 | 6/2016 | Lellouche et al. | |
| 9,381,317 B2 | 7/2016 | Landis et al. | |
| 9,427,547 B2 | 8/2016 | Landis et al. | |
| 9,440,038 B2 | 9/2016 | Berthon-Jones et al. | |
| 9,449,493 B2 | 9/2016 | Shinar et al. | |
| 9,554,740 B2 | 1/2017 | Saeed et al. | |
| 9,636,056 B2 | 5/2017 | Al-Ali et al. | |
| 9,649,333 B2 | 5/2017 | Rabi | |
| 9,750,463 B2 | 9/2017 | Swamy et al. | |
| 9,883,809 B2 | 2/2018 | Klap et al. | |
| 10,098,591 B2 | 2/2018 | Klap et al. | |
| 10,238,351 B2 | 3/2019 | Halperin et al. | |
| 10,251,585 B2 | 4/2019 | Al-Ali et al. | |
| 10,292,625 B2 | 5/2019 | Shinar et al. | |
| 10,398,870 B2 | 9/2019 | Chapman et al. | |
| 2001/0029340 A1 * | 10/2001 | Mault | A61B 5/0833 600/531 |
| 2004/0186391 A1 | 9/2004 | Pierry et al. | |
| 2005/0098527 A1 | 5/2005 | Yates, III | |
| 2006/0011199 A1 | 1/2006 | Rashad et al. | |
| 2006/0052950 A1 | 3/2006 | Pierry et al. | |
| 2006/0102581 A1 | 5/2006 | Yates, III | |
| 2006/0108363 A1 | 5/2006 | Yates, III | |
| 2006/0237015 A1 | 10/2006 | Berthon-Jones et al. | |
| 2007/0000494 A1 | 1/2007 | Banner et al. | |
| 2008/0000866 A1 | 1/2008 | Yates, III | |
| 2008/0058667 A1 | 3/2008 | Pierry et al. | |
| 2008/0066752 A1 | 3/2008 | Baker et al. | |
| 2008/0076986 A1 | 3/2008 | Pav | |
| 2008/0114223 A1 | 5/2008 | Pierry et al. | |
| 2008/0275349 A1 | 11/2008 | Halperin et al. | |
| 2009/0227852 A1 | 9/2009 | Glaser | |
| 2009/0320836 A1 * | 12/2009 | Baker, Jr. | A61M 16/12 128/203.14 |
| 2010/0137729 A1 | 6/2010 | Pierry et al. | |
| 2011/0041849 A1 * | 2/2011 | Chen | A61M 16/026 128/204.23 |
| 2011/0290252 A1 | 12/2011 | Amjad et al. | |
| 2012/0088992 A1 | 4/2012 | Armitstead | |
| 2012/0090611 A1 | 4/2012 | Graboi et al. | |
| 2012/0132211 A1 | 5/2012 | Halperin et al. | |
| 2012/0253142 A1 | 10/2012 | Meger et al. | |
| 2013/0152933 A1 | 6/2013 | Lischer et al. | |
| 2013/0239961 A1 | 9/2013 | Ross, Jr. et al. | |
| 2013/0245973 A1 | 9/2013 | Ross, Jr. et al. | |
| 2013/0312754 A1 | 11/2013 | Garde et al. | |
| 2013/0340752 A1 | 12/2013 | Landis et al. | |
| 2014/0202455 A1 | 7/2014 | Garde et al. | |
| 2014/0275901 A1 * | 9/2014 | Flanagan | G16H 20/00 600/364 |
| 2014/0318536 A1 | 10/2014 | Landis et al. | |
| 2015/0018648 A1 | 1/2015 | Boyer et al. | |
| 2015/0059745 A1 * | 3/2015 | Barker | A61M 16/0051 128/203.14 |
| 2015/0087936 A1 | 3/2015 | Al-Ali et al. | |
| 2015/0174359 A1 | 6/2015 | Elliot et al. | |
| 2015/0208968 A1 | 7/2015 | Ennett et al. | |
| 2015/0335850 A1 | 11/2015 | Santhana Naidu et al. | |
| 2016/0022952 A1 * | 1/2016 | Brown | A61M 16/204 128/204.22 |
| 2016/0067433 A1 | 3/2016 | Martin et al. | |
| 2016/0082220 A1 * | 3/2016 | Barker | B01F 23/10 128/203.12 |
| 2016/0121070 A1 | 5/2016 | Chapman et al. | |
| 2016/0296721 A1 | 10/2016 | Landis et al. | |
| 2016/0303405 A1 | 10/2016 | Elliot et al. | |

(56) References Cited

U.S. PATENT DOCUMENTS

| | | | |
|---|---|---|---|
| 2016/0367776 A1 | 12/2016 | Landis et al. |
| 2016/0367779 A1 | 12/2016 | Landis et al. |
| 2017/0224943 A1 | 8/2017 | Creusot et al. |
| 2017/0232221 A1 | 8/2017 | Kepler et al. |
| 2018/0001042 A1 | 1/2018 | Albanese et al. |
| 2018/0099109 A1 | 4/2018 | Kinsky et al. |
| 2018/0125430 A1 | 5/2018 | Al-Ali et al. |
| 2018/0206795 A1 | 7/2018 | Al-Ali |
| 2018/0220897 A1 | 8/2018 | Meger et al. |
| 2018/0280645 A1 | 10/2018 | Lellouche et al. |
| 2018/0353718 A1 | 12/2018 | Gale et al. |
| 2019/0029578 A1 | 1/2019 | Al-Ali et al. |
| 2019/0150789 A1 | 3/2019 | Lynn |
| 2019/0254570 A1 | 8/2019 | Shinar et al. |
| 2019/0320987 A1 | 10/2019 | Halperin et al. |
| 2020/0060628 A1 | 2/2020 | Al-Ali et al. |
| 2021/0187222 A1* | 6/2021 | Dickens ............. A61M 16/101 |
| 2023/0022107 A1 | 1/2023 | Gulley et al. |

FOREIGN PATENT DOCUMENTS

| | | |
|---|---|---|
| EP | 2575617 B1 | 6/2019 |
| WO | WO 2010/101778 A1 | 9/2010 |
| WO | WO 2010/101812 A2 | 9/2010 |
| WO | WO 2017/079798 A1 | 5/2017 |
| WO | WO 2018/201078 A1 | 11/2018 |
| WO | WO 2019/070136 A1 | 4/2019 |
| WO | WO 2019/089655 A1 | 5/2019 |
| WO | WO 2019/102384 A1 | 5/2019 |
| WO | WO 2021/079202 A1 | 4/2021 |

* cited by examiner

CLOSED LOOP OXYGEN CONTROL

FIELD OF THE DISCLOSURE

The present disclosure relates to methods and systems for controlling oxygen delivery in a flow therapy apparatus.

BACKGROUND

Respiratory apparatuses are used in various environments such as hospital, medical facility, residential care, or home environments to deliver a flow of gas to users or patients. A respiratory apparatus, or a flow therapy apparatus, may include an oxygen inlet to allow delivery of supplemental oxygen with the flow of gas, and/or a humidification apparatus to deliver heated and humidified gases. A flow therapy apparatus may allow adjustment and control over characteristics of the gases flow, including flow rate, temperature, gas concentration, such as oxygen concentration, humidity, pressure, etc.

SUMMARY

In accordance with certain features, aspects and advantages of a first embodiment disclosed herein, a respiratory apparatus that provides a flow of gases to a patient, the respiratory apparatus comprising: a controller configured to control delivery of gases to the patient using closed loop control, wherein the controller is configured to: receive patient parameter data indicative of oxygen saturation (SpO2) of the patient from at least one sensor; execute a control phase, wherein operation of the respiratory apparatus during a therapy session is based at least in part on the patient parameter data; and a gases composition sensor configured to determine at least oxygen content (FdO2) of gases flow during operation of the respiratory apparatus, wherein the gases composition sensor is an ultrasonic sensor system.

In some configurations of the first embodiment, the respiratory apparatus comprises a patient interface selected from at least one of: a face mask, a nasal mask, a nasal pillows mask, a tracheostomy interface, a nasal cannula, or an endotracheal tube.

In some configurations of the first embodiment, the nasal cannula is a non-sealed nasal cannula.

In some configurations of the first embodiment, the respiratory apparatus is configured to deliver a nasal high flow (NHF) flow of gases to the patient.

In some configurations of the first embodiment, the at least one sensor is a pulse oximeter.

In some configurations of the first embodiment, the controller is configured to receive device parameter data indicative of an oxygen concentration of the gases flow.

In some configurations of the first embodiment, the respiratory apparatus comprises a supplementary gas inlet valve.

In some configurations of the first embodiment, the controller is configured to control operation of the supplementary gas inlet valve.

In some configurations of the first embodiment, the supplementary gas inlet valve is a proportional valve.

In some configurations of the first embodiment, the supplementary gas inlet valve is an oxygen inlet valve.

In some configurations of the first embodiment, the supplementary gas inlet valve comprises a swivel connector.

In some configurations of the first embodiment, the respiratory apparatus comprises an ambient air inlet.

In some configurations of the first embodiment, the oxygen inlet valve is in fluid communication with a filter module and the respiratory apparatus is configured to entrain oxygen received from the oxygen inlet valve with ambient air from the ambient air inlet in the filter module.

In some configurations of the first embodiment, the gases composition sensor is positioned downstream of a blower module of the respiratory apparatus.

In some configurations of the first embodiment, the filter module is positioned upstream of the blower module of the respiratory apparatus.

In some configurations of the first embodiment, the blower module mixes ambient air and oxygen.

In some configurations of the first embodiment, the closed loop control includes using a first closed loop control model configured to determine a target fraction of delivered oxygen (FdO2).

In some configurations of the first embodiment, the target FdO2 is determined based at least in part on a target SpO2 and measured SpO2.

In some configurations of the first embodiment, the target FdO2 is further based at least in part on measured FdO2.

In some configurations of the first embodiment, the target FdO2 is further based at least in part on a previous target FdO2.

In some configurations of the first embodiment, the closed loop control includes using a second closed loop control model configured to determine a control signal for an oxygen inlet valve based at least in part on a difference between the target FdO2 and the measured FdO2.

In some configurations of the first embodiment, the control signal for the oxygen valve is determined based at least in part on the target FdO2 and the measured FdO2.

In some configurations of the first embodiment, the control signal for the oxygen valve is determined further based at least in part on a gases flow rate.

In some configurations of the first embodiment, the gases flow rate is the total gases flow rate.

In some configurations of the first embodiment, the controller is configured to transfer to a manual mode of operation when a signal quality of the at least one sensor is below a threshold.

In some configurations of the first embodiment, the controller is configured to generate a notification for a user indicating that signal quality of the at least one sensor is below a threshold.

In some configurations of the first embodiment, the notification requests input from the user indication whether to transfer to a manual mode of operation.

In some configurations of the first embodiment, the controller is configured to transfer to a manual mode of operation when the patient SpO2 is outside of defined limits.

In some configurations of the first embodiment, the controller is configured to trigger an alarm when the patient SpO2 is outside of the defined limits.

In some configurations of the first embodiment, control of the delivery of gases includes control of FdO2 of the gases flow, and the controller is configured to receive an indication of signal quality of the at least one sensor, and apply a weighting to the control of the FdO2 based at least in part on the signal quality.

In some configurations of the first embodiment, the indication of signal quality corresponds to specific SpO2 readings.

In some configurations of the first embodiment, the control phase is configured to be executed using a patient specific model In some configurations of the first embodiment, the patient specific model is generated during a learning phase of the therapy session.

In some configurations of the first embodiment, the patient specific model is generated during the therapy session.

In some configurations of the first embodiment, the patient specific model is updated during the therapy session.

In some configurations of the first embodiment, the control phase is configured to be executed using a PID control based at least in part on the patient specific model.

In some configurations of the first embodiment, the patient specific model includes an oxygen efficiency of the patient.

In some configurations of the first embodiment, the oxygen efficiency is determined based at least in part on measured SpO2 and measured FdO2.

In some configurations of the first embodiment, the oxygen efficiency is determined based at least in part on measured SpO2 divided by measured FdO2.

In some configurations of the first embodiment, the oxygen efficiency is determined based at least in part on a non-linear relationship between measured SpO2 of the patient and measured FdO2.

In some configurations of the first embodiment, the controller is configured to predict the SpO2 of the patient based at least in part on the measured FdO2.

In some configurations of the first embodiment, previous predictions of the SpO2 are compared with measured SpO2 to calculate model error.

In some configurations of the first embodiment, the model error is weighted by signal quality of the at least one sensor.

In some configurations of the first embodiment, the model error is used to correct the current SpO2 prediction.

In some configurations of the first embodiment, the predicted SpO2 is based at least in part on a Smith predictor.

In some configurations of the first embodiment, the controller is configured to receive input identifying characteristics of the patient.

In some configurations of the first embodiment, the patient characteristics include at least one of a patient type, age, weight, height, or gender.

In some configurations of the first embodiment, the patient type is one of normal, hypercapnic, or user-defined.

In some configurations of the first embodiment, the controller is further configured to record data corresponding to the measured FdO2 and the measured SpO2.

In some configurations of the first embodiment, the respiratory apparatus comprises a humidifier.

In some configurations of the first embodiment, the respiratory apparatus comprises an integrated blower and humidifier.

In some configurations of the first embodiment, the respiratory apparatus is configured to be portable.

In some configurations of the first embodiment, the respiratory apparatus is configured to have a controlled variable flow rate.

In some configurations of the first embodiment, the respiratory apparatus comprises a heated breathing tube.

In some configurations of the first embodiment, the ultrasonic sensor system comprises a first ultrasonic transducer and a second ultrasonic transducer.

In some configurations of the first embodiment, each of the first ultrasonic transducer and the second ultrasonic transducer is a receiver and a transmitter.

In some configurations of the first embodiment, the first ultrasonic transducer and the second ultrasonic transducer send pulses bidirectionally.

In some configurations of the first embodiment, the first ultrasonic transducer is a transmitter and the second ultrasonic transducer is a receiver.

In some configurations of the first embodiment, at least one of the first ultrasonic transducer or the second ultrasonic transducer send pulses along the gases flow In some configurations of the first embodiment, at least one of the first ultrasonic transducer or the second ultrasonic transducer send pulses across the gases flow.

In some configurations of the first embodiment, the controller is configured to display a first oxygen efficiency characteristic on a display of the respiratory apparatus.

In some configurations of the first embodiment, the controller is configured to display a second oxygen efficiency characteristic on a display of the respiratory apparatus, and the second indication of oxygen efficiency is based at least in part on an oxygen efficiency and a measured respiration rate of the patient.

In some configurations of the first embodiment, the second oxygen efficiency characteristic is calculated by dividing measured SpO2 by measured FdO2, and dividing the resulting value by the measured respiratory rate.

In some configurations of the first embodiment, the controller is configured to display a graph or trend line indicating at least one of the first oxygen efficiency characteristic or the second oxygen efficiency characteristic over a defined period of time.

In accordance with certain features, aspects and advantages of a second embodiment disclosed herein, a respiratory apparatus that provides a flow of gases to a patient, the respiratory apparatus comprising: a controller configured to control delivery of gases to the patient using closed loop control, the controller is configured to: control oxygen concentration (FdO2) of the gases flow to the patient; receive data from at least one patient sensor indicative of a measured oxygen saturation (SpO2) of the patient; receive data indicative of a measured FdO2 of the gases flow; receive a target SpO2 for the patient; and execute a step change to the FdO2 of the gases flow, a magnitude of the step change is based at least in part on the measured SpO2, the target SpO2 and an oxygen efficiency of the patient.

In some configurations of the second embodiment, the oxygen efficiency is determined based at least in part on measured SpO2 and measured FdO2.

In some configurations of the second embodiment, the oxygen efficiency is determined based at least in part on measured SpO2 divided by measured FdO2.

In some configurations of the second embodiment, the oxygen efficiency is determined based at least in part on a non-linear relationship between measured SpO2 of the patient and measured FdO2.

In some configurations of the second embodiment, the magnitude of the step change is based at least in part on recent changes to the target FdO2 prior to the step change.

In some configurations of the second embodiment, the magnitude of the step change is based at least in part on recent changes to the target FdO2 prior to the step change.

In some configurations of the second embodiment, a new target FdO2 is calculated based at least in part on the previous target FdO2.

In some configurations of the second embodiment, the controller is configured to execute a feed forward stage after the step change.

In some configurations of the second embodiment, the controller is further configured to maintain the target FdO2 immediately following the step change for a total duration of the feed forward stage.

In some configurations of the second embodiment, the feed forward stage ends if the measured SpO2 meets or exceeds the target SpO2.

In some configurations of the second embodiment, the feed forward stage ends if a maximum defined period of time is reached.

In some configurations of the second embodiment, the respiratory apparatus comprises a patient interface selected from at least one of: a face mask, a nasal mask, a nasal pillows mask, a tracheostomy interface, a nasal cannula, or an endotracheal tube.

In some configurations of the second embodiment, the nasal cannula is a non-sealed nasal cannula.

In some configurations of the second embodiment, the respiratory apparatus is configured to deliver a nasal high flow (NHF) flow of gases to the patient.

In some configurations of the second embodiment, the at least one patient sensor is a pulse oximeter.

In some configurations of the second embodiment, the respiratory apparatus comprises a humidifier.

In some configurations of the second embodiment, the respiratory apparatus comprises a gases composition sensor configured to determine the measured FdO2 during operation of the respiratory apparatus, and the gases composition sensor is an ultrasonic transducer system.

In some configurations of the second embodiment, the controller is further configured to execute a control phase after the feed forward stage.

In some configurations of the second embodiment, in the control phase the controller is further configured to control FdO2 of the gases flow to achieve the target FdO2 using feedback control.

In some configurations of the second embodiment, the controller is further configured to receive an indication of signal quality of the at least one patient sensor, and apply a weighting to the control of the FdO2 based at least in part on the signal quality.

In some configurations of the second embodiment, the controller is further configured to execute the control phase using a predicted SpO2 of the patient.

In some configurations of the second embodiment, the respiratory apparatus is configured to be portable.

In some configurations of the second embodiment, the controller is configured to display a first oxygen efficiency characteristic on a display of the respiratory apparatus.

In some configurations of the second embodiment, the controller is configured to display a second oxygen efficiency characteristic on a display of the respiratory apparatus, and the second indication of oxygen efficiency is based at least in part on an oxygen efficiency and a measured respiration rate of the patient.

In some configurations of the second embodiment, the second oxygen efficiency characteristic is calculated by dividing measured SpO2 by measured FdO2, and dividing the resulting value by the measured respiratory rate.

In some configurations of the second embodiment, the controller is configured to display a graph or trend line indicating at least one of the first oxygen efficiency characteristic or the second oxygen efficiency characteristic over a defined period of time.

In accordance with certain features, aspects and advantages of a third embodiment disclosed herein, a respiratory apparatus that provides a flow of gases to a patient, the respiratory apparatus comprising: a controller configured to control delivery of gases to the patient using closed loop control, wherein the controller is configured to: receive device parameter data indicative of an oxygen concentration (FdO2) of the gases flow; receive patient parameter data from at least one sensor indicative of an oxygen saturation (SpO2) reading of the patient, wherein the SpO2 of the patient is affected by the FdO2 of the gases flow; receive an indication of signal quality of the at least one sensor; and apply a weighting to the control of the FdO2 based at least in part on the signal quality.

In some configurations of the third embodiment, the indication of signal quality corresponds to specific SpO2 readings.

In some configurations of the third embodiment, the respiratory apparatus comprises a patient interface selected from at least one of: a face mask, a nasal mask, a nasal pillows mask, a tracheostomy interface, a nasal cannula, or an endotracheal tube.

In some configurations of the third embodiment, the nasal cannula is a non-sealed nasal cannula.

In some configurations of the third embodiment, the respiratory apparatus is configured to deliver a nasal high flow (NHF) flow of gases to the patient.

In some configurations of the third embodiment, the at least one sensor is a pulse oximeter.

In some configurations of the third embodiment, the controller is configured to receive input identifying characteristics of the patient.

In some configurations of the third embodiment, the controller is configured to control delivery of gases using a predicted SpO2 of the patient.

In some configurations of the third embodiment, the predicted SpO2 is based at least in part on a Smith predictor.

In some configurations of the third embodiment, the controller is configured to control delivery of gases using a patient specific model.

In some configurations of the third embodiment, the model is a patient specific model generated during a learning phase of a therapy session of the patient.

In some configurations of the third embodiment, the patient specific model is generated during the therapy session based at least in part on a default model.

In some configurations of the third embodiment, the patient specific model is updated during the therapy session.

In some configurations of the third embodiment, the model includes a delay time.

In some configurations of the third embodiment, the model includes an exponential decay.

In some configurations of the third embodiment, the model includes an oxygen efficiency of the patient.

In some configurations of the third embodiment, the oxygen efficiency is determined based at least in part on measured SpO2 and measured FdO2.

In some configurations of the third embodiment, the oxygen efficiency is determined based at least in part on measured SpO2 divided by measured FdO2.

In some configurations of the third embodiment, the oxygen efficiency is determined based at least in part on a non-linear relationship between measured SpO2 of the patient and measured FdO2.

In some configurations of the third embodiment, the respiratory apparatus is configured to be portable.

In accordance with certain features, aspects and advantages of a fourth embodiment disclosed herein, a respiratory apparatus that provides a flow of gases to a patient, the respiratory apparatus comprising: a controller configured to control delivery of gases to the patient using closed loop control, wherein the controller is configured to: control oxygen concentration (FdO2) of the gases flow to the patient; receive data from at least one patient sensor indicative of a measured oxygen saturation (SpO2) of the patient; receive data indicative of a measured FdO2 of the gases flow; receive a target SpO2 for the patient; and execute a wait stage, wherein during the wait stage the controller is configured to determine whether to execute a feed forward stage prior to transitioning to a control phase, wherein the target FdO2 of the gases flow is held constant during the wait stage; and execute a control phase wherein the FdO2 is controlled to achieve the target SpO2 using feedback control.

In some configurations of the fourth embodiment, the controller is further configured to determine whether to execute the feed forward stage based at least in part on the target SpO2 and the measured SpO2.

In some configurations of the fourth embodiment, the controller is further configured to determine whether to execute the feed forward stage based at least in part on an oxygen efficiency of the patient.

In some configurations of the fourth embodiment, the oxygen efficiency is determined based at least in part on measured SpO2 and measured FdO2.

In some configurations of the fourth embodiment, the oxygen efficiency is determined based at least in part on measured SpO2 divided by measured FdO2.

In some configurations of the fourth embodiment, the oxygen efficiency is determined based at least in part on a non-linear relationship between measured SpO2 of the patient and measured FdO2.

In some configurations of the fourth embodiment, if the controller determines to execute the feed forward stage, the controller executes the feed forward stage after the wait stage, and if the controller determines not to execute the feed forward stage, the controller executes the control phase after the wait phase.

In some configurations of the fourth embodiment, the controller is further configured to maintain a target FdO2 for a total duration of the feed forward stage.

In some configurations of the fourth embodiment, the feed forward stage ends if the measured SpO2 meets or exceeds the target SpO2.

In some configurations of the fourth embodiment, the feed forward stage ends if a maximum defined period of time is reached.

In some configurations of the fourth embodiment, the controller is further configured to execute the control phase after the feed forward stage.

In some configurations of the fourth embodiment, prior to execution of the feed forward stage, the controller is configured to determine whether to execute a step change to the FdO2 of the gases flow.

In some configurations of the fourth embodiment, the controller is further configured to determine whether to execute the step change based at least in part on recent changes to the target FdO2.

In some configurations of the fourth embodiment, the controller is further configured to determine whether to execute the step change based at least in part on the target SpO2 and the measured SpO2.

In some configurations of the fourth embodiment, the controller is further configured to determine whether to execute the step change based at least in part on an oxygen efficiency of the patient.

In some configurations of the fourth embodiment, a magnitude of the step change is based at least in part on the measured SpO2, the target SpO2 and an oxygen efficiency of the patient.

In some configurations of the fourth embodiment, the magnitude of the step change is based at least in part on recent changes to the target FdO2

In some configurations of the fourth embodiment, the respiratory apparatus comprises a patient interface selected from at least one of: a face mask, a nasal mask, a nasal pillows mask, a tracheostomy interface, a nasal cannula, or an endotracheal tube.

In some configurations of the fourth embodiment, the nasal cannula is a non-sealed nasal cannula.

In some configurations of the fourth embodiment, the respiratory apparatus is configured to deliver a nasal high flow (NHF) flow of gases to the patient.

In some configurations of the fourth embodiment, the at least one patient sensor is a pulse oximeter.

In some configurations of the fourth embodiment, the respiratory apparatus comprises a humidifier.

In some configurations of the fourth embodiment, the respiratory apparatus comprises a gases composition sensor configured to determine a measured FdO2 during operation of the respiratory apparatus, and the gases composition sensor is an ultrasonic transducer system.

In some configurations of the fourth embodiment, the controller is further configured to receive an indication of signal quality of the at least one patient sensor, and apply a weighting to the control of the FdO2 based at least in part on the signal quality.

In some configurations of the fourth embodiment, the controller is further configured to apply the weighting during the control phase.

In some configurations of the fourth embodiment, the controller is further configured to execute the control phase using a predicted SpO2 of the patient.

In some configurations of the fourth embodiment, the respiratory apparatus is configured to be portable.

In accordance with certain features, aspects and advantages of a fifth embodiment disclosed herein, a respiratory apparatus that provides a flow of gases to a patient, the respiratory apparatus comprising: a controller configured to control delivery of gases to the patient using closed loop control, wherein the controller is configured to: deliver a nasal high flow (NHF) gases flow to the patient; receive data from at least one patient sensor indicative of a measured oxygen saturation (SpO2) of the patient; receive data indicative of a measured fraction of delivered oxygen (FdO2) of the gases flow; determine an oxygen efficiency of the patient; and generate a patient specific model based on measured SpO2 and measured FdO2, wherein the patient specific model uses the oxygen efficiency of the patient.

In some configurations of the fifth embodiment, the oxygen efficiency is determined based at least in part on measured SpO2 and measured FdO2.

In some configurations of the fifth embodiment, the oxygen efficiency is determined based at least in part on measured SpO2 divided by measured FdO2.

In some configurations of the fifth embodiment, the oxygen efficiency is determined based at least in part on a non-linear relationship between measured SpO2 of the patient and measured FdO2.

In some configurations of the fifth embodiment, the patient specific model is generated based at least in part on a default model.

In some configurations of the fifth embodiment, the patient specific model is generated during a learning phase.

In some configurations of the fifth embodiment, the patient specific model is updated during a therapy session of the patient.

In some configurations of the fifth embodiment, the patient specific model models the magnitude of the change in SpO2 based at least in part on the change in FdO2.

In some configurations of the fifth embodiment, the patient specific model uses a flow rate of the gases flow.

In some configurations of the fifth embodiment, the patient specific model includes a delay time between a change in FdO2 and a change in SpO2 of the patient.

In some configurations of the fifth embodiment, the delay time is based at least in part on the flow rate of the gases flow.

In some configurations of the fifth embodiment, the patient specific model includes an exponential decay.

In some configurations of the fifth embodiment, the at least one patient sensor is a pulse oximeter.

In some configurations of the fifth embodiment, the respiratory apparatus comprises a humidifier.

In some configurations of the fifth embodiment, the FdO2 is measured using an ultrasonic transducer system.

In some configurations of the fifth embodiment, the ultrasonic transducer system comprises a first ultrasonic transducer and a second ultrasonic transducer.

In some configurations of the fifth embodiment, each of the first ultrasonic transducer and the second ultrasonic transducer is a receiver and a transmitter.

In some configurations of the fifth embodiment, the first ultrasonic transducer and the second ultrasonic transducer send pulses bidirectionally.

In some configurations of the fifth embodiment, the first ultrasonic transducer is a transmitter and the second ultrasonic transducer is a receiver.

In some configurations of the fifth embodiment, at least one of the first ultrasonic transducer or the second ultrasonic transducer send pulses along the gases flow.

In some configurations of the fifth embodiment, at least one of the first ultrasonic transducer or the second ultrasonic transducer send pulses across the gases flow.

In some configurations of the fifth embodiment, the respiratory apparatus is configured to be portable.

In accordance with certain features, aspects and advantages of a sixth embodiment disclosed herein, a respiratory apparatus that provides a flow of gases to a patient, the respiratory apparatus comprising: a controller configured to control delivery of gases to the patient using closed loop control, wherein the controller is configured to: control oxygen concentration (FdO2) of the gases flow to the patient; receive data from at least one patient sensor indicative of a measured oxygen saturation (SpO2) of the patient; receive data indicative of a measured FdO2 of the gases flow; receive a target SpO2 for the patient; execute a step change to the FdO2 of the gases flow to a target FdO2; execute a feed forward stage; and execute a control phase wherein the FdO2 is controlled to achieve the target SpO2 using feedback control.

In some configurations of the sixth embodiment, a magnitude of the step change is based at least in part on the measured SpO2, the target SpO2, and an oxygen efficiency of the patient.

In some configurations of the sixth embodiment, the target FdO2 is based at least in part on recent changes to the target FdO2 prior to the step change.

In some configurations of the sixth embodiment, the controller is further configured to maintain the target FdO2 immediately following the step change for a total duration of the feed forward stage.

In some configurations of the sixth embodiment, the feed forward stage ends if a maximum defined period of time is reached.

In some configurations of the sixth embodiment, the feed forward stage ends if the measured SpO2 meets or exceeds the target SpO2.

In some configurations of the sixth embodiment, the controller is further configured to execute the control phase after the feed forward stage.

In some configurations of the sixth embodiment, the respiratory apparatus comprises a patient interface selected from at least one of: a face mask, a nasal mask, a nasal pillows mask, a tracheostomy interface, a nasal cannula, or an endotracheal tube.

In some configurations of the sixth embodiment, the nasal cannula is a non-sealed nasal cannula.

In some configurations of the sixth embodiment, the respiratory apparatus is configured to deliver a nasal high flow (NHF) flow of gases to the patient.

In some configurations of the sixth embodiment, the at least one patient sensor is a pulse oximeter.

In some configurations of the sixth embodiment, the respiratory apparatus comprises a humidifier.

In some configurations of the sixth embodiment, the respiratory apparatus comprises a gases composition sensor configured to determine a measured FdO2 during operation of the respiratory apparatus, wherein the gases composition sensor is an ultrasonic transducer system.

In some configurations of the sixth embodiment, the controller is further configured to receive an indication of signal quality of the at least one patient sensor, and apply a weighting to the control of the FdO2 based at least in part on the signal quality.

In some configurations of the sixth embodiment, the controller is further configured to execute the control phase using a predicted SpO2 of the patient.

In some configurations of the sixth embodiment, the respiratory apparatus is configured to be portable.

In accordance with certain features, aspects and advantages of a seventh embodiment disclosed herein, a respiratory apparatus that provides a flow of gases to a patient, the respiratory apparatus comprising: a controller configured to control delivery of gases to the patient using closed loop control, wherein the controller is configured to: deliver the flow gases to the patient using nasal high flow (NHF); control an oxygen concentration (FdO2) of the gases flow to the patient; receive data from at least one patient sensor indicative of a measured oxygen saturation (SpO2) of the patient; receive a target SpO2 for the patient; and execute a step change to the FdO2 of the gases flow, wherein a magnitude of the step change is based at least in part on the measured SpO2 and the target SpO2 of the patient.

In some configurations of the seventh embodiment, the step change is further based at least in part on an oxygen efficiency of the patient.

In some configurations of the seventh embodiment, the oxygen efficiency is determined based at least in part on measured SpO2 and measured FdO2.

In some configurations of the seventh embodiment, the oxygen efficiency is determined based at least in part on measured SpO2 divided by measured FdO2.

In some configurations of the seventh embodiment, the oxygen efficiency is determined based at least in part on a non-linear relationship between measured SpO2 of the patient and measured FdO2.

In some configurations of the seventh embodiment, the magnitude of the step change is based at least in part on changes to the target FdO2 within a defined time period prior to the step change.

In some configurations of the seventh embodiment, a new target FdO2 is calculated based at least in part on the previous target FdO2.

In some configurations of the seventh embodiment, the controller is configured to execute a feed forward stage after the step change.

In some configurations of the seventh embodiment, the controller is further configured to maintain the FdO2 at the target FdO2 for a total duration of the feed forward stage.

In some configurations of the seventh embodiment, the feed forward stage ends if the measured SpO2 meets or exceeds the target SpO2.

In some configurations of the seventh embodiment, the feed forward stage ends if a maximum defined period of time is reached.

In some configurations of the seventh embodiment, the respiratory apparatus comprises a patient interface selected from at least one of: a face mask, a nasal mask, a nasal pillows mask, a tracheostomy interface, a nasal cannula, or an endotracheal tube.

In some configurations of the seventh embodiment, the nasal cannula is a non-sealed nasal cannula.

In some configurations of the seventh embodiment, the at least one patient sensor is a pulse oximeter.

In some configurations of the seventh embodiment, the respiratory apparatus comprises a humidifier.

In some configurations of the seventh embodiment, the respiratory apparatus comprises a gases composition sensor configured to determine the measured FdO2 during operation of the respiratory apparatus, and the gases composition sensor is an ultrasonic transducer system.

In some configurations of the seventh embodiment, the controller is further configured to execute a control phase after the feed forward stage.

In some configurations of the seventh embodiment, in the control phase the controller is further configured to control FdO2 of the gases flow to achieve the target FdO2 using feedback control.

In some configurations of the seventh embodiment, the controller is further configured to receive an indication of signal quality of the at least one patient sensor, and apply a weighting to the control of the FdO2 based at least in part on the signal quality.

In some configurations of the seventh embodiment, the controller is further configured to execute the control phase using a predicted SpO2 of the patient.

In some configurations of the seventh embodiment, the respiratory apparatus is configured to be portable.

In some configurations of the seventh embodiment, the controller is configured to display a first oxygen efficiency characteristic on a display of the respiratory apparatus.

In some configurations of the seventh embodiment, the controller is configured to display a second oxygen efficiency characteristic on a display of the respiratory apparatus, and the second indication of oxygen efficiency is based at least in part on an oxygen efficiency and a measured respiration rate of the patient.

In some configurations of the seventh embodiment, the second oxygen efficiency characteristic is calculated by dividing measured SpO2 by measured FdO2, and dividing the resulting value by the measured respiratory rate.

In some configurations of the seventh embodiment, the controller is configured to display a graph or trend line indicating at least one of the first oxygen efficiency characteristic or the second oxygen efficiency characteristic over a defined period of time.

In accordance with certain features, aspects and advantages of at least one of the embodiments disclosed herein, a respiratory apparatus that provides a flow of gases to a patient, the respiratory apparatus comprising: a controller configured to control delivery of gases to the patient using closed loop control, wherein the controller is configured to: receive patient parameter data indicative of oxygen saturation (SpO2) of the patient from at least one sensor; and execute a control phase, wherein operation of the respiratory apparatus during a therapy session is based at least in part on the patient parameter data.

In some configurations, the apparatus comprises a patient interface selected from at least one of: a face mask, a nasal mask, a nasal pillows mask, a tracheostomy interface, a nasal cannula, or an endotracheal tube.

In some configurations, the respiratory apparatus is configured to deliver a nasal high flow (NHF) flow of gases to the patient.

In some configurations, at least one sensor is a pulse oximeter.

In some configurations, the apparatus comprises an supplementary gas inlet valve.

In some configurations, the controller is configured to control operation of the supplementary gas inlet valve.

In some configurations, the supplementary gas inlet valve is a proportional valve.

In some configurations, the supplementary gas inlet valve is an oxygen inlet valve.

In some configurations, the apparatus comprises an ambient air inlet.

In some configurations, the oxygen inlet valve is in fluid communication with a filter module, wherein the respiratory apparatus is configured to entrain oxygen received from the oxygen inlet valve with ambient air from the ambient air inlet in the filter module.

In some configurations, the apparatus comprises a gases composition sensor configured to determine at least the oxygen content of gases flow during operation of the respiratory apparatus.

In some configurations, the gases composition sensor is an ultrasonic transducer system.

In some configurations, the gases composition sensor is positioned downstream of a blower module of the respiratory apparatus.

In some configurations, the filter module is positioned upstream of the blower module of the respiratory apparatus.

In some configurations, the closed loop control includes using a first closed loop control model configured to determine a target fraction of delivered oxygen (FdO2).

In some configurations, the target FdO2 is determined based at least in part on target SpO2 and patient SpO2.

In some configurations, the target FdO2 is further based at least in part on measured FdO2.

In some configurations, the closed loop control includes using a second closed loop control model configured to determine a control signal for an oxygen inlet valve.

In some configurations, the control signal for the oxygen valve is determined based at least in part on the target FdO2 and the measured FdO2.

In some configurations, the control signal for the oxygen valve is determined further based at least in part on a gases flow rate.

In some configurations, the controller is configured to transfer to a manual mode of operation when a signal quality of the at least one sensor is below a threshold.

In some configurations, the controller is configured to transfer to a manual mode of operation when the patient SpO2 is outside of defined limits.

In some configurations, the controller is configured to receive an indication of signal quality, and apply a weighting to the control of the FdO2 based at least in part on the signal quality.

In some configurations, the indication of signal quality corresponds to specific SpO2 readings.

In some configurations, the controller is configured to execute a plurality of phases during a therapy session of the respiratory apparatus, wherein the controller is configured to: execute a learning phase, wherein during the learning phase the controller is configured to generate a patient specific model; and execute the control phase based at least in part on the patient specific model.

In some configurations, during the learning phase the controller is configured to: receive device parameter data indicative of oxygen concentration of the gases flow provided to the patient; and receive patient parameter data indicative of oxygen saturation of the patient from at least one sensor.

In some configurations, the controller is configured to generate the patient specific model based at least in part on a relationship between the oxygen concentration of the gases flow and the oxygen saturation of the patient.

In some configurations, the learning phase has a maximum duration.

In some configurations, the learning phase is executed a plurality of times during the therapy session.

In some configurations, the controller is further configured to change the oxygen concentration during the learning phase.

In some configurations, the controller is further configured to change the oxygen concentration after the controller detects that the measured oxygen saturation of the patient parameter is stable.

In some configurations, the change is to increase the oxygen concentration.

In some configurations, the change is to decrease the oxygen concentration.

In some configurations, the patient specific model is based at least in part on signal quality data of the sensor recorded during the learning phase.

In some configurations, the patient specific model determines a delay time, wherein the delay time is a period of time between when a change in oxygen concentration of the gases flow occurs and a response in oxygen saturation of the patient.

In some configurations, the patient specific model calculates an exponential decay.

In some configurations, parameters of the patient specific model includes at least one of: delay time, rate of exponential decay, change in oxygen concentration, and change in blood oxygen saturation.

In some configurations, the controller is further configured to execute the control phase after the patient specific model satisfies defined characterization criteria.

In some configurations, the defined characterization criteria defines, for each of one or more of the parameters of the patient specific model, an acceptable value range for the parameter.

In some configurations, the control phase is configured to be executed using a PID control based at least in part on the patient specific model.

In some configurations, the controller is configured to receive device parameter data indicative of oxygen concentration of the gases flow.

In some configurations, the controller is configured to predict the oxygen saturation of the patient based at least in part on oxygen concentration of the gases flow.

In some configurations, the prediction is at least partially based on one or more patient parameter readings.

In some configurations, the previous predictions of the patient parameter are compared with measured patient parameter readings to calculate model error.

In some configurations, the model error is weighted by signal quality.

In some configurations, the model error is used to correct the current prediction.

In some configurations, the prediction is based on a model.

In some configurations, the model is patient specific.

In some configurations, the model is generated during a learning phase of the therapy session.

In some configurations, the control phase is configured to be executed using a predictive algorithm for predicting the oxygen saturation of the patient.

In some configurations, the predictive algorithm is a Smith predictor.

In some configurations, the output of the predictive algorithm is based at least in part on a patient specific model.

In some configurations, the controller is configured to receive input identifying characteristics of the patient.

In some configurations, the patient characteristics include at least one of a patient type, age, weight, height, or gender.

In some configurations, the patient type is one of normal, hypercapnic, or user-defined.

In some configurations, the controller is configured to execute a learning phase, wherein during the learning phase the controller is configured to: receive device parameter data indicative of oxygen concentration of the gases flow provided to the patient; receive patient parameter data indicative of oxygen saturation of the patient from at least one sensor; and calculate one or more model parameters for a patient specific model based on the device parameter data and the patient parameter data; determine that at least one of the one or more parameters does not satisfy patient characterization criteria for generation of a patient specific model; and execute the control phase, wherein operation of the respiratory apparatus during the therapy session is based at least in part on a default patient model.

In some configurations, the default patient model is selected from the plurality of default patient models based at least in part on one or more of the patient characteristics.

In some configurations, the default patient model is selected from the plurality of default patient models based at least in part on the patient type.

In some configurations, the controller is further configured to record data corresponding to the measured oxygen concentration and the measured oxygen saturation.

In some configurations, the controller is further configured to stop recording data after a defined period of time.

In some configurations, the controller is further configured to stop recording data after the patient specific model satisfies defined characterization criteria.

In some configurations, the apparatus comprises a humidifier.

In some configurations, the apparatus comprises an integrated blower and humidifier.

In some configurations, the respiratory apparatus is configured to be portable.

In some configurations, the respiratory apparatus is configured to have a controlled variable flow rate.

In some configurations, the target FdO2 is further based at least in part on signal quality.

In some configurations, the respiratory apparatus is configured to vary flow rate by varying motor speed of the blower.

In accordance with certain features, aspects and advantages of at least one of the embodiments disclosed herein, a method of providing a flow of gases to a patient, the method comprising: by a controller of a respiratory apparatus, receiving patient parameter data indicative of oxygen saturation of the patient from at least one sensor; and controlling operation of the respiratory therapy apparatus using closed loop control during a control phase of the therapy session based at least in part on the patient parameter data.

In some configurations, the method comprises executing a learning phase during a therapy session, the learning phase including: receiving device parameter data indicative of oxygen concentration of the gases flow provided to the patient and patient parameter data indicative of oxygen saturation of the patient from at least one sensor; generating a patient specific model based at least in part on a relationship between the oxygen concentration of the gases flow and the oxygen saturation of the patient.

In some configurations, the method comprises controlling operation of the respiratory therapy apparatus during a control phase of the therapy session based at least in part on the patient specific model.

In some configurations, the method comprises recording data corresponding to the measured oxygen concentration and the measured oxygen saturation.

In some configurations, the method comprises stopping the recording data after a defined period of time.

In some configurations, the method comprises generating the patient specific model based at least in part on signal quality data of the at least one sensor recorded during the learning phase.

In some configurations, parameters of the patient specific model includes at least one of: delay time, rate of exponential decay, change in oxygen concentration, and change in blood oxygen saturation.

In some configurations, the method comprises executing the control phase after the patient specific model satisfies defined characterization criteria.

In some configurations, the defined characterization criteria defines, for each of one or more of the parameters of the patient specific model, an acceptable value range for the parameter.

In some configurations, the method comprises executing the control phase using a PID control based at least in part on the patient specific model.

In some configurations, the method comprises executing the control phase using a predictive algorithm for predicting the oxygen saturation of the patient.

In some configurations, the method comprises using the predicted oxygen saturation during the control phase.

In some configurations, the predictive algorithm is a Smith predictor.

In some configurations, the output of the predictive algorithm is based at least in part on the patient specific model.

In some configurations, the method comprises receiving input identifying characteristics of the patient.

In some configurations, the patient characteristics include at least one of a patient type, age, weight, height, or gender.

In some configurations, the method comprises changing the oxygen concentration during the learning phase.

In some configurations, the method comprises changing the oxygen concentration during the learning phase after detecting that the measured oxygen saturation of the patient parameter is stable.

In some configurations, the change is to increase the oxygen concentration.

In some configurations, the change is to decrease the oxygen concentration.

In some configurations, the method comprises executing the learning phase a plurality of times during the therapy session.

In some configurations, the method comprises transferring to a manual mode of operation when a signal quality of the at least one sensor is below a threshold.

In some configurations, the method comprises transferring to a manual mode of operation when the patient SpO2 is outside of defined limits.

In some configurations, the method comprises determining a target FdO2 using a first closed control loop.

In some configurations, the target FdO2 is determined based at least in part on a target SpO2 and patient SpO2.

In some configurations, the target FdO2 is further based at least in part on measured FdO2.

In some configurations, the method comprises determining a control signal for an oxygen inlet valve using a second closed control loop.

In some configurations, the control signal is determined based at least in part on a the target FdO2 and the measured FdO2.

In some configurations, the control signal for the oxygen valve is further based at least in part on a gases flow rate.

In some configurations, the method comprises adjusting the oxygen inlet valve based on the control signal.

In some configurations, the method comprises entraining oxygen from the oxygen inlet valve with ambient air from an ambient air inlet within a filter module of the respiratory apparatus.

In some configurations, the method comprises receiving an indication of signal quality, and applying a weighting to the control of the FdO2 based at least in part on the signal quality.

In some configurations, the method comprises determining at least the oxygen content of gases flow during operation of the respiratory apparatus.

In some configurations, the target FdO2 is further based at least in part on signal quality.

In accordance with certain features, aspects and advantages of at least one of the embodiments disclosed herein, a respiratory apparatus that provides a flow of gases to a patient, the respiratory apparatus comprising: a controller configured to control delivery of gases to the patient, wherein the controller is configured to: execute a learning phase, wherein during the learning phase the controller is configured to: receive device parameter data indicative of oxygen concentration of the gases flow provided to the patient; receive patient parameter data indicative of oxygen saturation of the patient from at least one sensor; and generate a patient specific model based at least in part on a relationship between the oxygen concentration of the gases flow and the oxygen saturation of the patient; and execute a control phase, wherein operation of the respiratory apparatus during a therapy session is based at least in part on the patient specific model.

In some configurations, the apparatus comprises patient interface is selected from at least one of: a face mask, a nasal mask, a nasal pillows mask, a tracheostomy interface, a nasal cannula, or an endotracheal tube.

In some configurations, the respiratory apparatus is an apparatus that delivers a nasal high flow (NHF) flow of gases.

In some configurations, the sensor is a pulse oximeter.

In some configurations, the controller is further configured to record data corresponding to the measured oxygen concentration and the measured oxygen saturation.

In some configurations, the controller is further configured to stop recording data after a defined period of time.

In some configurations, the patient specific model is based at least in part on signal quality data of the sensor recorded during the learning phase.

In some configurations, the patient specific model determines a delay time, wherein the delay time is a period of time between when a change in oxygen concentration of the gases flow and a response in oxygen saturation of the patient.

In some configurations, the patient specific model calculates an exponential decay.

In some configurations, parameters of the patient specific model includes at least one of: delay time, rate of exponential decay, change in oxygen concentration, and change in blood oxygen saturation.

In some configurations, the controller is further configured to execute the control phase after the patient specific model satisfies defined characterization criteria.

In some configurations, the defined characterization criteria defines, for each of one or more of the parameters of the patient specific model, an acceptable value range for the parameter.

In some configurations, the control phase is configured to be executed using closed loop control.

In some configurations, the control phase is configured to be executed using a PID control based at least in part on the patient specific model.

In some configurations, the control phase is configured to be executed using a predictive algorithm for predicting the oxygen saturation of the patient.

In some configurations, the controller is further configured to use the predicted oxygen saturation during the control phase.

In some configurations, the predictive algorithm is a Smith predictor.

In some configurations, the output of the predictive algorithm is based at least in part on the patient specific model.

In some configurations, the controller is configured to receive input identifying characteristics of the patient.

In some configurations, the patient characteristics include at least one of a patient type, age, weight, height, or gender.

In some configurations, the controller is further configured to change the oxygen concentration during the learning phase.

In some configurations, the controller is further configured to change the oxygen concentration after the controller detects that the measured oxygen saturation of the patient parameter is stable. In some configurations, the change is to increase the oxygen concentration. In some configurations, the change is to decrease the oxygen concentration.

In some configurations, the learning phase is executed a plurality of times during the therapy session.

Additionally, in accordance with certain features, aspects and advantages of at least one of the embodiments disclosed herein, a respiratory apparatus that provides a flow of gases to a patient, wherein the respiratory apparatus is configured to deliver a nasal high flow (NHF) flow of gases to the patient, the respiratory apparatus comprising: a controller configured to control operation of the respiratory apparatus and execute a plurality of phases during a therapy session of the respiratory apparatus, wherein the controller is configured to: execute a learning phase, wherein during the learning phase the controller is configured to generate a patient specific model; and execute a control phase, wherein operation of the respiratory apparatus during the therapy session is based at least in part on the patient specific model.

In some configurations, during the learning phase, the controller is further configured to measure a property of the gases flow provided to the patient. In some configurations, the property is oxygen concentration of the gases flow.

In some configurations, during the learning phase, the controller is further configured to measure a physiological parameter of the patient using at least one sensor. In some configurations, the physiological parameter is oxygen saturation of the patient.

In some configurations, the controller is further configured to: receive device parameter data indicative of oxygen concentration of the gases flow provided to the patient; and receive patient parameter data indicative of oxygen saturation of the patient from at least one sensor. In some configurations, during the learning phase, the controller is further configured to generate a patient specific model based at least in part on a relationship between the oxygen concentration of the gases flow and the oxygen saturation of the patient.

In some configurations, the at least one sensor is a pulse oximeter.

In some configurations, the controller is further configured to change the oxygen concentration during the learning phase. In some configurations, the controller is further configured to change the oxygen concentration after the controller detects that the measured oxygen saturation of the patient parameter is stable. In some configurations, the change is to increase the oxygen concentration. In some configurations, the change is to decrease the oxygen concentration.

In some configurations, the controller is further configured to record data corresponding to the measured oxygen concentration and the measured oxygen saturation.

In some configurations, the controller is further configured to stop recording data after a defined period of time.

In some configurations, the controller is further configured to stop recording data after the patient specific model satisfies defined characterization criteria.

In some configurations, the patient specific model is based at least in part on signal quality data of the sensor recorded during the learning phase.

In some configurations, error values for sensor data can be weighted by the corresponding signal quality data.

In some configurations, the patient specific model determines a delay time, wherein the delay time is a period of time between when a change in oxygen concentration of the gases flow and a response in oxygen saturation of the patient.

In some configurations, the patient specific model calculates an exponential decay.

In some configurations, parameters of the patient specific model includes at least: delay time, rate of exponential decay, change in oxygen concentration, and change in blood oxygen saturation.

In some configurations, the control phase is configured to be executed using closed loop control.

In some configurations, the control phase is configured to be executed using a PID control based at least in part on the patient specific model.

In some configurations, the control phase is configured to be executed using a predictive algorithm for predicting the physiological parameter of the patient.

In some configurations, the controller is further configured to use the predicted oxygen saturation during the control phase.

In some configurations, the predictive algorithm is a Smith predictor.

In some configurations, the output of the predictive algorithm is based at least in part on the patient specific model.

In some configurations, the learning phase is executed a plurality of times during the therapy session.

In some configurations, the controller is configured to receive input identifying characteristics of the patient. In some configurations, the patient characteristics include at least one of a patient type, age, weight, height, or gender. In some configurations, the patient type is one of normal, hypercapnic, or user-defined.

Additionally, in accordance with certain features, aspects and advantages of at least one of the embodiments disclosed herein, a respiratory apparatus that provides a flow of gases to a patient, the respiratory apparatus comprising: a controller configured to control delivery of gases to the patient, wherein the controller is configured to: receive device parameter data indicative of oxygen concentration of the gases flow; receive patient parameter data indicative of an oxygen saturation reading of the patient, wherein the oxygen saturation of the patient is affected by the oxygen concentration of the gases flow; and predict the oxygen saturation of the patient based at least in part on the oxygen concentration of the gases flow.

In some configurations, the apparatus comprises a patient interface selected from at least one of: a face mask, a nasal mask, a nasal pillows mask, a tracheostomy interface, a nasal cannula, or an endotracheal tube.

In some configurations, the respiratory apparatus is an apparatus that delivers a nasal high flow (NHF) flow of gases.

In some configurations, the sensor is a pulse oximeter.

In some configurations, the prediction is at least partially based on one or more patient parameter readings. In some configurations, the previous predictions of the patient parameter are compared with measured patient parameter readings to calculate model error.

In some configurations, the model error is weighted by signal quality.

In some configurations, the model error is used to correct the current prediction.

In some configurations, the prediction is based on a model.

In some configurations, the model is patient specific.

In some configurations, the model is generated during a learning phase of the therapy session.

In some configurations, the patient specific model determines a delay time, wherein the delay time is a period of time between when a change in oxygen concentration of the gases flow and a response in oxygen saturation of the patient.

In some configurations, the patient specific model includes an exponential decay.

In some configurations, the controller is further configured to use the predicted oxygen saturation during the control phase.

In some configurations, the prediction is based on a Smith predictor.

In some configurations, the controller is configured to execute the control of the delivery of gases using closed loop control.

In some configurations, the model is based at least in part on signal quality data of the sensor recorded during the learning phase.

Additionally, in accordance with certain features, aspects and advantages of at least one of the embodiments disclosed herein, a respiratory apparatus that provides a flow of gases to a patient, the respiratory apparatus comprising: a controller configured to control delivery of gases to the patient using closed loop control, wherein the controller is configured to: receive device parameter data indicative of oxygen concentration of the gases flow; receive patient parameter data indicative of an oxygen saturation reading of the patient, wherein the oxygen saturation of the patient is affected by the oxygen concentration of the gases flow; receive an indication of signal quality; and apply a weighting to the control of the oxygen concentration based at least in part on the signal quality.

In some configurations, the indication of signal quality corresponds to specific oxygen saturation readings.

In some configurations, the apparatus comprises a patient interface selected from at least one of: a face mask, a nasal mask, a nasal pillows mask, a tracheostomy interface, a nasal cannula, or an endotracheal tube.

In some configurations, the sensor is a pulse oximeter.

In some configurations, the controller is configured to control delivery of gases using a predictive algorithm for predicting the oxygen saturation of the patient. In some configurations, the output of the predictive algorithm is based at least in part on a model. In some configurations, the model is patient specific. In some configurations, the model is generated during a learning phase of the therapy session. In some configurations, the model includes a delay time. In some configurations, the model includes an exponential decay. In some configurations, the predictive algorithm is a Smith predictor.

In some configurations, the controller is configured to receive input identifying characteristics of the patient.

Additionally, in accordance with certain features, aspects and advantages of at least one of the embodiments disclosed herein, a respiratory apparatus that provides a flow of gases to a patient, the respiratory apparatus comprising: a controller configured to control delivery of gases to the patient, wherein the controller is configured to: execute a learning phase, wherein during the learning phase the controller is configured to: receive device parameter data indicative of oxygen concentration of the gases flow provided to the patient; receive patient parameter data indicative of oxygen saturation of the patient from at least one sensor; and calculate one or more model parameters for a patient specific model based on the device parameter data and the patient parameter data; determine that at least one of the one or more parameters does not satisfy patient characterization criteria for generation of a patient specific model; and execute a control phase, wherein operation of the respiratory apparatus during a therapy session is based at least in part on a default patient model.

In some configurations, the apparatus comprises a patient interface selected from at least one of: a face mask, a nasal mask, a nasal pillows mask, a tracheostomy interface, a nasal cannula, or an endotracheal tube.

In some configurations, the respiratory apparatus is an apparatus that delivers a nasal high flow (NHF) flow of gases.

In some configurations, the sensor is a pulse oximeter.

In some configurations, the controller is further configured to record data corresponding to measured oxygen concentration and measured oxygen saturation.

In some configurations, the one or more mode parameters include at least one of: delay time, rate of exponential decay, change in oxygen concentration, or change in blood oxygen saturation.

In some configurations, the default patient model is selected from one of a plurality of default patient models.

In some configurations, the controller is configured to receive input one or more patient characteristics. In some configurations, the patient characteristics include at least one of a patient type, age, weight, height, or gender. In some configurations, the patient type is one of normal, hypercapnic, or user-defined. In some configurations, the default patient model is selected from the plurality of default patient models based at least in part on the one or more patient characteristics. In some configurations, the default patient model is selected from the plurality of default patient models based at least in part on the patient type.

In some configurations, the control phase is configured to be executed using closed loop control.

In some configurations, the control phase is configured to be executed using a PID control based at least in part on the default patient model.

In some configurations, the control phase is configured to be executed using a predictive algorithm for predicting the oxygen saturation of the patient.

In some configurations, the controller is further configured to use the predicted oxygen saturation during the control phase to control delivery of gases to the patient.

In some configurations, the predictive algorithm is a Smith predictor.

In some configurations, the output of the predictive algorithm is based at least in part on the default patient model.

Additionally, in accordance with certain features, aspects and advantages of at least one of the embodiments disclosed herein, a method of providing a flow of gases to a patient, the method comprising: by a controller of a respiratory therapy apparatus, executing a learning phase during a therapy session, the learning phase including: receiving device parameter data indicative of oxygen concentration of the gases flow provided to the patient; receiving patient parameter data indicative of oxygen saturation of the patient from at least one sensor; and generating a patient specific model based at least in part on a relationship between the oxygen concentration of the gases flow and the oxygen saturation of the patient; and controlling operation of the respiratory therapy apparatus during a control phase of the therapy session based at least in part on the patient specific model.

The method can include recording data corresponding to the measured oxygen concentration and the measured oxygen saturation.

The method can include stopping the recording data after a defined period of time.

The method can include generating the patient specific model based at least in part on signal quality data of the at least one sensor recorded during the learning phase.

The parameters of the patient specific model includes at least one of: delay time, rate of exponential decay, change in oxygen concentration, and change in blood oxygen saturation.

The method can include executing the control phase after the patient specific model satisfies defined characterization criteria. The defined characterization criteria can define, for each of one or more of the parameters of the patient specific model, an acceptable value range for the parameter.

The method can include executing the control phase using a PID control based at least in part on the patient specific model.

The method can include executing the control phase using a predictive algorithm for predicting the oxygen saturation of the patient. The method can include using the predicted oxygen saturation during the control phase. The predictive algorithm can be a Smith predictor. The output of the predictive algorithm can be based at least in part on the patient specific model.

The method can include receiving input identifying characteristics of the patient. The patient characteristics can include at least one of a patient type, age, weight, height, or gender.

The method can include changing the oxygen concentration during the learning phase. The method can include changing the oxygen concentration during the learning phase after detecting that the measured oxygen saturation of the patient parameter is stable. The change can increase the oxygen concentration. The change can decrease the oxygen concentration.

The method can include executing the learning phase a plurality of times during the therapy session.

Features from one or more embodiments or configurations may be combined with features of one or more other embodiments or configurations. Additionally, more than one embodiment may be used together during a process of respiratory support of a patient.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

DETAILED DESCRIPTION

Figure 1A:
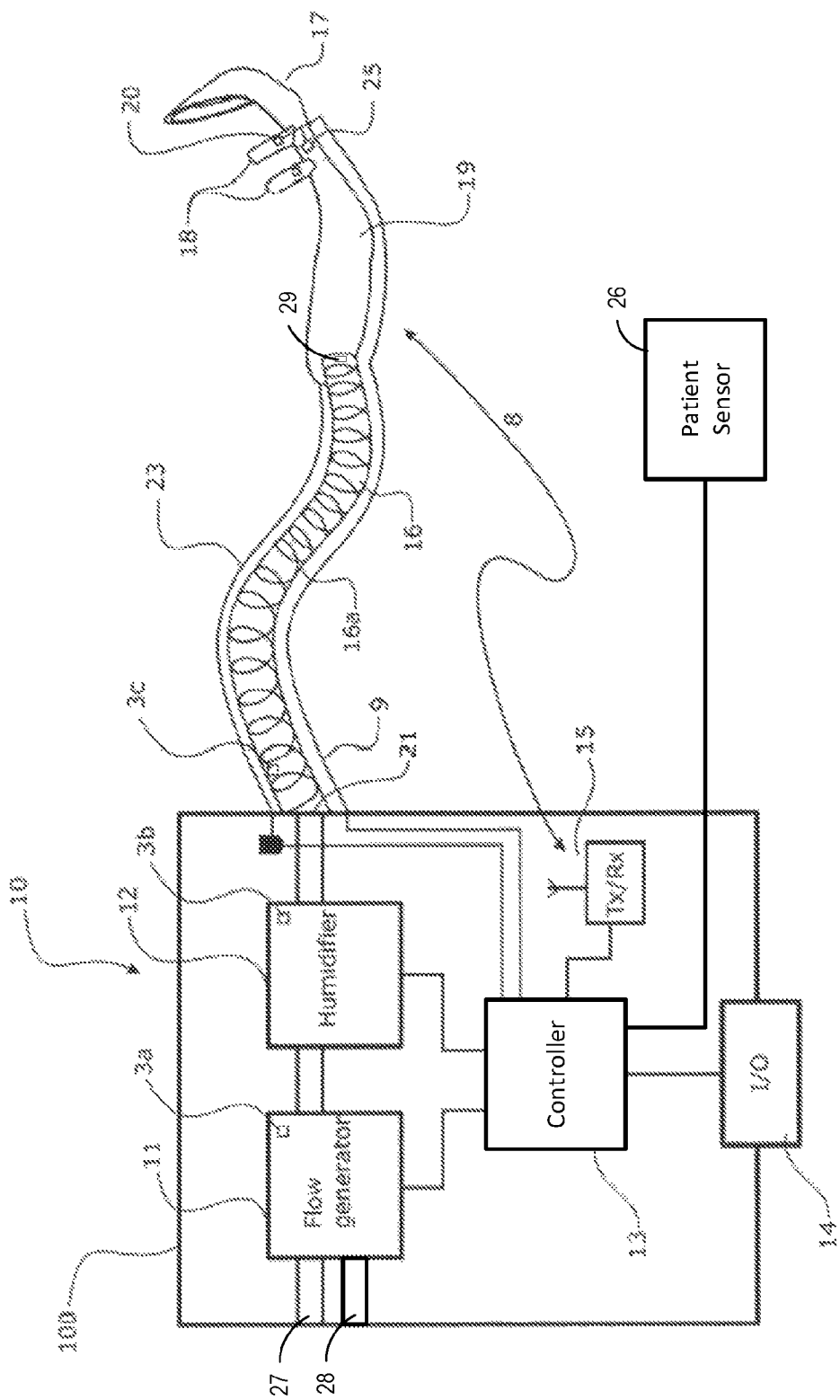
FIG. 1A shows in diagrammatic form a flow therapy apparatus.

Patients suffering from various health conditions and diseases can benefit from oxygen therapy. For example, patients suffering from chronic obstructive pulmonary disease (COPD), pneumonia, asthma, bronchopulmonary dysplasia, heart failure, cystic fibrosis, sleep apnea, lung disease, trauma to the respiratory system, acute respiratory distress, receiving pre- and post-operative oxygen delivery, and other conditions or diseases can benefit from oxygen therapy. A common way of treating such problems is by supplying the patients with supplemental oxygen to prevent their blood oxygen saturation (SpO2) from dropping too low (e.g., below about 90%). However, supplying the patient with too much oxygen can over oxygenate their blood, and is also considered dangerous. Generally, the patient's SpO2 is kept in a range from about 80% to about 99%, and preferably about 92% to about 96%, although these ranges may differ due to patient conditions. Due to various factors such as respiratory rate, lung tidal volume, heart rate, activity levels, height, weight, age, gender, and other factors, there is no one prescribed level of supplemental oxygen that can consistently achieve an SpO2 response in the targeted range for each patient. Individual patients will regularly need their fraction of oxygen delivered to the patient (FdO2) monitored and adjusted to ensure they are receiving the correct FdO2 to achieve the targeted SpO2. Achieving a correct and consistent SpO2 is an important factor in treating patients with various health conditions or diseases. Additionally, patients suffering from these health problems may find benefit from a system that automatically controls oxygen saturation. The present disclosure is applicable to a wide range of patients that require fast and accurate oxygen saturation control.

The fraction of oxygen delivered to a patient (FdO2) may be controlled manually. A clinician can manually adjust an oxygen supply valve to change the flow rate or fraction of oxygen being delivered to the patient. The clinician can determine SpO2 levels of the patient using a patient monitor, such as a pulse oximeter. The clinician can continue to manually adjust the amount of oxygen being delivered to the patient until the SpO2 level of the patient reaches a determined level.

One problem with current methods is that when the clinician is trying to achieve a specific SpO2 level they would need to alter the FdO2, wait for the SpO2 reading to settle, and then apply further changes to the FdO2 until the SpO2 is at the required level. The repetitive process of altering the FdO2 and waiting for the SpO2 to settle can be a very time consuming process, particularly if multiple patients are requiring the same treatment.

Another problem is the accuracy of the SpO2 that can be achieved. Accuracy of the SpO2 control can be dependent on how fine the increments are for displayed SpO2 and selectable FdO2. The accuracy may be hampered by the increased amount of time required to get increasingly accurate values, as a clinician may get close to the ideal SpO2 and decide not to alter the FdO2 any further.

Another problem is that other factors may cause the patient's SpO2 levels to change over time without any change in FdO2. Patients would need to be regularly checked on and have their FdO2 adjusted in order to maintain their SpO2 at the correct value. This process can be quite time consuming for the clinician. Additionally, if the time between adjustments is too long, the patient can be at risk of their SpO2 drifting too far from the targeted level.

While some systems exist that attempt something similar, many of them are plagued by further problems stemming from difficulties in measuring patient oxygen saturation. Pulse oximeters and similar devices generate a signal that lags far behind the corresponding change in oxygen fraction delivered. Additionally, oxygen saturation readings can become inaccurate due to various factors.

The present disclosure provides for closed loop control of a flow therapy apparatus that allows a patient or clinician to set a target SpO2 instead of a target FdO2. The flow therapy apparatus can automatically alter the FdO2 of the flow therapy apparatus to achieve the targeted SpO2 based on values of target SpO2, current SpO2, and current FdO2. Automatically controlling the FdO2 can help to quickly and accurately adjust the FdO2 until a target SpO2 is achieved. In some configurations, the system can generate a patient specific model for each patient at the initiation of a therapy session. The flow therapy apparatus can have greater precision in achieving the targeted SpO2 by adjusting the FdO2, as needed, to stay within the targeted SpO2 range, without being constantly monitored by a clinician.

The present disclosure provides for a flow therapy apparatus that can implement one or more closed loop control systems. Features of the closed loop control system may be combined with features of one or more configurations disclosed herein.

The flow therapy apparatus may operate in automatic mode or manual mode. In automatic mode, the controller can automatically control the FdO2 based on a target FdO2 determined based on the target SpO2 and/or measured SpO2. A valve at the oxygen inlet may be connected to the controller that can control the oxygen concentration in gases flow based on a target FdO2. The controller can execute a control algorithm that can measure FdO2 output by the flow therapy apparatus. The FdO2 measurement may be taken periodically at a defined frequency, such as a maximum sample rate of the gases concentration sensors or at a lower frequency, or the measurement may be taken aperiodically. The controller can continue to adjust the valve at the oxygen inlet until the measured FdO2 arrives at the target FdO2. The measured FdO2 may be determined by a gases composition sensor.

In manual mode, the controller can receive a target FdO2 from a clinician or patient, such as via a user interface. The controller can automatically control the FdO2 based on the received target FdO2. The controller can control the oxygen concentration in gases flow by controlling the oxygen inlet valve based on a target FdO2. The controller can execute a control algorithm that can use a measured FdO2 output by the flow therapy apparatus (for example, by a gases composition sensor of the flow therapy apparatus) as an input to the controller. The FdO2 measurement may be taken periodically at a defined frequency, such as a maximum sample rate of the gases concentration sensors or at a lower frequency, or the measurement may be taken aperiodically. The controller can continue to adjust the valve at the oxygen inlet to drive the measured FdO2 towards the target FdO2. The measured FdO2 may be determined by a gases composition sensor.

The flow therapy apparatus may be configured to change from automatic mode to manual mode when the SpO2 of the patient is not within an acceptable patient range. In some instances, the flow therapy apparatus reverts to manual mode when the SpO2 of the patient is outside of the patient limits (above or below) or if the patient's SpO2 did not move within the limits within a defined period of time after the start of the therapy session. The flow therapy apparatus may revert to manual mode when the signal quality of the patient sensor is below a threshold level for a defined period of time. In some configurations, the flow therapy apparatus may trigger an alarm when it switches from automatic mode to manual mode. In some configurations, the flow therapy apparatus may trigger an alarm when the signal quality of the patient sensor is below a threshold level for a defined period of time. The flow therapy apparatus may continue to function in automatic mode after the alarm is triggered. The flow therapy apparatus may provide the user, through a graphical user interface, with an option to disable the alarm or to exit automatic mode.

In automatic mode, the controller may utilize two control loops. The first control loop can determine a target FdO2 based on the target SpO2. The second control loop can use the target FdO2 output by the first control loop and measured FdO2 to output an oxygen inlet valve control signal. In manual mode the controller may only use the second the control loop, the second control loop can receive a target FdO2 output from user input or a default value.

During a high flow therapy session, the oxygen concentration measured in the device, fraction of delivered oxygen (FdO2), can be substantially the same as the oxygen concentration the user is breathing, fraction of inspired oxygen (FiO2), when the flow rate of gas delivered meets or exceeds the peak inspiratory demand of the patient. This means that the volume of gas delivered by the device to the patient during inspiration meets, or is in excess of, the volume of gas inspired by the patient during inspiration. High flow therapy helps to prevent entrainment of ambient air when the patient breathes in, as well as flushing the patient's airways of expired gas. So long as the flow rate of delivered gas meets or exceeds peak inspiratory demand of the patient, entrainment of ambient air is prevented and the gas delivered by the device, FdO2, is substantially the same as the gas the patient breathes in, FiO2.

Flow Therapy Apparatus

A flow therapy apparatus 10 is shown in FIG. 1A. The apparatus 10 can comprise a main housing 100 that contains a flow generator 11 in the form of a motor/impeller arrangement (for example, a blower), an optional humidifier 12, a controller 13, and a user interface 14 (comprising, for example, a display and input device(s) such as button(s), a touch screen, or the like). The controller 13 can be configured or programmed to control the operation of the apparatus. For example, the controller can control components of the apparatus, including but not limited to: operating the flow generator 11 to create a flow of gas (gases flow) for delivery to a patient, operating the humidifier 12 (if present) to humidify and/or heat the generated gases flow, control a flow of oxygen into the flow generator blower, receiving user input from the user interface 14 for reconfiguration and/or user-defined operation of the apparatus 10, and outputting information (for example on the display) to the user. The user can be a patient, healthcare professional, or anyone else interested in using the apparatus. As used herein, a "gases flow" can refer to any flow of gases that may be used in the breathing assistance or respiratory device, such as a flow of ambient air, a flow comprising substantially 100% oxygen, a flow comprising some combination of ambient air and oxygen, and/or the like.

A patient breathing conduit 16 is coupled at one end to a gases flow outlet 21 in the housing 100 of the flow therapy apparatus 10. The patient breathing conduit 16 is coupled at another end to a patient interface 17 such as a non-sealed nasal cannula with a manifold 19 and nasal prongs 18. Additionally, or alternatively, the patient breathing conduit 16 can be coupled to a face mask, a nasal mask, a nasal pillows mask, an endotracheal tube, a tracheostomy interface, and/or the like. The gases flow that is generated by the flow therapy apparatus 10 may be humidified, and delivered to the patient via the patient conduit 16 through the cannula 17. The patient conduit 16 can have a heater wire 16a to heat gases flow passing through to the patient. The heater wire 16a can be under the control of the controller 13. The patient conduit 16 and/or patient interface 17 can be considered part of the flow therapy apparatus 10, or alternatively peripheral to it. The flow therapy apparatus 10, breathing conduit 16, and patient interface 17 together can form a flow therapy system.

The controller 13 can control the flow generator 11 to generate a gases flow of the desired flow rate. The controller 13 can also control a supplemental oxygen inlet to allow for delivery of supplemental oxygen, the humidifier 12 (if present) can humidify the gases flow and/or heat the gases flow to an appropriate level, and/or the like. The gases flow is directed out through the patient conduit 16 and cannula 17 to the patient. The controller 13 can also control a heating element in the humidifier 12 and/or the heating element 16a in the patient conduit 16 to heat the gas to a desired temperature for a desired level of therapy and/or level of comfort for the patient. The controller 13 can be programmed with or can determine a suitable target temperature of the gases flow.

The oxygen inlet port 28 can include a valve through which a pressurized gas may enter the flow generator or blower. The valve can control a flow of oxygen into the flow generator blower. The valve can be any type of valve, including a proportional valve or a binary valve. The source of oxygen can be an oxygen tank or a hospital oxygen supply. Medical grade oxygen is typically between 95% and 100% purity. Oxygen sources of lower purity can also be used. Examples of valve modules and filters are disclosed in U.S. Provisional Application No. 62/409,543, titled "Valve Modules and Filter", filed on Oct. 18, 2016, and U.S. Provisional Application No. 62/488,841, titled "Valve Modules and Filter", filed on Apr. 23, 2017, which are hereby incorporated by reference in their entireties. Valve modules and filters are discussed in further detail below with relation to FIGS. 17-25.

The flow therapy apparatus 10 can measure and control the oxygen content of the gas being delivered to the patient, and therefore the oxygen content of the gas inspired by the patient. During high flow therapy, the high flow rate of gas delivered meets or exceeds the peak inspiratory demand of the patient. This means that the volume of gas delivered by the device to the patient during inspiration meets, or is in excess of, the volume of gas inspired by the patient during inspiration. High flow therapy therefore helps to prevent entrainment of ambient air when the patient breathes in, as well as flushing the patient's airways of expired gas. So long as the flow rate of delivered gas meets or exceeds peak inspiratory demand of the patient, entrainment of ambient air is prevented, and the gas delivered by the device is substantially the same as the gas the patient breathes in. As such, the oxygen concentration measured in the device, fraction of delivered oxygen, (FdO2) would be substantially the same as the oxygen concentration the user is breathing, fraction of inspired oxygen (FiO2), and as such the terms may can be seen as equivalent.

Operation sensors 3a, 3b, 3c, such as flow, temperature, humidity, and/or pressure sensors can be placed in various locations in the flow therapy apparatus 10. Additional sensors (for example, sensors 20, 25) may be placed in various locations on the patient conduit 16 and/or cannula 17 (for example, there may be a temperature sensor 29 at or near the end of the inspiratory tube). Output from the sensors can be received by the controller 13, to assist the controller in operating the flow therapy apparatus 10 in a manner that provides suitable therapy. In some configurations, providing suitable therapy includes meeting a patient's peak inspiratory demand. The apparatus 10 may have a transmitter and/or receiver 15 to enable the controller 13 to receive signals 8 from the sensors and/or to control the various components of the flow therapy apparatus 10, including but not limited to the flow generator 11, humidifier 12, and heater wire 16a, or accessories or peripherals associated with the flow therapy apparatus 10. Additionally, or alternatively, the transmitter and/or receiver 15 may deliver data to a remote server or enable remote control of the apparatus 10.

Oxygen may be measured by placing one or more gas composition sensors (such as an ultrasonic transducer system, also referred to as an ultrasonic sensor system) after the oxygen and ambient air have finished mixing. The measurement can be taken within the device, the delivery conduit, the patient interface, or at any other suitable location.

Oxygen concentration may also be measured by using flow rate sensors on at least two of the ambient air inlet conduit, the oxygen inlet conduit, and the final delivery conduit to determine the flow rate of at least two gases. By determining the flow rate of both inlet gases or one inlet gas and one total flow rate, along with the assumed or measured oxygen concentrations of the inlet gases (about 20.9% for ambient air, about 100% for oxygen), the oxygen concentration of the final gas composition can be calculated. Alternatively, flow rate sensors can be placed at all three of the ambient air inlet conduit, the oxygen inlet conduit, and the final delivery conduit to allow for redundancy and testing that each sensor is working correctly by checking for consistency of readings. Other methods of measuring the oxygen concentration delivered by the flow therapy apparatus 10 can also be used.

The flow therapy apparatus 10 can include a patient sensor 26, such as a pulse oximeter or a patient monitoring system, to measure one or more physiological parameters of the patient, such as a patient's blood oxygen saturation (SpO2), heart rate, respiratory rate, perfusion index, and provide a measure of signal quality. The sensor 26 can communicate with the controller 13 through a wired connection or by communication through a wireless transmitter on the sensor 26. The sensor 26 may be a disposable adhesive sensor designed to be connected to a patient's finger. The sensor 26 may be a non-disposable sensor. Sensors are available that are designed for different age groups and to be connected to different locations on the patient, which can be used with the flow therapy apparatus. The pulse oximeter would be attached to the user, typically at their finger, although other places such as an earlobe are also an option. The pulse oximeter would be connected to a processor in the device and would constantly provide signals indicative of the patient's blood oxygen saturation. The patient sensor 26 can be a hot swappable device, which can be attached or interchanged during operation of the flow therapy apparatus 10. For example, the patient sensor 26 may connect to the flow therapy apparatus 10 using a USB interface or using wireless communication protocols (such as, for example, near field communication, WiFi or Bluetooth®). When the patient sensor 26 is disconnected during operation, the flow therapy apparatus 10 may continue to operate in its previous state of operation for a defined time period. After the defined time period, the flow therapy apparatus 10 may trigger an alarm, transition from automatic mode to manual mode, and/or exit control mode (e.g., automatic mode or manual mode) entirely. The patient sensor 26 may be a bedside monitoring system or other patient monitoring system that communicates with the flow therapy apparatus 10 through a physical or wireless interface.

The flow therapy apparatus 10 may comprise a high flow therapy apparatus. As used herein, "high flow" therapy refers to administration of gas to the airways of a patient at a relatively high flow rate that meets or exceeds the peak inspiratory demand of the patient. The flow rates used to achieve "high flow" may be any of the flow rates listed below. For example, in some configurations, for an adult patient 'high flow therapy' may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between 25 LPM and 75 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may deliver gases to the patient at a flow rate of between about 1 LPM and about 100 LPM, or at a flow rate in any of the sub-ranges outlined above. The flow therapy apparatus 10 can deliver any concentration of oxygen (e.g., FdO2), up to 100%, at any flowrate between about 1 LPM and about 100 LPM. In some configurations, any of the flowrates can be in combination with oxygen concentrations (FdO2s) of about 20%-30%, 21%-30%, 21%-40%, 30%-40%, 40%-50%, 50%-60%, 60%-70%, 70%-80%, 80%-90%, and 90%-100%. In some combinations, the flow rate can be between about 25 LPM and 75 LPM in combination with an oxygen concentration (FdO2) of about 20%-30%, 21%-30%, 21%-40%, 30%-40%, 40%-50%, 50%-60%, 60%-70%, 70%-80%, 80%-90%, and 90%-100%. In some configurations, the flow therapy apparatus 10 may include safety thresholds when operating in manual mode that prevent a user from delivering to much oxygen to the patient.

High flow therapy may be administered to the nares of a user and/or orally, or via a tracheostomy interface. High flow therapy may deliver gases to a user at a flow rate at or exceeding the intended user's peak inspiratory flow requirements. The high flow therapy may generate a flushing effect in the nasopharynx such that the anatomical dead space of the upper airways is flushed by the high incoming gases flow. This can create a reservoir of fresh gas available for each and every breath, while minimizing re-breathing of nitrogen and carbon dioxide. Meeting inspiratory demand and flushing the airways is additionally important when trying to control the patient's FdO2. High flow therapy can be delivered with a non-sealing patient interface such as, for example, a nasal cannula. The nasal cannula may be configured to deliver breathing gases to the nares of a user at a flow rate exceeding the intended user's peak inspiratory flow requirements.

The term "non-sealing patient interface" as used herein can refer to an interface providing a pneumatic link between an airway of a patient and a gases flow source (such as from flow generator 11) that does not completely occlude the airway of the patient. Non-sealed pneumatic link can comprise an occlusion of less than about 95% of the airway of the patient. The non-sealed pneumatic link can comprise an occlusion of less than about 90% of the airway of the patient. The non-sealed pneumatic link can comprise an occlusion of between about 40% and about 80% of the airway of the patient. The airway can include one or more of a nare or mouth of the patient. For a nasal cannula the airway is through the nares.

The flow generator or blower 11 can include an ambient air inlet port 27 to entrain ambient room air into the blower. The flow therapy apparatus 10 may also include an oxygen inlet port 28 leading to a valve through which a pressurized gas may enter the flow generator or blower 11. The valve can control a flow of oxygen into the flow generator blower 11. The valve can be any type of valve, including a proportional valve or a binary valve.

The blower can operate at a motor speed of greater than about 1,000 RPM and less than about 30,000 RPM, greater than about 2,000 RPM and less than about 21,000 RPM, or between any of the foregoing values. Operation of the blower can mix the gases entering the blower through the inlet ports. Using the blower as the mixer can decrease the pressure drop that would otherwise occur in a system with a separate mixer, such as a static mixer comprising baffles, because mixing requires energy.

Figure 1B:
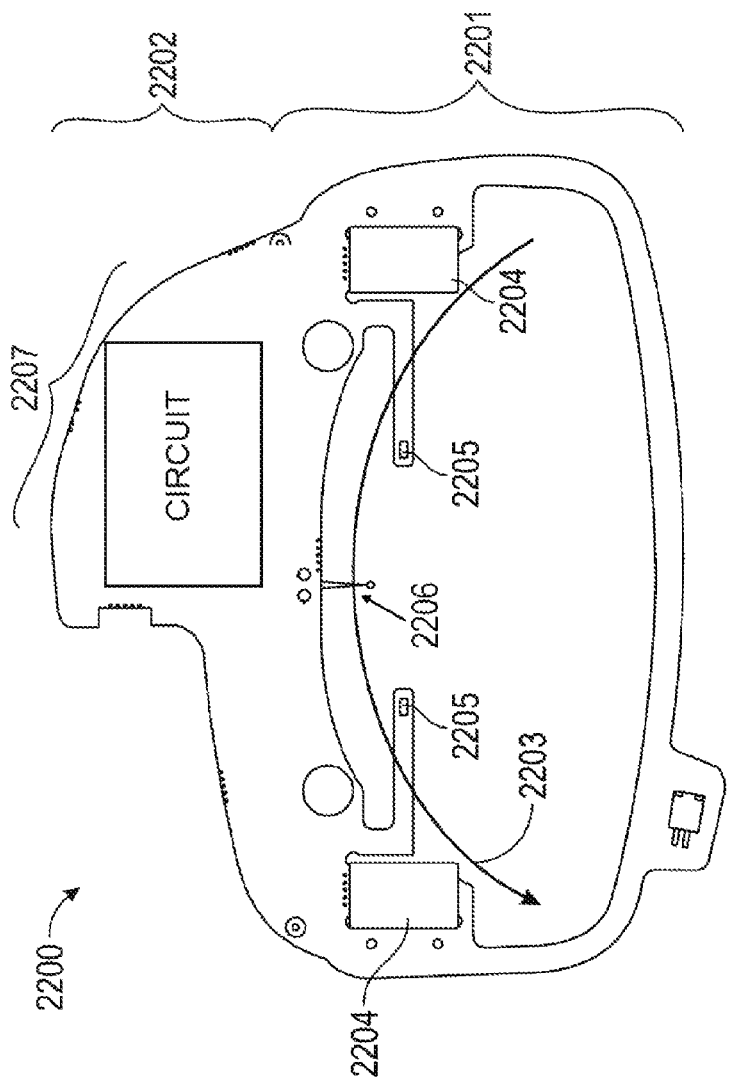
FIG. 1B illustrates a sensing circuit board including a flow rate sensor that may be used in a flow therapy apparatus.

With additional reference to FIG. 1B, a sensing circuit board 2200 is shown that can be implemented in the flow therapy apparatus 10. The sensing circuit board 2200 can be positioned in a sensor chamber such that the sensing circuit board 2200 is at least partially immersed in the flow of gases. The flow of gases may exit the blower 11 through a conduit and enter a flow path in the sensor chamber. At least some of the sensors on the sensing circuit board 2200 can be positioned within the flow of gases to measure gas properties within the flow. After passing through the flow path in the sensor chamber, the gases can exit to the humidifier 12 described above.

The sensing circuit board 2200 can be a printed sensing circuit board (PCB). Alternatively, the circuit on the board 2200 can be built with electrical wires connecting the electronic components instead of being printed on a circuit board. At least a portion of the sensing circuit board 2200 can be mounted outside of a flow of gases. The flow of gases can be generated by the flow generator 11 described above. The sensing circuit board 2200 can comprise ultrasonic transducers 2204. The sensing circuit board 2200 can comprise one or more of thermistors 2205. The thermistors 2205 can be configured to measure a temperature of the gases flow. The sensing circuit board 2200 can comprise a thermistor flow rate sensor 2206. The sensing circuit board 2200 can comprise other types of sensors, such as humidity sensors including humidity only sensors to be used with a separate temperature sensor and combined humidity and temperature sensors, sensors for measuring barometric pressure, sensors for measuring differential pressure, and/or sensors for measuring gauge pressure. The thermistor flow rate sensor 2206 can comprise hot wire anemometer, such as a platinum wire, and/or a thermistor, such as a negative temperature coefficient (NTC) or positive temperature coefficient (PTC) thermistor. Other non-limiting examples of the heated temperature sensing element include glass or epoxy-encapsulated or non-encapsulated thermistors. The thermistor flow rate sensor 2206 can be configured to measure flow rate of the gases by being supplied with a constant power, or be maintained at a constant sensor temperature or a constant temperature difference between the sensor and the flow of gases.

The sensing circuit board 2200 can comprise a first portion 2201 and a second portion 2202. The first portion 2201 can be positioned to be within the flow path of the gases, whereas the second portion 2202 can be positioned to be outside the flow path of the gases. The direction of the flow of gases is indicated in FIG. 1B by the arrow 2203. The direction of the flow of gases can be a straight line, or curved in shown in FIG. 1B.

Positioning the one or more of thermistors 2205 and/or the thermistor flow rate sensor 2206 downstream of the combined blower and mixer can take into account heat supplied to the gases flow from the blower. Also, immersing the temperature-based flow rate sensors in the flow path can increase the accuracy of measurements because the sensors being immersed in the flow can more likely to be subject to the same conditions, such as temperature, as the gases flow and therefore provide a better representation of the gases characteristics.

The sensing circuit board 2200 can comprise ultrasonic transducers, transceivers, or sensors of the sensing circuit board to measure gases properties of the gases flow, such as gas composition or concentration of one or more gases within the gases stream. Any suitable transducer, transceiver, or sensor may be mounted to the sensing circuit board 2200 as will be appreciated. In this configuration, the sensing circuit board includes an ultrasonic transducer system (also referred to as an ultrasonic sensor system) that employs ultrasonic or acoustic waves for determining gas concentrations. Various sensor configurations are described below with respect to FIGS. 1C-1F.

The ultrasonic transducer system may determine the relative gas concentrations of two or more gases in the gases flow. The ultrasonic transducer system may be configured to measure the oxygen fraction in the bulk gases stream flow, which consists of atmospheric air augmented with supplemental oxygen, which is essentially a binary gas mixture of nitrogen (N2) and oxygen (O2). It will also be appreciated that the ultrasonic transducer system may be configured to measure the gas concentrations of other augmentation gases that have blended with atmospheric air in the gases stream, including nitrogen (N2) and carbon dioxide (CO2). The ultrasonic transducers can determine the gas concentration of gases in the gases flow at a relatively high frequency. For example, the ultrasonic transducers can output a measured FdO2 value at a maximum sample rate of the sensors or at a lower frequency than the maximum sample rate, such as between about 1 Hz and 200 Hz, about 1 Hz and 100 Hz, about 1 Hz and 50 Hz, and about 1 Hz and 25 Hz.

In some configurations, sensing circuit board 2200 includes a pair of ultrasonic transducers that are provided on opposite sides of the sensing circuit board. Various alternative configurations of the ultrasonic transducers can be used for sensing the characteristics of the gases stream by the transmission and reception of ultrasonic beams or pulses.

The distance between the ultrasonic transducers 2204 on opposite ends of the sensing circuit board 2200 can affect measurement resolution. An increased distance between each of the ultrasonic transducers 2204 can reduce the proportional or fractional error, since in general a measured length will have a certain amount of error, and if the length is increased, the proportion of error generated during measurement is less than for a shorter length. Thus, the overall uncertainty of the measurement decreases. An increased distance can also increase measurement resolution and accuracy, since it allows for a longer time period for acoustic signals between the ultrasonic transducers 2204. However, an increased distance can lead to a weaker signal.

The ultrasonic transducers 2204 can be positioned such that the space between the ultrasonic transducers 2204 at least partially coincides with the flow path. In some configurations, the ultrasonic transducers are positioned on opposing ends of the sensing circuit board. Because the whole face of the flow path is exposed to the acoustic path, the sound waves propagate through all of the gases in the flow path. Averaging of the waves can occur across the entire flow path rather than a section of the flow path. Averaging over a longer distance reduces error and reduces the dependence of air-oxygen mixing. The ultrasonic transducers can be configured to measure the gases characteristics from any angle relative to the flow path.

Positioning sensors in the flow path or module, instead of outside the flow path or module, allows the transducers 2204 to both operate within a smaller temperature range relative to one another, or both substantially at one temperature (namely, the temperature of the gas flow). Having them at a substantially homogenous temperature increases accuracy as the transducers are sensitive to temperature. Further, positioning sensors along the flow path allows for measurements and calculations that account for the influence of the gas velocity so that the effect of gas velocity can be removed from the sensor measurement.

The ultrasonic transducer system is configured as an ultrasound binary gas sensing system. Binary gas analysis using ultrasound is based on sensing the speed of an acoustic pulse through the gas sample, which in this case is the bulk or primary flow of the gases stream flowing through sensing passage of the sensor housing. The speed of sound is a function of gas mean molecular weight and temperature. The system can receive a sensor signal indicative of the temperature of the gases flowing between the beam path between ultrasonic transducers. With knowledge of sensed speed of sound and sensed temperature, the gas composition in the gases stream may be determined or calculated. In particular, measurements of the speed of sound across the sensing passage may be used to infer the ratios of two known gases by reference to empirical relationships, standard algorithms, or data stored in the form of look-up tables, as is known in the art of binary gas analysis with ultrasound. It will be appreciated that alternatively an estimate of the temperature of the gases stream in the beam path of the ultrasound transducers may be used in the binary gas analysis calculations if a temperature sensor is not employed. In such alternative embodiments, the temperature of the gases stream may be conditioned or controlled to within a narrow temperature band to enable an estimate of temperature of the gases stream in the beam path to be used.

In some configurations, the flow therapy apparatus may also be provided with a humidity sensor that is located in the flow path and which is configured to generate a humidity signal indicative of the humidity of the gases stream flowing through the sensor assembly. In such embodiments, the gas composition may be determined by the sensed speed of sound, and the sensed temperature and/or sensed humidity. The humidity sensor may be a relative humidity sensor or an absolute humidity sensor. In some embodiments, the gas composition may be determined based on the sensed speed of sound and the sensed humidity, without the need for a temperature sensor.

The ultrasonic transducer system may be used to measure respective ratios of any two known gases in a gas composition. The ultrasonic transducer system can determine the relative gas concentration in a mixture of air blended with supplementary oxygen, which is substantially equivalent to a nitrogen/oxygen mixture. In such a binary gas mixture, by monitoring the speed of sound and taking the temperature into account, the mean molecular weight of the gas can be determined, and thus, the relative concentrations of the two gases may be determined. From this ratio, the oxygen fraction or nitrogen fraction of the gases stream may be extracted.

Referring to FIGS. 1C-1F, various configurations of the ultrasonic transducers will be described for the gas composition sensing system for sensing the speed of sound through the gases stream by the transmission and reception of ultrasonic beams or pulses. Like reference numerals, represent like components.

Figure 1E:
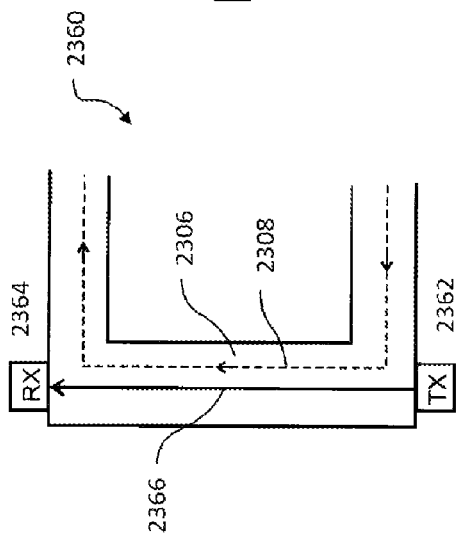
FIGS. 1E-1F illustrate schematic diagrams of various ultrasonic transducer configurations for the sensor system using along-flow beams.
Figure 1F:
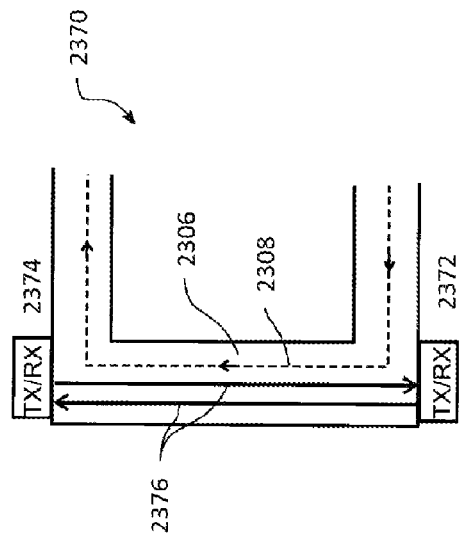
Figure 1C:
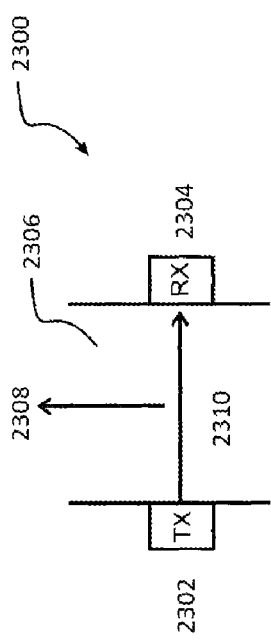
FIGS. 1C-1D illustrate schematic diagrams of various ultrasonic transducer configurations for the sensor system using cross-flow beams.

Referring to FIG. 1C, the transducer configuration 2300 provides an arrangement in which there is a pair of transducers 2302, 2304 opposing each other and positioned on opposite sides of the sensing passage 2306, with the gases flow path direction indicated generally by 2308. In this configuration, each of the transducers 2302, 2304 is driven as either a dedicated transmitter or receiver, such that ultrasonic pulses 2310 are transmitted uni-directionally across the gases flow path from the transmitter to the receiver transducer. As shown, the transducer pair is aligned (i.e. not-displaced upstream or downstream from each other) relative to the air flow path direction 2308 and is configured to transmit cross-flow pulses that are substantially perpendicular to the gases flow path direction.

Figure 1D:
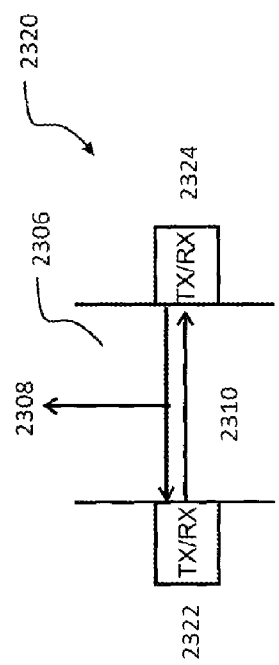

Referring to FIG. 1D, an alternative transducer configuration 2320 is illustrated in which a pair of transducers 2322, 2324 is provided opposing each other on opposite sides of the sensing passage, but wherein each transducer may operate as both a transmitter and receiver (i.e., the transducer is an ultrasonic transmitter-receiver or transceiver). In this configuration, bi-directional ultrasonic pulses 2326 may be sent between the transducer pair 2322, 2324. For example, pulses may be sent back and forth alternately between the transducers or in any other sequence or pattern. Again, the transducer pair is aligned relative to the gases flow path direction and are configured to transmit cross-flow pulses that are substantially perpendicular to the gases flow path direction.

Referring to FIG. 1E, an alternative transducer configuration 2360 is illustrated in which there is a pair of transducers 2362, 2364 opposing each other from opposite ends of the sensing passage 2306, with the gases flow path direction or axis indicated generally by 2308. In this configuration 2360, each of the transducers 2362, 2364 is driven as either a dedicated transmitter or receiver, such that along-flow ultrasonic pulses 2366 are transmitted uni-directionally in a beam path between the transmitter and receiver that is substantially aligned or parallel with the gases flow path axis 2308 in the sensing passage 2306. In the embodiment shown, the transmitter is upstream of the receiver, but it will be appreciated that the opposite arrangement could be employed. With this configuration, a flow rate sensor is provided in the sensing passage to provide a flow rate signal indicative of the flow rate of the gases stream in the sensing passage. It will be appreciated that the speed of sound in the sensing passage can be derived or determined in a similar manner to that previously described, and that the flow rate signal is utilized in the signal processing to remove or compensate for the gases flow rate in the calculated speed of sound signal.

Referring to FIG. 1F, an alternative transducer configuration 2370 is illustrated in which a pair of transducers 2372, 2374 is provided opposing each other from opposite ends of the sensing passage like in FIG. 1E, but wherein each transducer may operate as both a transmitter and receiver, i.e. is an ultrasonic transmitter-receiver or transceiver. In this configuration, bi-directional along-flow ultrasonic pulses 2376 may be sent between the transducer pair 2372, 2374. For example, pulses may be sent back and forth alternately between the transducers or in any other sequence or pattern. Again, the transducer pair are aligned with the gases flow path axis 2308 and are configured to transmit along-flow pulses in a beam path or paths that are substantially aligned or parallel to the gases flow path axis 2308 in the sensing passage 2306. With this configuration, a separate flow rate sensor need not necessarily be provided, as the flow rate component of the speed of sound signal can be directly derived or determined from processing of the transmitted and received acoustic pulses.

Some examples of flow therapy apparatuses are disclosed in International Application No. PCT/NZ2016/050193, titled "Flow Path Sensing for Flow Therapy Apparatus", filed on Dec. 2, 2016, and International Application No.

PCT/IB2016/053761, titled "Breathing Assistance Apparatus", filed on Jun. 24, 2016, which are hereby incorporated by reference in their entireties. Examples of configurations of flow therapy apparatuses that can be used with aspects of the present disclosure are discussed in further detail below with relation to FIGS. 11-16.

Control System

With reference again to FIG. 1A, the controller 13 can be programmed with or configured to execute a closed loop control system for controlling the operation of the flow therapy apparatus. The closed loop control system can be configured to ensure the patient's SpO2 reaches a target level and consistently remains at or near this level.

The controller 13 can receive input(s) from a user that can be used by the controller 13 to execute the closed loop control system. The target SpO2 value can be a single value or a range of values. The value(s) could be pre-set, chosen by a clinician, or determined based on the type of patient, where type of patient could refer to current affliction, and/or information about the patient such as age, weight, height, gender, and other patient characteristics. Similarly, the target SpO2 could be two values, each selected in any way described above. The two values would represent a range of acceptable values for the patient's SpO2. The controller can target a value within said range. The targeted value could be the middle value of the range, or any other value within the range, which could be pre-set or selected by a user. Alternatively, the range could be automatically set based on the targeted value of SpO2. The controller can be configured to have one or more set responses when the patient's SpO2 value moves outside of the range. The responses may include alarming, changing to manual control of FdO2, changing the FdO2 to a specific value, and/or other responses. The controller can have one or more ranges, where one or more different responses occur as it moves outside of each range.

The graphical user interface of the flow therapy apparatus may be configured to prompt the user to input a patient type, and the SpO2 limits would be determined based on what the user selects. Additionally, the user interface may include a custom option, where the user can define the limits.

Generally, SpO2 would be controlled between about 80% and about 100%, or about 80% and about 90%, or about 88% and about 92%, or about 90% and about 99%, or about 92% and about 96%. The SpO2 could be controlled between any two suitable values from any two of the aforementioned ranges. The target SpO2 could be between about 80% and about 100%, or between about 80% and about 90%, or between about 88% and about 92%, or between about 90% and about 99%, or between about 92% and about 96%, or about 94%, or 94% or about 90%, or 90%, or about 85%, or 85%. The SpO2 target could be any value between any two suitable values from any two of the aforementioned ranges. The SpO2 target can correspond to the middle of the SpO2 for a defined range.

The FdO2 can be configured to be controlled within a range. As discussed previously, the oxygen concentration measured in the apparatus (FdO2) would be substantially the same as the oxygen concentration the patient is breathing (FiO2) so long as the flow rate meets or exceeds the peak inspiratory demand of the patient, and as such the terms may can be seen as equivalent. Each of the limits of the range could be pre-set, selected by a user, or determined based on the type of patient, where the type of patient could refer to current affliction, and/or information about the patient such as age, weight, height, gender, and/or other patient characteristic. Alternatively, a single value for FdO2 could be selected, and the range could be determined at least partially based on this value. For example, the range could be a set amount above and below the selected FdO2. The selected FdO2 could be used as the starting point for the controller. The system could have one or more responses if the controller tries to move the FdO2 outside of the range. These responses could include alarming, preventing the FdO2 moving outside of the range, switching to manual control of FdO2, and/or switching to a specific FdO2. The device could have one or more ranges where one or more different responses occur as it reaches the limit of each range.

FdO2 can be controlled between about 21% and about 100%, or about 21% and about 90%, or about 21% and about 80%, or about 21% and about 70%, or about 21% and about 60%, or about 21% and about 50%, or about 25% and about 45%. The FdO2 could be controlled between any two suitable values from any two ranges described. The FdO2 target could be between any two suitable values from any two ranges described. If the range is based on the single value, the upper and lower limits could be decided by adding/subtracting a fixed amount from the selected value. The amount added or subtracted could be about 1%, or about 5%, or 10%, or about 15%, or about 20%, or about 30%, or about 50%, or about 100%. The amount added/subtracted could change relative to the selected value. For example, the upper limit could be 20% higher than the selected value, so a selected value of 50% FdO2 would have an upper limit of 60% for the range of control. The percentage used for the range could be about 1%, or about 5%, or 10%, or about 15%, or about 20%, or about 30%, or about 50%, or about 100%. The method for calculating the lower limit and the upper would not necessarily need to be the same. If a single value is used, the value could be between about 21% and about 100%, or about 25% and about 90%, or about 25% and about 80%, or about 25% and about 70%, or about 25% and about 60%, or about 25% and about 50%, or about 25% and about 45%.

The graphical user interface 14 (GUI) can be configured to display the range of values between which FdO2 and/or SpO2 are being controlled. The range could be displayed by having the two limits set apart from each other on the GUI, with an indicator appearing within the range to graphically represent the position of the current value with respect to the limits of the range.

The GUI can display graphs of recent FdO2 and/or SpO2 data. The GUI can display the level of each parameter on the same or different graphs over a defined period of time, such as one or more hours. The length of time over which data is displayed could match the length of the time for which data is currently available.

FdO2 data displayed can be at least one of the target FdO2 or the measured FdO2. The SpO2 data can include a line indicating target SpO2. Additionally, or alternatively, SpO2 and/or FdO2 data can include one or more lines or shaded areas indicating their respective control limits.

The graphs can be displayed on the default display. Alternatively, the graphs can be hidden with only current data values being shown. The graph can become available through interaction with the GUI, such as by selecting to view a graph for a defined parameter.

Closed Loop Control

Figure 10:
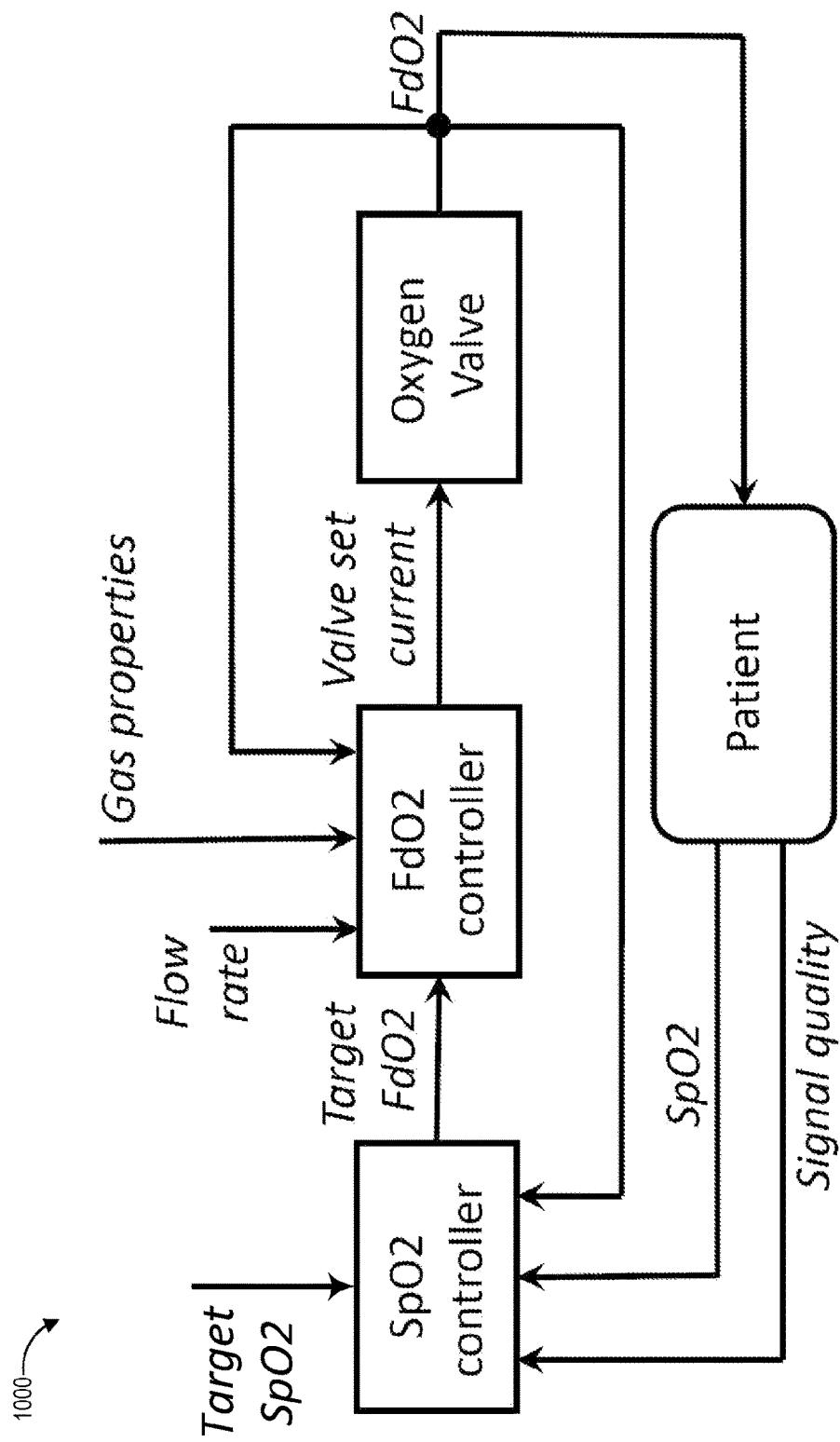
FIG. 10 is a schematic diagram of a closed loop control system.

With reference to FIG. 10 a schematic diagram of the closed loop control system 1000 is illustrated. The closed loop control system may utilize two control loops. The first control loop may be implemented by the SpO2 controller. The SpO2 controller can determine a target FdO2 based in part on the target SpO2 and/or the measured SpO2. As discussed above, the target SpO2 value can be a single value or a range of acceptable values. The value(s) could be pre-set, chosen by a clinician, or determined automatically based on client characteristics. Generally, target SpO2 values are received or determined before or at the beginning of a therapy session, though target SpO2 values may be received at any time during the therapy session. During a therapy session, the SpO2 controller can also receive as inputs: measured FdO2 reading(s) from a gases composition sensor, and measured SpO2 reading(s) and a signal quality reading(s) from the patient sensor. In some configurations, the SpO2 controller can receive target FdO2 as an input, in such a case, the output of the SpO2 controller may be provided directly back to the SpO2 controller as the input. Based at least in part on the inputs, the SpO2 controller can output a target FdO2 to the second control loop.

The second control loop may be implemented by the FdO2 controller. The FdO2 controller can receive inputs of measured FdO2 and target FdO2. The FdO2 controller can then output an oxygen inlet valve control signal to control the operation of the oxygen valve based on a difference between these measured FdO2 and target FdO2 values. The FdO2 controller may receive the target FdO2 value that is output from the first control loop when the flow therapy apparatus is operating in automatic mode. The FdO2 controller may also receive additional parameters such as flow rate values, gas properties, and/or measured FdO2. The gas properties may include the temperature of the gas at the O2 inlet and/or the oxygen content of the supply source. The gases supply source connected to the oxygen inlet valve may be an enriched oxygen gasflow where the oxygen content of the supply source may be less than pure oxygen (i.e., 100%). For example, the oxygen supply source may be an oxygen enriched gasflow having an oxygen content of less than 100% and greater than 21%.

From at least some of the inputs, the FdO2 controller can determine an oxygen flow rate that would be required to achieve the target FdO2. The FdO2 controller can use the flow rate input in order to alter the valve control signal. If the flow rate changes, the FdO2 controller can automatically calculate a new required oxygen flow rate required to maintain the target FdO2 at the new flow rate without having to wait for feedback from the gas concentration sensor, such as the measured FdO2 value. The FdO2 controller can then output the altered valve control signal to control the valve based on the new flow rate. In some configurations, the control signal of the FdO2 controller may set the current of the oxygen valve in order to control operation of the oxygen valve. Additionally, or alternatively, the FdO2 controller could detect changes to the measured FdO2 and alter the position of the valve accordingly. During manual mode, the second control loop can operate independently without receiving the target FdO2 from the first control loop. Rather, the target FdO2 can be received from user input or a default value.

During the therapy session, the SpO2 and FdO2 controllers can continue to automatically control the operation of the flow therapy apparatus until the therapy session ends or an event triggers a change from the automatic mode to manual mode.

Closed Loop Control Using Patient Model

Figure 2:
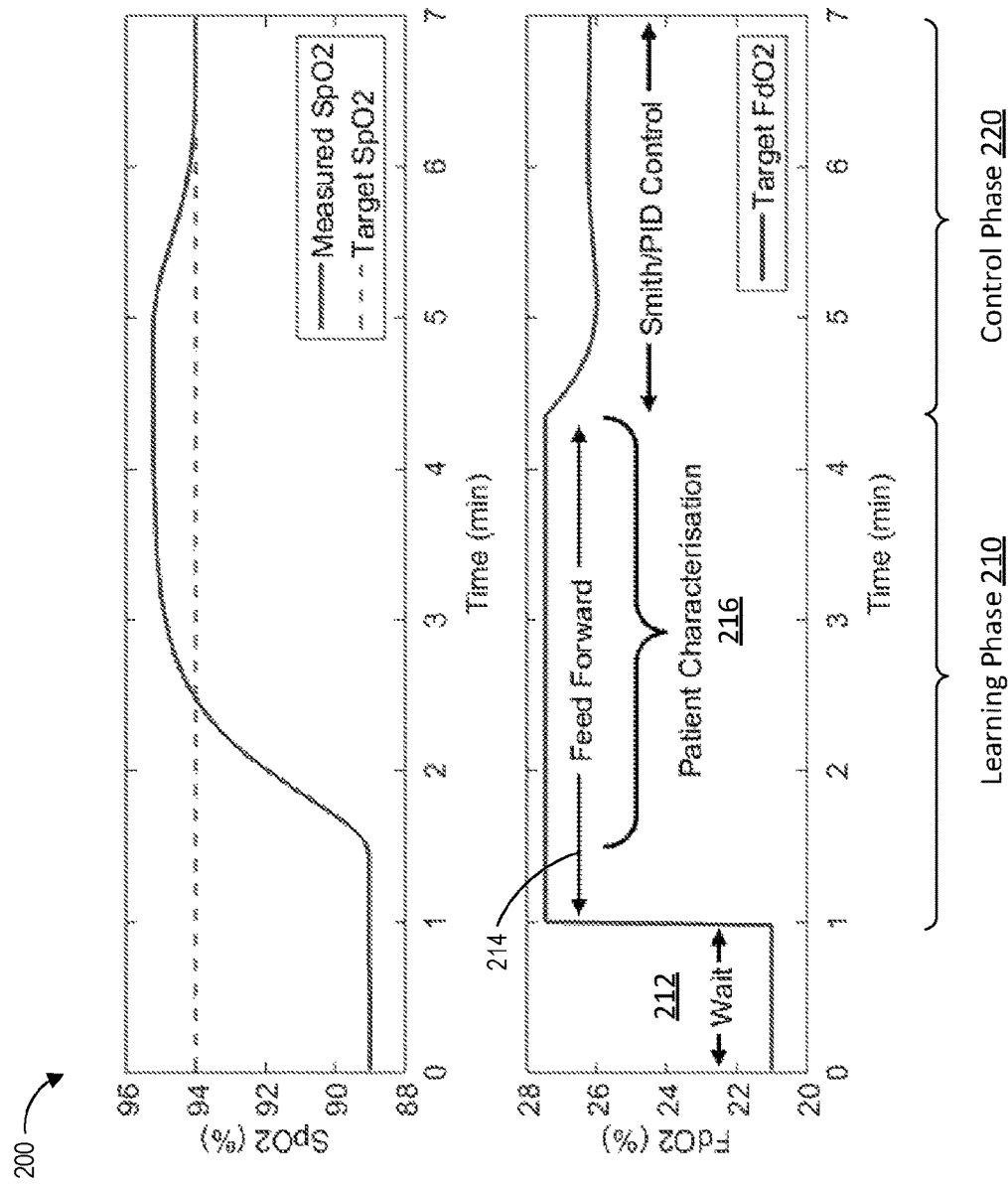
FIG. 2 illustrates graphs showing phases of operation of a flow therapy apparatus.

FIG. 2 provides graphs 200 for SpO2 and FdO2 illustrating the phases of the operation of the flow therapy apparatus during a therapy session. Although FdO2 (oxygen fraction delivered) is used in the graphs, as previously discussed earlier, the FdO2 is substantially the same as FiO2 so long as the flow rate meets or exceeds the peak inspiratory demand of the patient. The phases of operation include a learning phase 210 and a control phase 220. During the learning phase, the controller generates a patient specific model. Due to differences between individual patients, there can be variation in the way in which each patient's SpO2 responds to a change in FdO2. As a result, patient specific model can be generated to provide better control of the patient's SpO2. The learning phase 210, also referred to as a model building phase, can include a wait stage 212, a feed forward stage 214, and a model generation or patient characterization stage 216. The patient characterization stage occurs simultaneously with at least a portion of the feed forward stage 214. During the patient characterization phase, the patient specific model can be iteratively developed as data is gathered during the feed forward stage 214. The learning phase concludes after generation of the patient specific model. After the learning phase, the flow therapy apparatus operates in the control phase until the end of the therapy session. As described below, the flow therapy apparatus may be configured to transition back to the learning phase during a therapy session. In some configurations, the learning phase is optional and a patient specific model can be generated without a defined learning phase. For example, in such configurations, a default model may be used initially. The default model can then be updated during the therapy session to a patient specific model. The patient specific model may be updated at defined intervals, defined events, periodically, aperiodically, and/or continuously during a therapy session.

Learning Phase

When the flow therapy apparatus initially turns on, the flow therapy apparatus may begin in manual mode or automatic mode. If the device is in manual mode, it can be switched to automatic mode. When starting in automatic mode or when switched to automatic mode, the flow therapy apparatus may begin a therapy session after the user provides one or more operational settings (e.g., FdO2 limits, SpO2 limits, flow rate, etc.). When the session begins, the controller can initiate the wait stage 212. During the wait stage 212, the position of the oxygen inlet valve is based on the FdO2 setting prior to the initiation of the learning phase, which may result in the valve remaining in the same position or in a change to the position of the valve (e.g., opening or closing). The patient's SpO2 may change in response to the high flow therapy. The controller can wait until the SpO2 stabilizes and the SpO2 has settled at a reasonably constant value prior to proceeding to the feed forward stage 214. The wait stage 212 may last a defined period of time. The controller may be configured to initiate the feed forward stage 214 without a wait stage 212.

During the feed forward stage 214, the controller can change the level of the FdO2, such as increasing or decreasing the level. The new FdO2 value could be pre-set or determined based on factors such as the current SpO2 of the patient. The new FdO2 may be selected by a clinician, who chooses the FdO2 based on their own expertise and knowledge. The chosen FdO2 can bring the patient's SpO2 close to the target SpO2 level. The FdO2 may be determined automatically by the controller 13.

During the feed forward stage 214, the controller measures and records the patient's SpO2. The controller can measure and record the FdO2. The graph illustrates a step change in the FdO2 to the target FdO2 value. The actual FdO2 can ramp up to the target FdO2 over a defined period of time. The measured data for SpO2 and FdO2 can be incorporated in assessing the relationship between SpO2 and FdO2 and generating the model. The signal quality indicator from the patient sensor 26 can also be recorded.

The feed forward stage 214 can last for at least a defined minimum period of time, and can automatically end after a defined maximum period of time. In some configurations, the minimum period of time can be about 30 seconds, about 1 minute, about 2 minutes, 3 minutes, or another value within the aforementioned values. The maximum period of time can be about 3 minutes, about 4 minutes, about 5 minutes, about 6 minutes, or another value within the aforementioned values. The minimum and maximum values could be a combination of any two suitable values described above. After the minimum period of time, the controller can determine whether the patient has been sufficiently characterised based on an analysis of defined patient characterization criteria. If the maximum time period is reached without the patient being sufficiently characterised, then the feed forward stage would end and the control phase would be started using the default patient model. The default model may be dependent on the type of patient (e.g., normal, hypercapnic, user-defined, or other type). The default patient model may be based at least in part on one or received more characteristics of the patient. Reasons for failing to characterise the patient are discussed in further detail below.

During the feed forward stage 214, the controller may analyse the relationship between FdO2 and SpO2. The controller may be configured to model the relationship using an exponential decay function, where the exponential decay constant is varied to best fit the model to the data. Initial and final FdO2 values used in the exponential decay function can be set by the initial and final target FdO2 values. Fitting a model to the FdO2 data allows for an analytical evaluation of the SpO2 model, which can be faster and less computationally demanding. An example of how both sets of trend fitting might look is displayed in FIG. 3. Optionally, the controller may determine a relationship between the measured FdO2 and the amount of time since the change in target FdO2.

Figure 3:
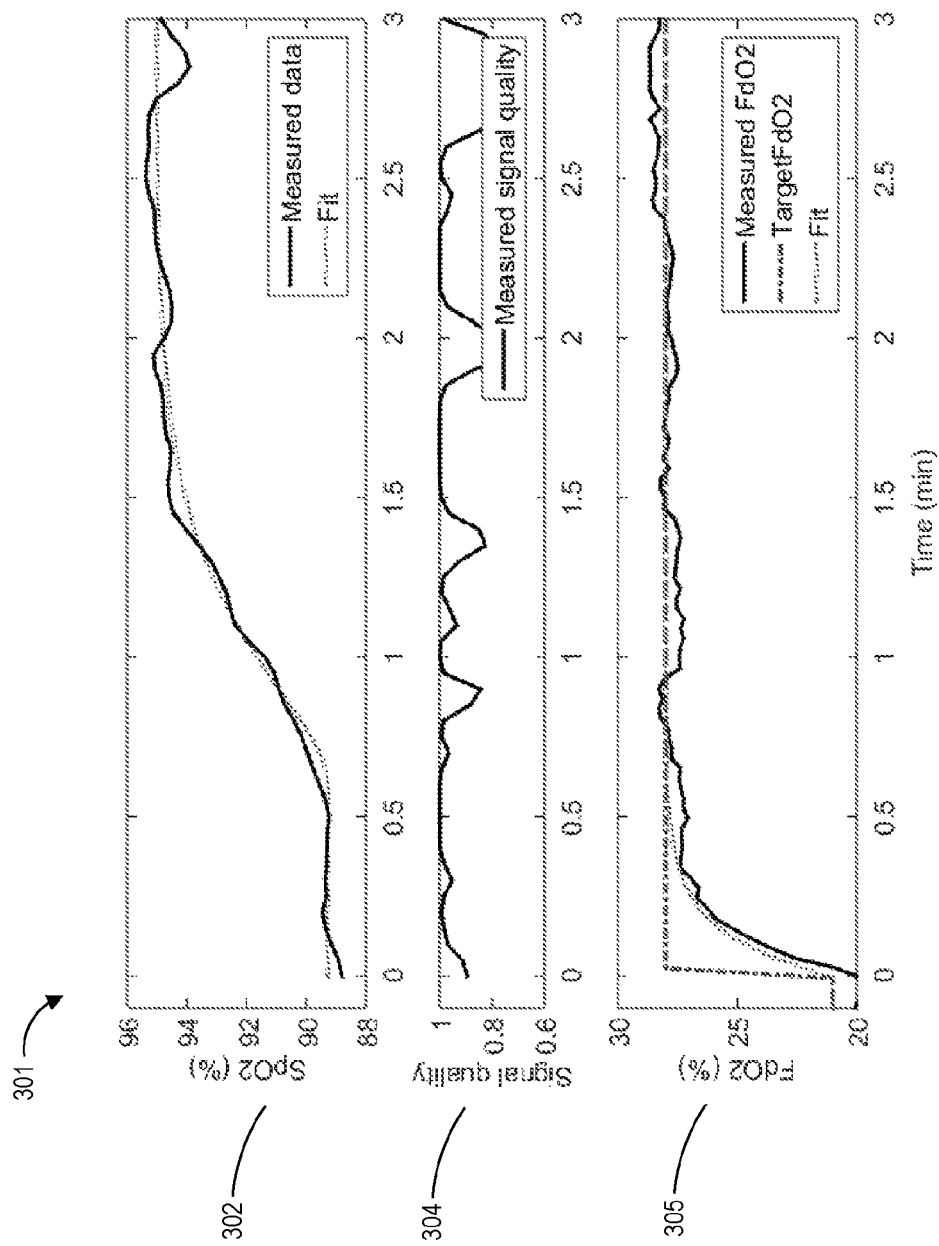
FIG. 3 illustrates graphs showing a fitted trend line for a patient model.

With additional reference to FIG. 3, graphs 301 illustrate a fitted trend for the SpO2 graph 302 and the FdO2 graph 305. The graphs also include a measure of signal quality 304 of the patient monitor. In order to fit a trend to the SpO2 data, a model that represents the SpO2 data's behaviour can be generated, and at least one constant parameter of the model determined. The model can correlate each change in FdO2 to a time based change in SpO2.

After a change in FdO2, the SpO2 does not exhibit any change due to said FdO2 change for a period of time, which can be referred to as delay time. The delay time is due to a combination of various factors. One potential factor is the time it takes for the device to change the FdO2, and would be fairly consistent. Another potential factor is the time it takes the gas to travel from the device to the interface, which can be dependent on the selected flow rate. Another potential factor is the time it takes the gases to travel from the user interface to the patient's lungs. This can be dependent on the selected flowrate, but may also be dependent on the restriction of the patient's airways and the length of the passageway from the interface to their lungs. Another potential factor is the time it takes for the oxygenated blood to travel from the patient's lungs to the measuring site (i.e. location of the patent sensor). This is dependent on the speed the blood travels, which would vary based on the patient's physiology and heart rate. Additionally, this length of time can be dependent on the distance between the patient's lungs and the type of patient sensor used. The distance could be altered by the location of the patient sensor. The distance could be additionally or alternatively altered by the size of the patient.

After the delay time, the SpO2 can exhibit an exponential decay curve, where the SpO2 asymptotically approaches a new value, where the overall change is proportional to the overall change in FdO2. In some embodiments, there are four parameters of the model that can influence its shape (in addition to the influence of the changes in FdO2 delivery). The first is the delay time between a change in FdO2 and the first change in SpO2. The second is the initial value of SpO2. The third is the magnitude of total change in SpO2 relative the magnitude in change of FdO2. The fourth is the rate of exponential decay, which defines how quickly the SpO2 approaches its final value after the delay time.

Due to the FdO2 not exhibiting a single change but instead changing over time, the SpO2 model can be evaluated as an integral of the effects of various FdO2 changes over time. A model that may be used is displayed below in equation (1).

$$M(t) = SpO2_0 + \frac{a}{\tau}\int_{-\infty}^{t-DT} \exp\left(-\frac{1}{\tau}(t - DT - t')\right)(FdO2(t') - FdO2_0)dt' \quad (1)$$

Equation (1) includes 5 parameters for the model that can be evaluated and determined when generating the model. $FdO2_0$, which is the initial FdO2, $SpO2_0$, which is the initial SpO2, DT, which is the delay time, $\tau$, which is the exponential decay constant, and a, which is the ratio between change in SpO2 and FdO2. $FdO2_0$ can be determined from the initial target FdO2. The remaining four parameters can be varied to find the model that best fits the data.

The fit may be quantified by a method known as least squares. The least squares method involves looking at each data point and calculating the error, where the error is based on the difference between said data point and a relevant point on the model. The error for each data point can be added up to give a total value of error for the model.

The model can be determined by selecting the set of parameters that result in the model having the smallest possible total error. The values for the set of parameters can be calculated using a suitable iterative method that aims to progressively get closer and closer to the ideal set of constant parameters. One algorithm is the Levenberg-Marquardt algorithm. With additional reference to FIG. 4, a graph 401 illustrating iterations of a trend line prior to arriving at the best fit 405, and a graph of signal quality 404 are illustrated.

Additionally, when calculating error, the error value for each piece of data can be weighted by the corresponding signal quality for said piece of data. Signal quality of the patient sensor is illustrated in graph 404. The weighting of the data points can give extra weight to more accurate data points when determining the constant parameters and fitting a trend line. Without weighting, the error of data points of the model could potentially be overly influenced by inaccurate data points.

The result of the learning phase can be used to tune the controller to best suit the individual patient. An untuned controller that is not specifically modeled to the individual patient can exhibit a number of drawbacks. In general, a slow/overdamped controller can take longer to reach the target SpO2 and can be slow to react to any fluctuations. On the other hand, a fast/underdamped controller runs the risk of trying to move towards the target value too quickly and overshooting it. This could lead to the controller oscillating about the target and becoming unstable. Preferably, the controller is critically damped, meaning that the model can reach the target SpO2 value quickly, but not so fast that it substantially overshoots the target and becomes unstable. By using the model generated through patient characterization an analytical solution can be found that critically damps the control algorithm.

Some of the analysis that can be performed during this learning phase is facilitated by the system utilizing nasal high flow. In other systems, such as ventilation via a mask or tracheostomy interface, the relationship between FdO2 and SpO2 is greatly affected by the respiratory rate of the patient. One reason for this is the portion of each breath that is rebreathed exhaled gas. When the patient takes short quick breaths a large portion of the breath is rebreathed gas, so the gas entering the patient's lungs is made up of a smaller portion of therapeutic gas. Likewise, when the patient takes slow deep breaths a smaller portion of the breath is rebreathed gas, so the gas entering the patient's lungs is made up of a larger portion of therapeutic gas. This affects the oxygen concentration in the patient's lungs, which in turn influences SpO2.

As described earlier, nasal high flow has the effect of flushing the patient's airways with therapeutic gas to greatly reduce rebreathing. This means that regardless of the patient's respiratory rate there will be minimal rebreathing, and the gas entering the patient's lungs will be far more similar in composition to the therapeutic gas delivered by the device.

Because of the reduced effect of respiratory rate on the FdO2/SpO2 relationship, the device is able to utilize the learning phase at startup in which data analysis allows for optimal tuning of the controller and/or implementing patient specific predictive control, without the need for computationally demanding constant learning.

When the characterization criteria have been satisfied, the patient has been sufficiently characterized. After patient characterization 216 the learning phase 210 ends and the control phase 220 begins. The characterization criteria can define acceptable ranges for at least some of the parameters that are used for calculation of the patient model. For example, the characterization criteria may include a range of acceptable values for a determined delay time between a change in FdO2 and the first change in SpO2, a range of acceptable values for an initial value of SpO2, a range of acceptable values for the rate of exponential decay, which defines how quickly the SpO2 approaches its final value after the delay time, a range of acceptable values for the ratio between change in SpO2 and FdO2, and/or other parameters associated with the generation of the model. The characterization criteria may define only a minimum or maximum value for a parameter.

In some situations, the patient characterization may fail. In such situations, the controller can initiate the control phase with a default PID controller or switch back to automatically maintaining the FdO2 at a prescribed level. The default PID controller can be designed in such a way that it is critically damped or overdamped for most, if not all, patients. Generally, an overdamped controller that moves towards an SpO2 target slowly is more desirable than an underdamped controller that oscillates and becomes unstable. Each type of patient may have a different default PID controller.

Reasons for failure in the patient characterization could include problems with the data set, such as low average signal quality, too small of an FdO2 increase, and/or too small of an SpO2 increase. Additionally, or alternatively, failure could occur due to reasons associated with modelling the data, such as certain parameters falling outside of specific acceptable ranges. These parameters could include the fit/error of the model, as a high amount of error between the model and the data would reduce the validity of the model. The parameters could include the varied parameters of the model discussed earlier (initial SpO2, delay time, exponential decay constant and the ratio between FdO2 and SpO2 increase), as unrealistic values for any of these would indicate an error in the model. Additionally, or alternatively, failure could occur during the tuning of the PID if any of the tuned PID values fall outside of specific ranges.

The clinician would ideally be warned by an alarm that this had occurred, and an option may be available to try another learning phase. Additionally, or alternatively, the device could initiate another learning phase itself to attempt to characterize the patient. The number of automatic attempts could be limited to a defined number. Additionally or alternatively, the patient specific model can be generated from a default model and then optionally updated during the therapy session.

The learning phase may be repeated more than once during a therapy session. Even if the learning phase is successful, there may be conditions that arise during a therapy session that cause the controller to enter the learning phase again. The controller may have a maximum amount of time that the patient model is valid for. For example, in hospital situations, the patient's condition may be changing over time in ways that affect the relationship between FdO2 and SpO2. As such, it may be beneficial to end the control phase and/or automatically initiate a new learning phase to recharacterize the patient after a certain amount of time, such as one or more days. Additionally or alternatively, the patient specific model may be updated and recharacterized during the therapy session. For example the patient specific model may be updated at defined intervals, defined events, periodically, aperiodically, and/or continuously during a therapy session.

The controller may test the error between corresponding predicted and measured SpO2 values. A large enough error, possibly across multiple error values or a defined period of time, could indicate an incorrect patient model, and the controller may be configured to initiate a new learning phase. In some instances, if the SpO2 of the patient falls outside of the target range, the controller can end the control phase and trigger a new learning phase.

Predictive Control During Control Phase

Figure 5:
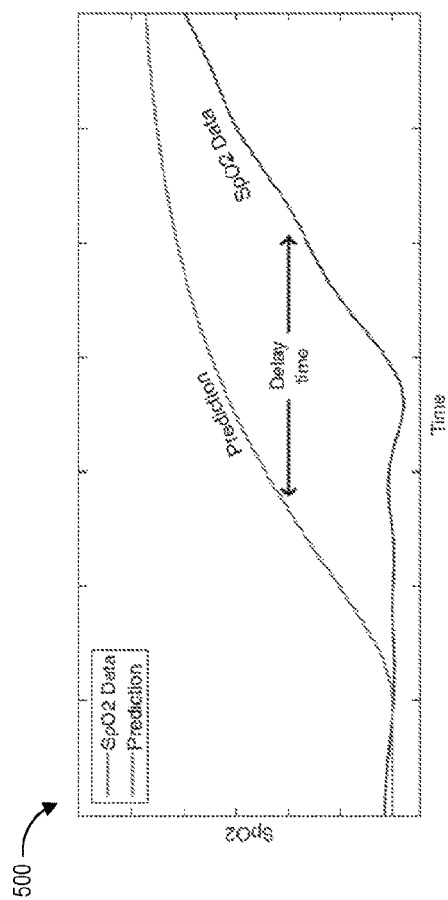
FIG. 5 illustrates a graph showing signal lag between predicted SpO2 values and actual SpO2 values.

FIG. 5 illustrates a graph 500 of signal lag between predicted SpO2 values and the SpO2 data. One of the difficulties in controlling FdO2 based on the SpO2 signal is the delay time and resulting signal lag. When the FdO2 is altered at the device, the gas with the new oxygen concentration needs to travel through the conduit to the patient interface, down the patient's airways into their lungs, and perform gas exchange in the patient's lungs. Then the oxygenated blood has to travel through their blood vessels to the pulse oximeter site, be measured by the patient sensor, and then have said measurement data received by the controller. By the time the measurement data is received by the controller, multiple additional cycles may have already been processed, resulting in a substantial overshoot of the target SpO2, which in turn can cause large oscillations in the patient's SpO2 and instability in the control. Additionally, another aspect of nasal high flow is the use of a humidifier during a therapy session. Without a humidifier, the patient's airways would rapidly dry out. The humidification components can require sufficient residence time in order to function, thereby increasing the delay time. This additional delay can make the predictor increasingly important in accounting for the delay time.

Some ways of dealing with this include overdamping the controller, having a low sensitivity, and/or by having a delay between each iteration of the control signal to allow for the previous change in FdO2 to take full effect. Such a delay could be at least partially based on data measured in the learning phase discussed earlier. While such a system may adequately deal with the signal delay, it could raise new issues due to being too slow and unreactive to the patient's condition. For example, when the device is first turned on, it would greatly increase the time it takes to arrive at the targeted SpO2 or the controller may be too slow to react to sudden changes in the patient's SpO2.

The controller can be configured to implement predictive control into the PID controller during the control phase. The predictive control may be a Smith predictor. The predictive control could be determined based at least in part on one or more parameters analyzed during the learning phase 210. Using the data received during the learning phase 210 to design or modify the predictive controller allows for far more efficient and patient specific control. The purpose of the predictive control is to predict the SpO2 value with signal lag accounted for, and control the FdO2 based on the predicted SpO2 value instead of measured SpO2. This results in a control algorithm that can be highly sensitive and stable.

The predicted value of SpO2 can represent the SpO2 after the delay time has passed. The delay time is the period of time between when a change is made to the FdO2 and a response is seen in the SpO2, i.e., when a corresponding response is detected in the measured SpO2. Because any FdO2 change will not have any effect on the SpO2 until after the delay time has passed, the SpO2 up till the end of the delay time period can be predicted fairly accurately using currently available data of the SpO2 and FdO2. The predictor can generate data substantially the same as the measured SpO2 data with the delay time removed, as illustrated in FIG. 5. While the prediction does not predict disturbances shown in the real data, the general shape of the curve is matched.

The predictor can receive inputs that include one or more measured FdO2 values, one or more target FdO2 values, one or more predicted SpO2 values, one or more measured SpO2 values and/or one or more targeted SpO2 values. Each of the inputs can be the most recent value and/or previous values that are at least temporarily stored by the processor. Each of the inputs could be paired with any relevant data associated with the input data point, such as a signal quality measurement and/or a value relating to the time at which the measurement occurred.

From here the PID controller would act substantially the same as described earlier, however the PID controller uses the estimated SpO2 in place of the measured SpO2, and as such the difference between this estimation and the target would be calculated instead. This value would represent the change in SpO2. Due to using the predictor, the change in SpO2 takes into account previous changes in FdO2 that have not taken effect yet. The change in SpO2 will be paired with the current FdO2 to determine a new target FdO2.

Figure 6:
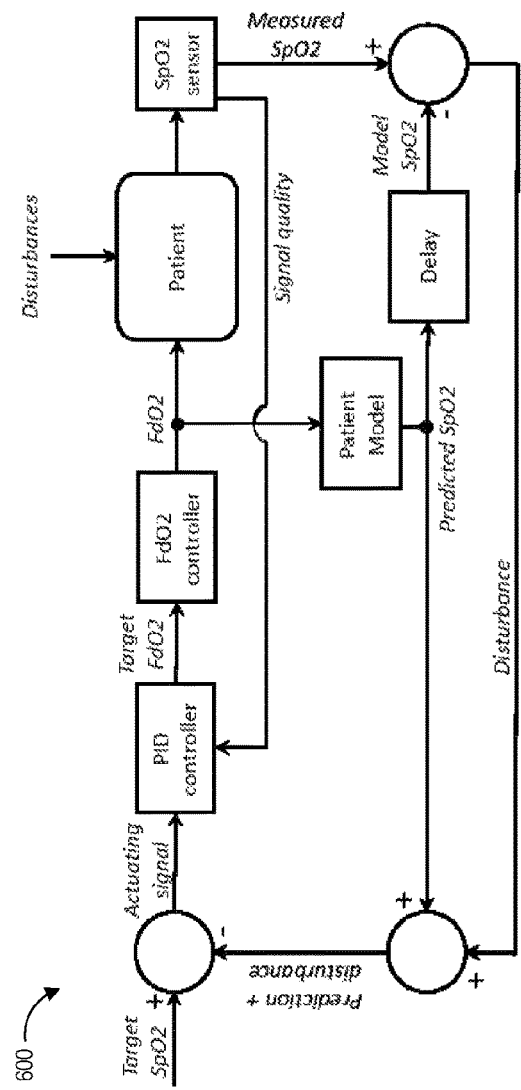
FIG. 6 illustrates a Smith predictor being utilized with the PID controller.

FIG. 6 illustrates a schematic diagram 600 of a Smith predictor being utilized with the PID controller. Initially, the PID controller receives an input of the difference between the predicted patient SpO2 and target SpO2, and outputs a target FdO2 to the FdO2 controller to bring the patient SpO2 closer to the target SpO2. The FdO2 controller outputs instructions to control the valve of the flow therapy apparatus based on the target FdO2 output by the PID controller.

This new FdO2 is delivered to the patient, and combined with other disturbances, resulting in a patient response. These disturbances can include errors from any sensors or control mechanisms in the machine (such as the oxygen valve) that result in an altered FdO2. Additional changes in the patient response could result from physiological and physical parameters with the patient (physical exertion, changed respiratory rate, etc.) that have an effect on the patient's SpO2. The SpO2 is then measured, and the value will be the patient's current SpO2, plus or minus any error from the sensor. A signal quality indication is also output to the PID controller.

For reference, in a controller with no Smith predictor, the measured SpO2 value would then be compared with the target SpO2, and the difference between the two would be fed back into the PID. With the Smith predictor model, first, the controller makes a prediction of the SpO2. This can be done using the same model generated during the learning phase or a default model (for example, when a patient cannot be, or is not, characterized), where SpO2 is estimated by integrating the effects of all FdO2 changes over time and then adding them to the initial SpO2:

$$M_{DT}(t) = SpO2_0 + \frac{a}{\tau} \int_{-\infty}^{t-DT} \exp\left(-\frac{1}{\tau}(t - DT - t')\right)(FdO2(t') - FdO2_0)dt'$$

Where DT, $SpO2_0$, a, $\tau$, $FdO2_0$ are constant parameters of the model, which may be generated during a learning phase or may begin as default values. The parameters may be unchanged throughout the therapy session or may be continuously, periodically, or aperiodically updated Importantly, DT is the delay time between the change in FdO2 and the start of the SpO2 response. In the first step, this calculation is run where DT is assumed to be 0. This results in an estimation of the patient's SpO2 after the delay time has passed. This value can be referred to as predicted SpO2 without delay time.

Following this, the same equation is processed again, using the estimated value for DT from the learning phase. The output of the model when using DT can be referred to as the predicted SpO2 with delay time, which predicts the current reading from the pulse oximeter. The predicted SpO2 with delay time can also be calculated by referring back to a previous estimation of SpO2 without delay time. For example, if the delay time was 90 seconds, the estimation of SpO2 with delay time is the estimation of SpO2 without delay time that was made 90 seconds ago.

The difference between the SpO2 without delay time value and the measured SpO2 value is then calculated. If the model is perfect, then the difference will be 0. Typically, some difference will be present, and this represents both error in the model as well as the disturbances in SpO2 mentioned earlier.

Figure 7:
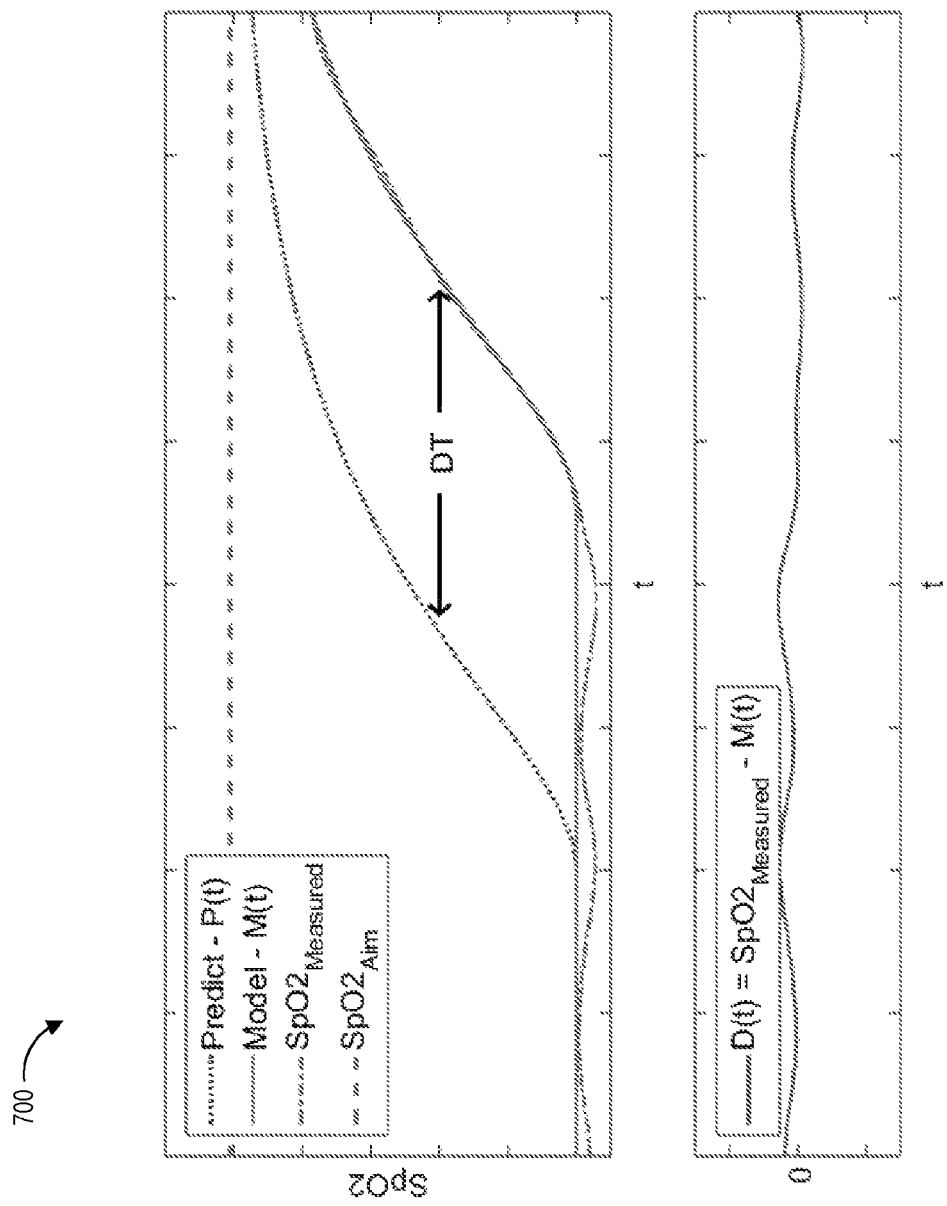
FIG. 7 illustrates a graph of predicted SpO2 values with the delay time.

FIG. 7 illustrates a graph 700 of the prediction with the delay time included. This error and disturbances value is then added to the first prediction of SpO2 without delay time, and can be used to correct the predicted SpO2 using the measured error between actual and predicted SpO2. This final value represents the predicted SpO2 without delay time plus disturbances.

The difference between the predicted SpO2 without delay time plus disturbances and the target SpO2 is then calculated, and the result is fed back into the PID controller, and the process starts again.

Assumptions may be made to reduce the computational load of modelling the SpO2 response. Firstly, because the FdO2 is changed in stepped increments with each iteration of the control cycle, the equation can be evaluated by using discrete time points. Because of this, the model can be further rearranged into an iterative process, where the result from the previous iteration of the model can be included in evaluating the current iteration of the model.

In some instances, the Smith predictor can allow the PID controller to react in anticipation of the SpO2 reading and not in reaction to it. For example, the Smith predictor might predict the SpO2 rising to and settling at the targeted level. However, when the actual SpO2 measurement comes in it may show the SpO2 has gotten closer to the target faster than it predicted, and is now heading for overshooting the target value based on the previous changes in FdO2 that had been made. As such, the controller could quickly drop the FdO2 to minimize or even prevent the overshoot from occurring. Without the Smith predictor the control system would not respond to the overshoot until it had already happened.

Figure 8:
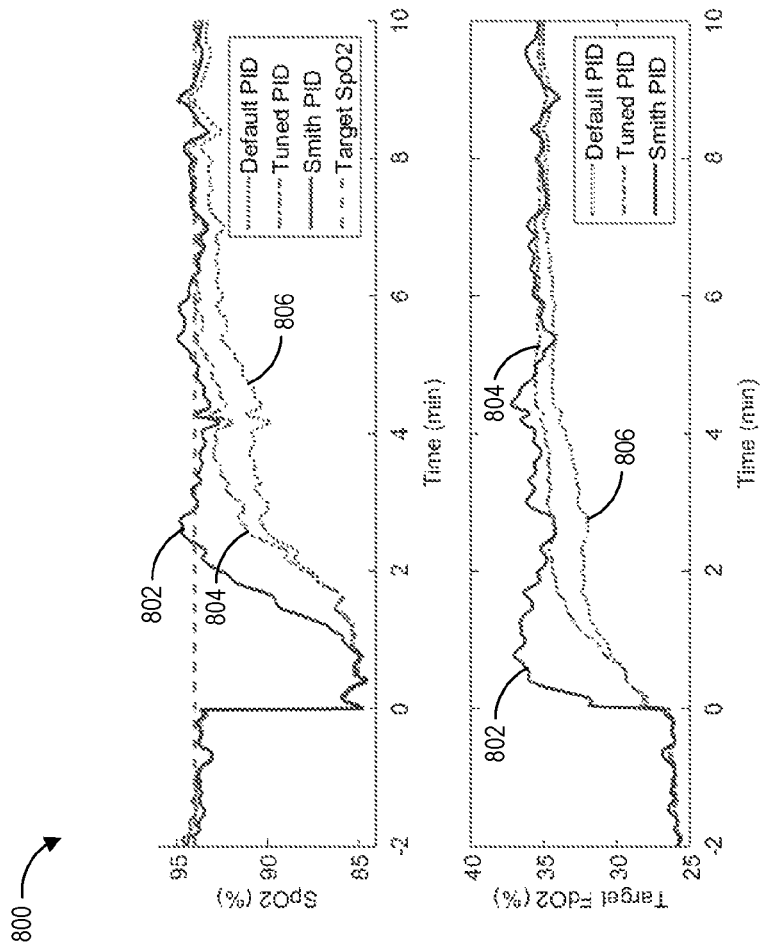
FIG. 8 illustrates graphs showing outputs of different computational models for PID controllers.

FIG. 8 illustrates different computational models for PID controllers. To demonstrate the difference a Smith predictor makes, a computational model was set up to represent a COPD patient. The model involved a sudden drop from a healthy SpO2 reading along with random fluctuations in SpO2 that would normally occur. The purpose was to see how quickly the control system could return the patient to a healthy SpO2 reading and settle at this point, as well as how well it could deal with the random fluctuations. The same model with identical random fluctuations was tested on three different PID controllers, one with a Smith predictor 802, one normal PID tuned for the specific patient 804, and one tuned for a default patient 806. A PID controller can be tuned or untuned. The untuned PID controller can be referred to as a default PID or an untuned PID. An untuned controller refers to a PID controller that has not been tuned to a specific patient. However, untuned controllers may be tuned for stability or for a general patient type or a specific patient type (e.g., normal, hypercapnic, etc.) and loaded onto the controller prior to operation of the flow therapy apparatus. Additionally, a tuned PID controller and a default PID controller can refer to a PID controller that does not incorporate a Smith predictor. A Smith predictor can be used to vary the tuned PID.

As described above, the Smith PID 802 was able to return to a healthy SpO2 reading around 4 times quicker than the default PID 806 and was more precise at maintaining the target SpO2. The tuned PID 804 was better than the default PID 806 but not quite as good as the Smith PID 802.

Signal Weighting

Figure 4:
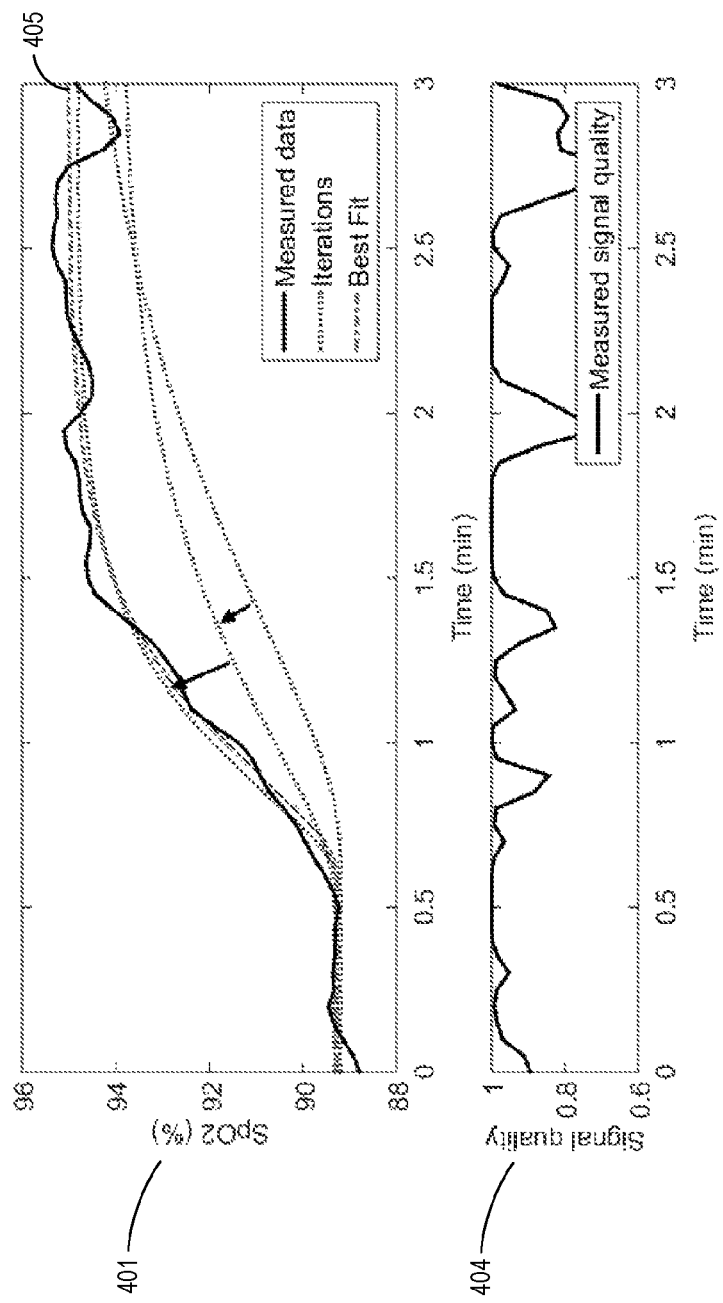
FIG. 4 illustrates a graph showing iterations of a trend line for a patient model.

With reference to FIGS. 3 and 4, graphs 304 and 404 provide a signal quality indicator of the patient sensor. During use, the quality of the SpO2 signal from the patient sensor can vary. Patient sensors, such as pulse oximeters can be inaccurate in a few situations, such as when the pulse oximeter is moved around, which can result in poor quality data. Some patient sensors, such as pulse oximeters can provide a signal quality indicator with each SpO2 reading. The signal quality indicator can be defined as a measure of the accuracy of the measurements of the patient sensor. The value of the signal quality indicator can be computed on a defined scale, such as 0 to 1, where 0 represents no signal and 1 represents the strongest signal. The data representing signal quality from the patient sensor can be processed in one or more ways, including being fit from a different scale (such as 0 to 5) to a defined scale of the system (such as 0 to 1).

When tuning a PID controller (whether it be default, patient specific, or predictive) expected periodic perturbations can be analyzed. Periodic perturbations are fluctuations in the SpO2 due to factors beyond the control variable (FdO2), and include errors in the SpO2 measurement. When tuning the PID controller, the expected periodic perturbations can be estimated, in turn the standard deviation of the SpO2 readings due to signal quality can also be estimated. The SpO2 readings will have a certain level of error between what is measured and the true value. This error can be represented by a measure of standard deviation. The standard deviation would be inversely proportional to the signal quality.

Changes in the signal quality can affect the error of the SpO2 measurements, which affects the periodic perturbations of the system. This means that a previously tuned PID may go from critically damped to overdamped (where the controller is unnecessarily slow) or underdamped (where the controller becomes unstable). The signal quality can be accounted for by weighting the control algorithm based on the signal quality reading from the patient sensor. The control output may be multiplied by the signal quality to reduce the impact of data points with low signal quality. The purpose is to dampen the PID controller as signal quality decreases, effectively retuning the PID controller as the expected periodic perturbations change.

The weighting may be applied to the change in FdO2 output by the PID control. The change in FdO2 would be scaled relative to the most recent signal quality reading. For example, if the FdO2 is at 30%, and a signal from the pulse oximeter indicates that the patient's SpO2 had dropped, the PID might instruct a 4% increase in FdO2 to 34%. However, if the signal quality for said measurement was only 0.5, and a linear weighting is being used, the increase might be dampened to 2%, so that the new FdO2 would only be 32%. The weighting allows the controller to continue to control the patient's SpO2, but to do so slowly in order to not overcompensate for poor quality measurements.

The relationship between signal quality and the control algorithm weighting can be defined by any function designed to represent the increase in noise as signal quality decreases, and is not limited to a linear function as described above. The relationship between signal quality and control weighting can be based on the correlation between signal quality and the standard deviation of the error.

By weighting the SpO2 measurements based on signal quality, the PID controller can be less affected by disturbances in the SpO2 measurements, such as motion artefacts and poor perfusion. Weighting the control algorithm by the signal quality can result in a more robust, stable controller that can compensate for noisy data when the signal quality drops, while giving fast and accurate control when the signal quality is high and the data is reliable.

Process for Control of Flow Therapy Apparatus

Figure 9A:
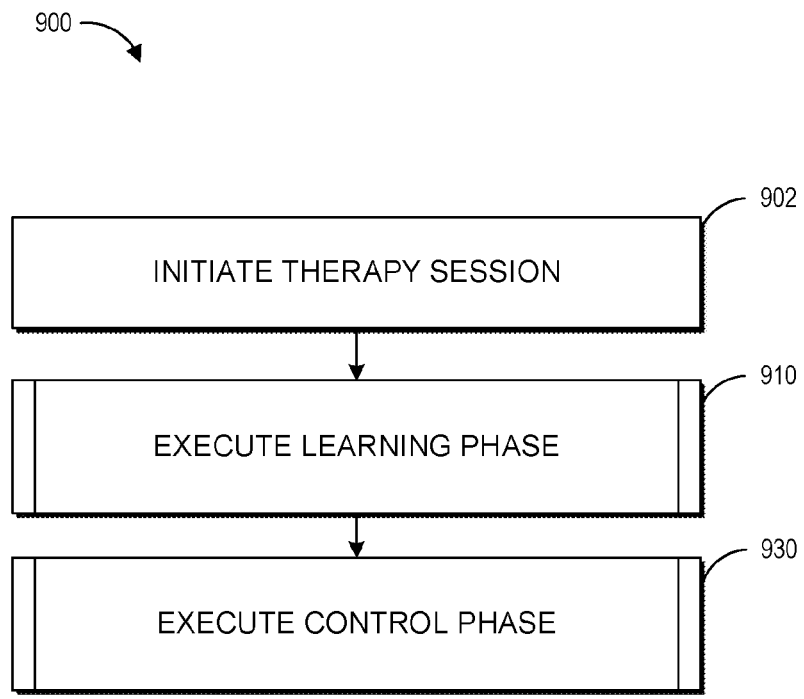
FIG. 9A illustrates a flowchart of a process for a method of controlling operation of a flow therapy apparatus during a flow therapy session.
Figure 9B:
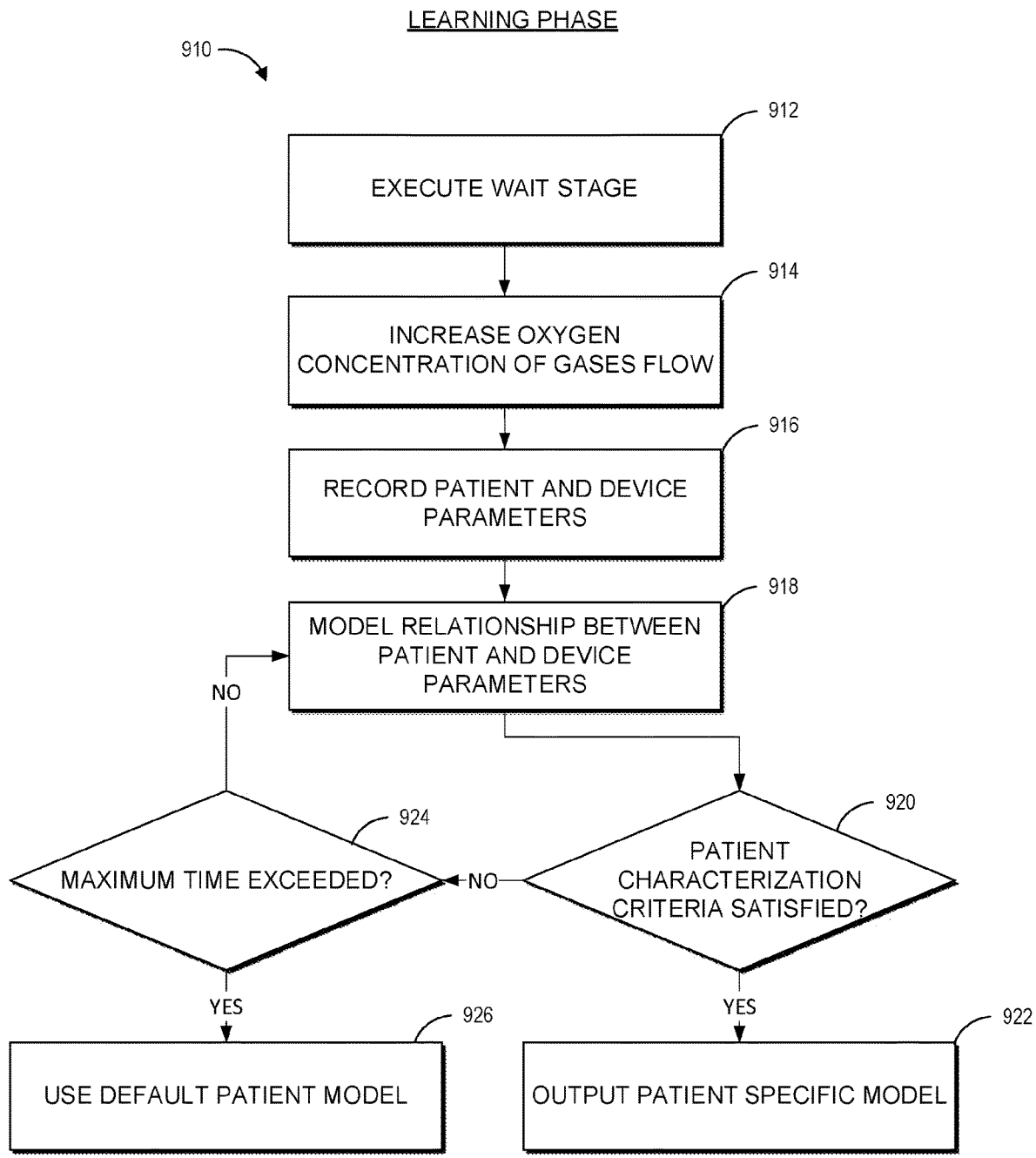
FIG. 9B illustrates a flowchart of a subprocess for a learning phase of the flow therapy session.
Figure 9C:
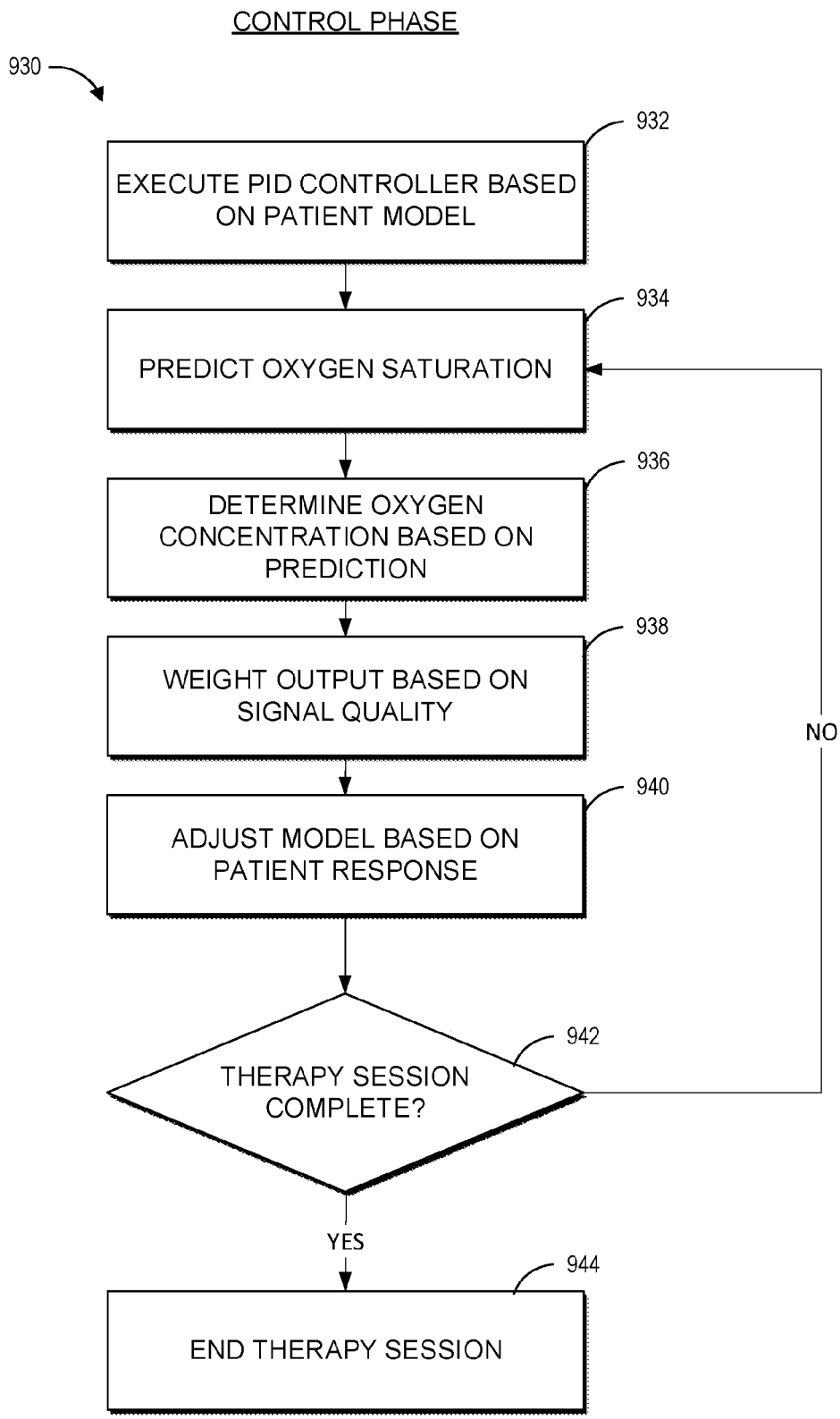
FIG. 9C illustrates a flowchart of a subprocess for a control phase of the flow therapy session.

FIGS. 9A-9C illustrate flowcharts for a method of controlling operation of a flow therapy apparatus during a high flow therapy session. The process 900 and subprocesses 910 and 930 can be implemented by any system that can control operation of the flow therapy apparatus. For example, the process 900, in whole or in part, can be implemented by the controller 13. A plurality of different controllers may be configured to implement the process 900. For example, different aspects of the process can be implemented by the controller. A remotely located system may be configured to implement a portion of the process. For example, the remotely located system may be configured to execute the learning phase 910 of the system and the control phase 930 can be executed locally by the controller 13. Although any number of systems, in whole or in part, can implement the process 900, to simplify discussion, the process 900 will be described with respect to the controller 13 and particular components of the flow therapy system 10.

In process 900, at block 902, a user can initiate a high flow therapy session on a flow therapy apparatus 10. In order to initiate a therapy session, the flow therapy apparatus can require a defined set of information about the patient. For example, the inputs may include one or more patient characteristics, such as, a type of patient (e.g., normal, hypercapnic, or other type), age, weight, height, gender, and/or other patient characteristics. The flow therapy apparatus 10 may also require the user to set a target SpO2 value or range of values for the patient. The flow therapy apparatus may automatically determine the target SpO2 value based at least in part on the received patient characteristics. After the information has been received, the therapy session can be initiated by the user and the process can proceed to block 910.

At block 910, the controller can execute the learning phase subprocess. The learning phase can generate a patient specific model for use during the control phase. In some instances, the learning phase may fail resulting in a default patient model being used during the control phase 930. As discussed herein, a patient specific model may be generated from a default model and then optionally updated during a therapy session without a defined learning phase.

With additional reference to FIG. 9B, the learning phase is described in further detail. At block 912, the controller executes the wait stage until the patient's SpO2 value stabilizes. During the wait stage 202, the oxygen inlet valve will default to the previous FdO2 setting and the valve may open or close as required. The patient's SpO2 may change in response to the high flow therapy, and as such the controller can wait until the SpO2 has settled at a reasonably constant value prior to proceeding to block 914. Optionally, the wait stage may be bypassed and the process can proceed directly to block 914 without executing the wait stage at block 912.

At block 914, the controller can increase the oxygen concentration of the gases flow to a new level based on the target SpO2 level. The new FdO2 value could be pre-set or determined based on factors such as the current SpO2 of the patient. The new FdO2 may be selected by a clinician, who chooses the FdO2 based on their own expertise and knowledge. The chosen FdO2 can bring the patient's SpO2 close to the target SpO2 level. The FdO2 may be determined automatically by the controller 13.

At block 916, the controller measures and records the patient parameters and the device parameters. The patient parameter can be SpO2 and the device parameter can be FdO2. The controller can measure and record the FdO2 and SpO2 data. The actual FdO2 can ramp up to the target FdO2 over a defined period of time. The signal quality indicator from the patient sensor can also be recorded.

At block 918, the controller can analyse the relationship between the patient and device parameters and model the relationship. For example, the relationship can be between FdO2 and SpO2, and the controller can determine a relationship between the measured FdO2 and the amount of time since the change in target FdO2. The relationship may be modelled using an exponential decay function, where the exponential decay constant is varied to best fit the model to the data. Initial and final FdO2 values used in the exponential decay function can be set by the initial and final target FdO2 values. Modelling of the relationship can be performed as further described herein.

At block 920, the controller can determine whether the patient characterization criteria are satisfied. The characterization criteria can define acceptable ranges for at least some of the parameters that are used for calculation of the patient model. For example, the characterization criteria may include a range of acceptable values for a determined delay time between a change in FdO2 and the first change in SpO2, a range of acceptable values for an initial value of SpO2, a range of acceptable values for the rate of exponential decay, which defines how quickly the SpO2 approaches its final value after the delay time, a range of acceptable values for the ratio between change in SpO2 and FdO2, and/or other parameters associated with the generation of the model. The characterization criteria may define only a minimum or maximum value for a parameter. If the criteria is satisfied, at block 922 the controller outputs a patient specific model for use during the control phase. If the patient characterization criteria are not satisfied, the process proceeds to block 924 where the controller determines whether the maximum time for the learning phase has been exceeded. If the time has not been exceeded, the controller continues to iterate on the model. If the time has been exceeded, the controller uses a default patient model for the patient at block 926. The controller may restart the learning phase subprocess 910 one or more times if the patient characterization criteria is not satisfied.

After completion of the learning phase, a model is output for use during the control phase at subprocess 930. The control phase subprocess is further described with respect to FIG. 9C.

At block 932, the controller executes a PID controller based on the patient model output during the learning phase. The PID controller can be configured to control the FdO2 based on the target SpO2. At block 934, the PID can predict the SpO2 using a prediction algorithm, such as a Smith predictor. At block 936, the PID can determine the FdO2 value based on the predicted patient SpO2 value. At block, 938, the PID controller can adjust the output of the FdO2 value based on a signal quality indicator associated with the patient sensor. At block 940, the model is adjusted based on the patient response. The difference between the predicted SpO2 and the target SpO2 is calculated, and the result is fed back into the PID controller. At block 942, the controller determines whether the therapy session is complete. If the therapy session is not complete, the process starts again. If it is complete, the therapy session ends.

Closed Loop Control Using Oxygen Efficiency

In another configuration for implementing a closed loop control system for an flow therapy apparatus 10 illustrated in FIG. 10, the flow therapy apparatus 10 determine an oxygen efficiency associated with the patient. The flow therapy apparatus 10 can generate a patient model that uses the patient's oxygen efficiency during a therapy session.

The system can calculate an estimate of the patient's oxygen efficiency ($\xi_{O2}$), along with other parameters. Generally, the oxygen efficiency can be calculated based on the patient's measured SpO2 and the measured FdO2. In one configuration, the oxygen efficiency is determined based on the patient's measured SpO2 divided by the measured FdO2. In one configuration, the oxygen efficiency is determined based on a non-linear relationship between the patient's measured SpO2 and the measured FdO2.

A patient in need of supplementary oxygen may have an oxygen efficiency that is less than that of a healthy individual. For example, in a healthy individual, a change in FdO2 could cause double the change in SpO2 as it would for a patient SpO2 with low oxygen efficiency. Having a measure of the patient's oxygen efficiency allows for a more efficient execution of a closed loop oxygen control system.

Figure 11:
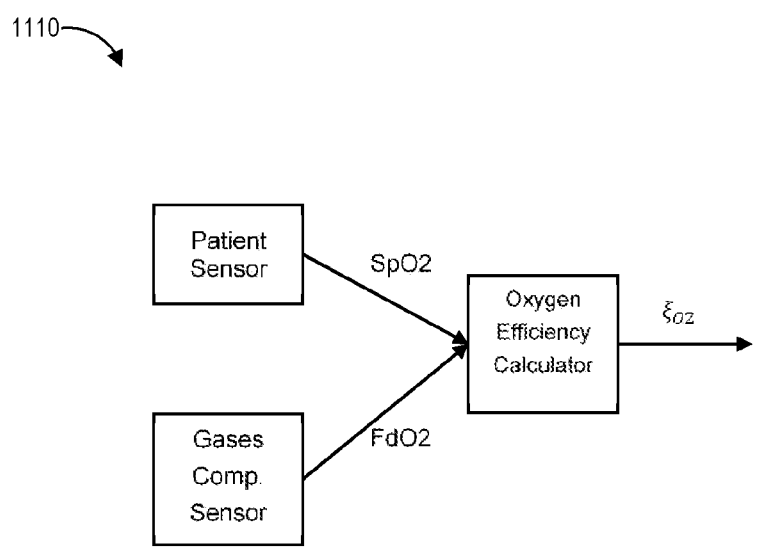
FIG. 11 illustrates a process for calculating oxygen efficiency for a patient.

As illustrated in FIG. 11, the controller 13 can calculate an oxygen efficiency for the patient. The controller can receive a measured SpO2 value and a measured FdO2 value. The measured FdO2 value can be received from the gases composition sensors. An instantaneous oxygen efficiency can then be calculated based on the measured SpO2 the measured FdO2 values. The patient's overall oxygen efficiency can then be estimated by applying a running filter to the instantaneous oxygen efficiency data. Filtering the instantaneous oxygen efficiency data can reduce fluctuations in the estimate of the patient's overall oxygen efficiency. The controller may also prioritize more recent data. The instantaneous oxygen efficiency data can be weighted by the pulse oximeter's signal quality, such that measures of instantaneous oxygen efficiency that were made from data with low signal quality can have a reduced effect on the estimate of the patient's overall oxygen efficiency. The instantaneous oxygen efficiency data can also be weighted based on the size of recent changes to FdO2, such that measures of instantaneous oxygen efficiency that were made from data following a large change in FdO2 can have a reduced effect on the estimate of the patient's overall oxygen efficiency. This is because of a delay between when a change is made in the FdO2 and when there is a change in the measured SpO2. The controller can also take into account whether or not the patient is wearing the cannula when estimating the patient's oxygen efficiency. For example, the controller can disregard efficiency data from periods when the patient is not wearing the cannula.

The device can constantly monitor and update the estimate of the patient's overall oxygen efficiency. The patient's overall oxygen efficiency may be used by multiple parts of the closed loop control system, such as in the predictive model, tuning of the PID coefficients, and/or the step change prior to the feed forward stage. The patient's overall oxygen efficiency can be constantly updated as estimates of the patient's instantaneous oxygen efficiency changes. The controller can start with an initial estimate of the patient's oxygen efficiency based on the typical oxygen efficiency for a patient requiring supplemental oxygen. The overall oxygen efficiency can then be updated as data is received. A higher estimate of the oxygen efficiency can result in smaller changes in FdO2, which can reduce risk to the patient of receiving too much oxygen. A lower estimate can result in larger changes in FdO2, which can allow the controller to achieve the target SpO2 more quickly but may cause overshoot.

In some configurations, the flow therapy apparatus 10 can have an initial oxygen efficiency calculation phase in order to determine an oxygen efficiency of the patient. In some configurations, the oxygen efficiency is not updated after the initial oxygen efficiency calculation.

Initiation of Closed Loop Control Therapy Session

A closed loop control therapy session may be initiated by the user through interaction with the graphical user interface of the flow therapy apparatus 10 as described herein. Closed loop control can require that a patient sensor 26, such as a pulse oximeter, is connected to the patient and the flow therapy apparatus 10, and the signal quality of the patient sensor is at an acceptable level. Before closed loop control begins, the user must set the operating parameters for the FdO2 and SpO2. Various methods for selecting these operating parameters are described herein.

The FdO2 can have a control range having upper and lower limit control values. The user can select the upper and lower limits for the control range of the FdO2. The difference between the upper and lower limits may be a fixed. The control range may be a fixed to a defined difference in oxygen concentration, such as a difference of 5%, 10%, 15%, 20%, 25%, 30%, 35%, 40%, 45% and 50%, and/or any other range between the aforementioned values. The user may then be able to select the specific FdO2 range, such as, for example 25%-45%, 52%-72%, 80%-100%, or any other range. The user may be able to alter the values of the FdO2 control limits in increments of 1%, 2%, 5%, or other increments.

The flow therapy apparatus may have a lower limit of 21% and an upper limit of 100% for the FdO2 control range. The FdO2 control range could be truncated by limits of the oxygen concentration that the device can feasibly deliver (e.g., 95%, 90%, or a lower value). For example, the gases supply source connected to the oxygen inlet valve may be an enriched oxygen gasflow where the oxygen content of the supply source may be less than pure oxygen (i.e., 100%).

The flow therapy apparatus may include various configuration options for setting the limits of the FdO2 control range. For example, the user can input the oxygen concentration of the oxygen source; the flow therapy apparatus can be preprogrammed with an upper limit during manufacturing that cannot be changed; the upper limit can be changed by a technician, but cannot be changed by a regular user; the user can input the oxygen source type (e.g., concentrator, oxygen bottle, etc.), and the flow therapy apparatus can determine an appropriate limit; and/or the flow therapy apparatus can measure the oxygen concentration of the gas coming from the oxygen source.

Additionally, the flow therapy apparatus can alarm if it is unable to achieve the target oxygen concentration. The alarm can act as a failsafe for situations in which a control range above the oxygen source concentration is selected. For example if a control range of 80%-100% when connected to a 90% source, the flow therapy apparatus would not be able to go above 90% and would trigger an alarm.

If the user attempts to lower the control range of the FdO2 above or below the upper or lower limit, respectively, the control range could be truncated. For example, if a user attempted to lower a control limit of 21%-41%, the upper limit could continue to be lowered, but the lower limit would remain at 21%. This would result in a control range that is smaller than 20% (e.g. 21%-35%). The control range may also have a lower limit to its size (e.g., 5%, 10%, 15%, etc.). The lower limit may be based on the size of the control range. For example, the lower limit may be half the size of the control range. Specifically, when one of the limits of the control range is at its physical limit (i.e., 21% or 100%), the other limit must be at least 10% above or below the other limit. In such a configuration, the lowest and highest possible control ranges are 21%-31% and 90%-100%, respectively. The controller can alter the FdO2 between the upper and lower limits of the control range in order to maintain the SpO2 within a target range for the patient.

As described herein, the user can manually set a target range for the SpO2. In some configurations, instead of manually choosing a target range for the SpO2, the user may select the patient type, and the controller then selects predetermined SpO2 control limits based on said patient type. Examples of patient types may include "normal", with a defined SpO2 control range, such as 90%-98%, 92%-98%, 92%-96%, or another defined range, or "hypercapnic", with a defined control range, such as 88%-92%, 86%-90%, 88%-90%, or another defined range.

In order to maintain the patient's SpO2 within the target range, the controller can target the centre of the patient's target range. The limits of the target range can additionally serve as alarm limits. For example, for a "normal" patient with an SpO2 target range of 92%-96%, the device would target an SpO2 value of 94%. The device would then alarm if the SpO2 value of the patient went outside of the 92%-96% range. The flow therapy apparatus may have additional alarms set at defined limits that are independent of the selected SpO2 control range. For example, the flow therapy apparatus may alarm at 50%, 60%, 70%, 75%, and/or 80% to indicate desaturation of the patient.

The flow therapy apparatus 10 may include a configuration menu in which some or all of these values may be able to be changed. The configuration menu may be protected by a PIN or similar password function; such that certain users are prevented from accessing these settings. For example, the configuration menu may be intended to not be accessible to a regular user (such as a patient or a nurse), but instead designed to be accessible to whoever is setting the configuration of the device (such as a technician or the manufacturer).

In the configuration menu, the limits for what may be able to be selected for the FdO2 control range can be modified. For example, the device may be configured such that the upper limit for the control range of FdO2 cannot exceed 90%. Setting limits for the control range can act as a safety feature by preventing the device from delivering excessively high and/or low oxygen concentrations. Additionally, the limit may be set based on what is possible for the device to deliver. For example, if the device is connected to an enriched oxygen source comprising gasses with an oxygen concentration of 90%, then it would be impossible for the device to achieve 100% FdO2. In this situation the upper limit for the selectable FdO2 control range would need to be set at 90% or less.

The size of the control range of the FdO2 may also be able to be changed in the higher level menu. For example, size of the control range may be able to be set to 10%, 15%, 20%, 27% 30%, 36%, 40%, 50%, 60%, 70%, 80%, 90%, 100%, or any other control range. The control range would be able to be reduced when approaching one of the aforementioned limits, such as by half. For example, if the range is set to 40%, with a lower FdO2 limit of 21%, then the lowest selectable range would be 21%-41%.

The SpO2 target ranges can be manually set by the user. The SpO2 target ranges for each patient type may also be able to be altered in the configuration menu. Additionally, the device may have additional patient types that can be made selectable through the configuration menu. For example, additional patient types, may be labelled as "other", and may include customisable SpO2 target ranges. The upper and lower limit for the SpO2 target ranges of each patient type can be changed between 80% and 100% in increments of 1%.

During the therapy session, the SpO2 controller and FdO2 controller can automatically control the operation of the flow therapy apparatus until the therapy session ends or an event triggers a change from the automatic mode to manual mode.

During the therapy session the graphical user interface can display a graphical indicator for the oxygen efficiency. The oxygen efficiency characteristic displayed on the graphical user interface may be an output value based on SpO2 and FdO2. Another oxygen efficiency characteristic may be a function of the determined oxygen efficiency and the respiration rate of the patient. Where the oxygen efficiency characteristic is a function of the determined oxygen efficiency and the respiration rate of the patient, it may be calculated by dividing SpO2 by FdO2, and then dividing this value by respiratory rate. The oxygen efficiency characteristic values can be recorded and displayed in a graph or trend line format to show how the values change over time. The graphical user interface can be configured to display the each of the oxygen efficiency characteristic and the respiration rate oxygen efficiency characteristic individually or together. For example, the values associated with each characteristic may be displayed together on the same screen or on separate screens (e.g., a user can transition to different screens within the interface to view different characteristics). The graph or trend line may be configured to display each characteristic individually or together on the same screen.

Figure 12:
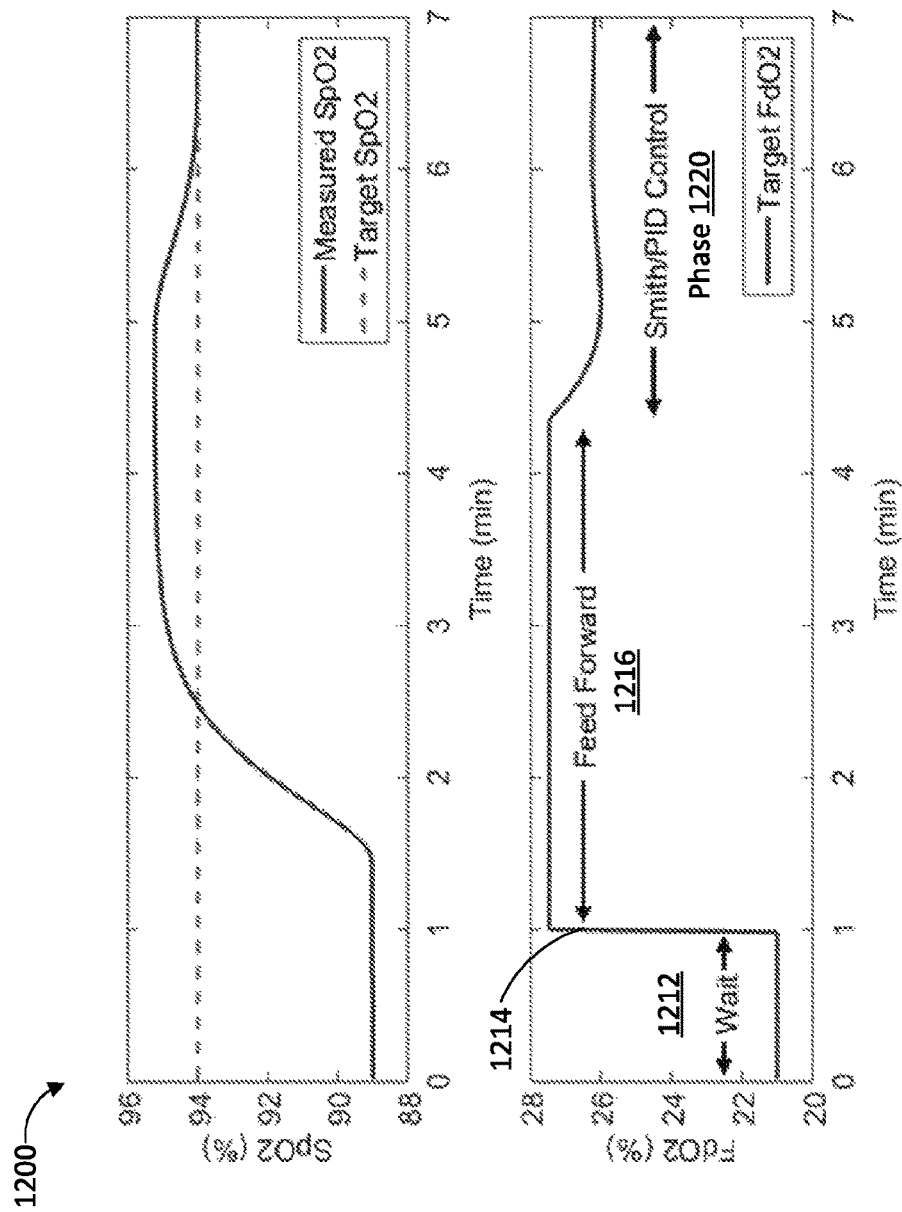
FIG. 12 illustrates graphs showing phases of operation of a flow therapy apparatus.

FIG. 12 provides graphs 1200 for SpO2 and FdO2 illustrating the phases of the operation of the flow therapy apparatus during a therapy session. Although FdO2 (oxygen fraction delivered) is used in the graphs, as previously discussed earlier, the FdO2 is substantially the same as FiO2 so long as the flow rate meets or exceeds the peak inspiratory demand of the patient.

The phases of operation include a wait stage 1212, a step change 1214, a feed forward stage 1216, and a control phase 1220. Once the control limits have been set, the flow therapy apparatus 10 may enter the wait stage 1212. The wait stage 1212 allows the SpO2 sensor to settle, as well as allowing some initial collection of data, such as SpO2, FdO2, signal quality, and other parameters. In particular, an initial estimation of the patient's oxygen efficiency can be determined. If the patient has already been using the device in manual oxygen control mode with the SpO2 sensor attached, then the device may already have an estimation of the patient's oxygen efficiency. In which case, the data collected can be used to continue to update this estimation.

In this configuration, the wait stage 1212 can extend for a fixed predetermined amount of time. This amount of time could be between 1 second and 60 seconds, or between 2 second and 30 seconds, or between 3 seconds and 15 seconds, or between 4 seconds and 10 seconds, 5 seconds, or any other time period within the above ranges.

During the wait stage 1212 the device can also evaluate the data in order to determine what actions will be performed during the subsequent feed forward stage 1216. Prior to the feed forward stage 1216, the controller may execute a step change 1214 in the FdO2. The flow therapy apparatus can make the step change to the FdO2 in an attempt to bring the actual SpO2 within or close to the target range. After making the step change to the FdO2, the FdO2 can be held constant during a feed forward stage 1216 for a defined duration in order to allow the SpO2 of the patient to settle.

Near the end of the wait stage 1212, the data for several parameters can be evaluated to determine a magnitude of the step change 1214 and whether a feed forward stage 1216 will be executed. First, the patient's SpO2 can be compared with the target SpO2 range. If the patient's SpO2 is within or above the target range then the step change 1214 and feed forward stage 1216 can be bypassed and the controller will transition directly from the wait stage 1212 to the control phase 1220. If the patient's SpO2 is below the target range, then the controller can determined whether the step change 1214 is required. For example, large recent changes in FdO2 could mean that a step change 1214 in FdO2 is not required.

If a step change 1214 is required, then the device will proceed to the step change 1214 following the end of the wait stage 1212.

For the step change 1214, the controller determines the change in FdO2 that will be implemented. The magnitude of the step change is based at least in part on the current SpO2, the target SpO2, and the oxygen efficiency.

Due to the delay between changing the FdO2 and seeing a change in the SpO2, it is possible that there are changes to the FdO2 that had not yet taken effect when calculating oxygen efficiency. The flow therapy apparatus 10 can take into account any recent changes in the FdO2 when determining the predicted SpO2, oxygen efficiency, and the magnitude of the step change.

During the feed forward stage 1216, the controller maintains the FdO2 at the determined FdO2. In instances where no step change 1214 occurs, the FdO2 can be maintained at the current FdO2 value. In instances where there is a step change 1214, the determined FdO2 is the sum of the previously measured FdO2 and the magnitude of the step change. The feed forward stage 1216 can continue until a defined maximum time for the feed forward stage is reached (e.g., 60 seconds, 120 seconds, or another defined maximum duration), or until the measured SpO2 is at a target SpO2 value and/or within the target SpO2 range. After the feed forward stage 1216 ends the control phase 1220 begins.

Predictive Control During Control Phase

During the control phase 1220, the controller changes the FdO2 within the control range in order to achieve the target SpO2. In velocity form, the formula for determining the target FdO2 during the control phase is shown below.

$$\frac{dTargetFdO2(t)}{dt} = -K_P \frac{dE_{SpO2}(t)}{dt} - K_I E_{SpO2}(t) - K_D \frac{d^2 E_{SpO2}(t)}{dt^2}$$

Where $E_{SpO2}$ is the error function, and $K_P$, $K_I$, and $K_D$, are the PID coefficients. The error function is representative of how far the patient's SpO2 is from the target SpO2, and is calculated differently depending on whether or not the Smith predictor is used. In some configurations, the error function may also be filtered with a first order low pass Butterworth filter to remove random measurement error.

As described herein, the PID coefficients can be tuned to better achieve the target SpO2 of the patient. Additionally, the PID coefficients can also be weighted by the inverse of the patient's oxygen efficiency, such that the controller will make larger changes to the FdO2 for a patient with low oxygen efficiency in order to achieve consistent changes in SpO2.

When a default PID or tuned PID is used the error function is as follows.

$E_{SpO2}(t) = SpO2_{Measured}(t) - SpO2_{Target}$

As discussed herein, the PID coefficients can be tuned based on patient characteristics. Additionally, the Smith predictor can be used to remove the pure time delay between when a change is made in the FdO2 and when a corresponding change in the SpO2 is detected. The delay time can be estimated based on the flow rate of the flow therapy apparatus 10.

The Smith predictor can use a model of the patient's SpO2 response based on changes in the FdO2. Using the model, the Smith predictor can make a prediction of what the SpO2 will be after the delay time.

The predicted value is constantly corrected using a disturbance term, which represents the error between the modelled SpO2 and the measured SpO2. Once the initial SpO2 prediction has been made, the prediction is then adjusted by incorporating the disturbance term. Combining these parameters gives a disturbance adjusted predicted SpO2 value. This value is then used in calculating the error function. When the model and estimated delay time are sufficiently accurate, the Smith predictor PID can function similar to a default or tuned PID used on a patient with no delay time.

As described herein, in some configurations, the Smith predictor model can be evaluated in terms of SpO2, using an accumulation of changes in FdO2 multiplied by a coefficient that represents the relationship between a change in FdO2 and a change in SpO2. The coefficient is specific to the patient and generated using an initial estimation. The coefficient is then constantly updated based on live data received from the patient (for example, SpO2 and FdO2). The coefficient can be updated during all phases of the closed loop control mode, and is not limited to a specific learning phase.

The coefficient used in the Smith Predictor model can be the patient's oxygen efficiency. The patient's oxygen efficiency can be constantly evaluated and updated in the model's algorithm. As stated herein, the oxygen efficiency estimation is updated throughout the wait stage, the feed forward stage, and the control phase, as well as during manual mode if a pulse oximeter is being used.

PID Controller Weighting

As described herein, the control signal can be weighted by the signal quality from the patient sensor 26. In addition to this, the control signal can also be weighted depending on whether the measured SpO2 is above or below the target value. When the measured SpO2 is below the target, the weighting can be equal to or greater than one, between 1 and 2, between 1.1 and 1.75, between 1.2 and 1.5, 1.25, or any value or range within the aforementioned ranges. When the measured SpO2 is above the target, the weighting can be less than or equal to one, between 0.25 and 1, between 0.5 and 0.9, between 0.75 and 0.85, 0.8, or any value or range within the aforementioned ranges. This allows the controller to increase the oxygen concentration more quickly when the SpO2 is too low, while also reducing the chances of overshooting the SpO2 target when the SpO2 is too high and the oxygen concentration is being decreased. This weighting process can help to reduce the amount of time that the patient receives lower concentrations of oxygen.

Process for Control of Flow Therapy Apparatus

Figure 13A:
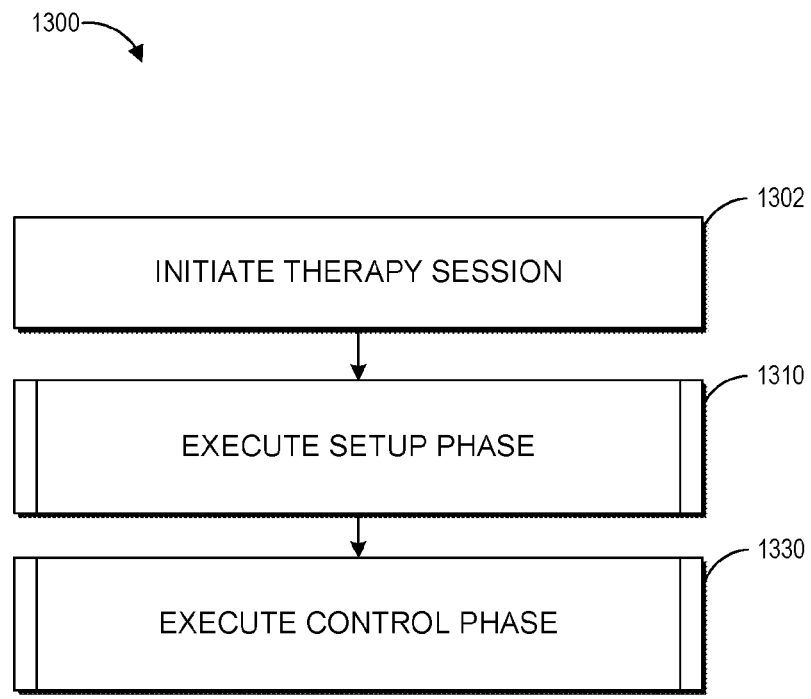
FIG. 13A illustrates a flowchart of a process for a method of controlling operation of a flow therapy apparatus during a flow therapy session.
Figure 13B:
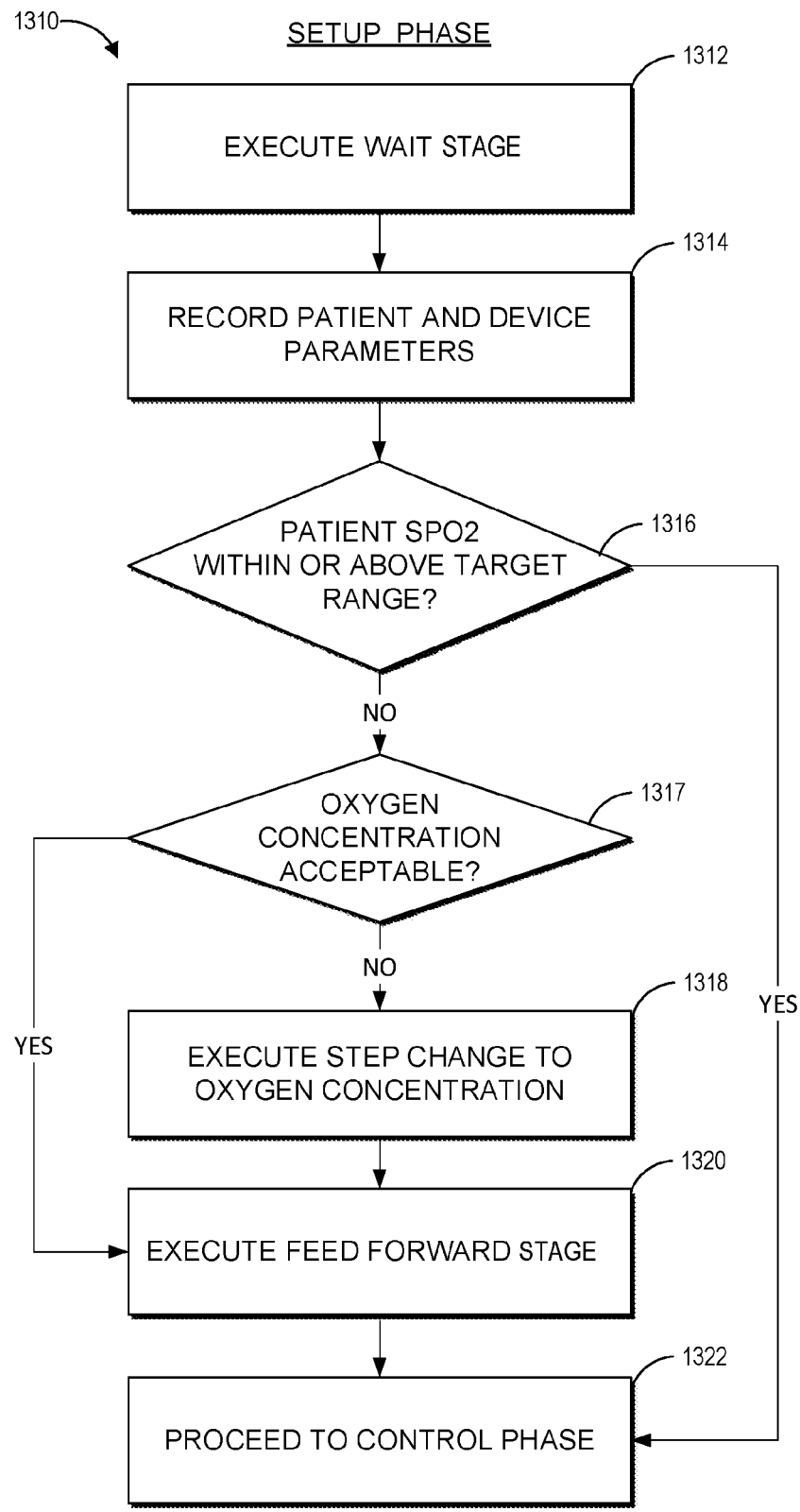
FIG. 13B illustrates a flowchart of a subprocess for a setup phase of the flow therapy session.
Figure 13C:
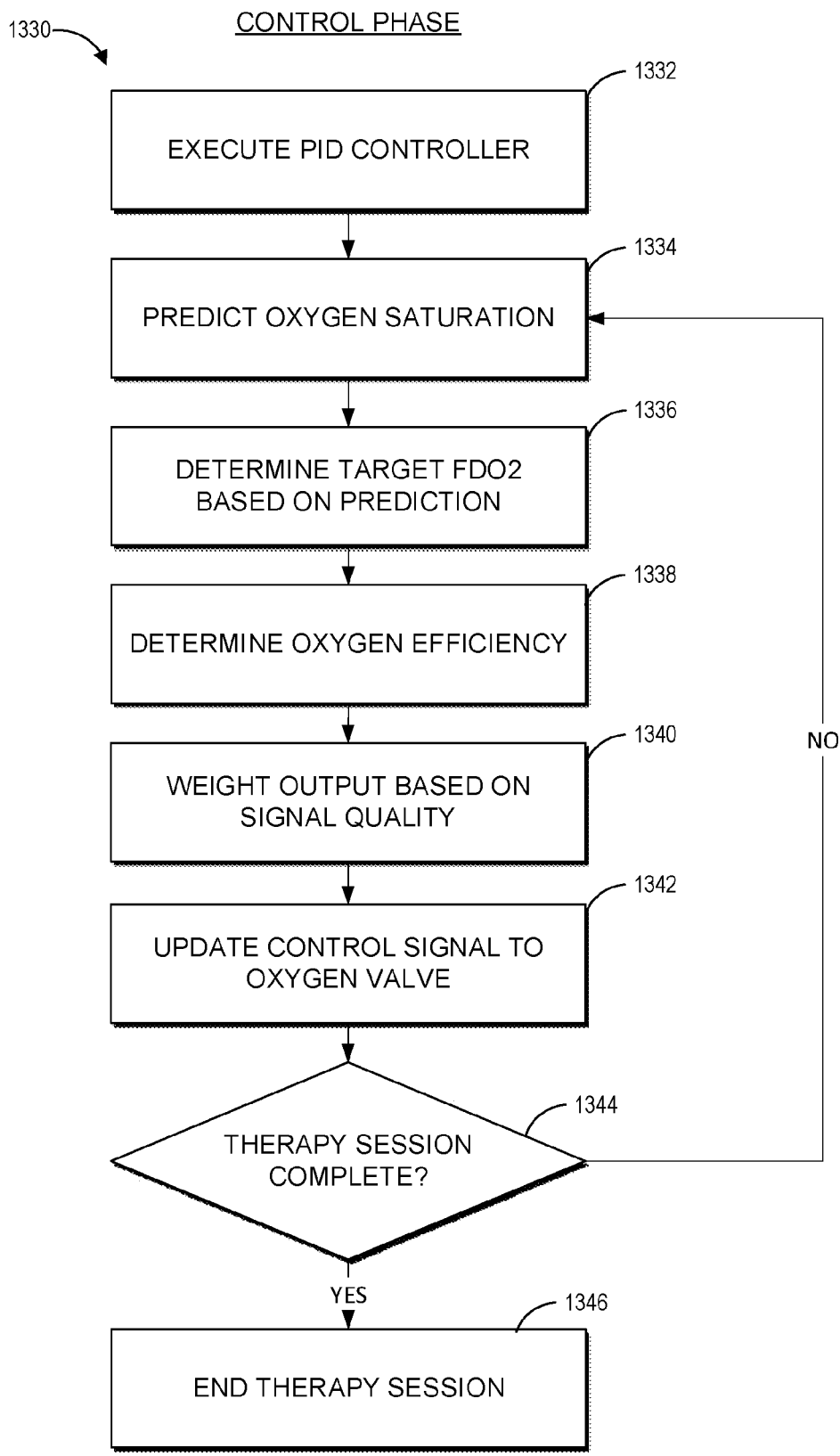
FIG. 13C illustrates a flowchart of a subprocess for a control phase of the flow therapy session.

FIGS. 13A-13C illustrate flowcharts for a method of controlling operation of a flow therapy apparatus during a high flow therapy session. The process 1300 and subprocesses 1310 and 1330 can be implemented by any system that can control operation of the flow therapy apparatus. For example, the process 1300, in whole or in part, can be implemented by the controller 13. A plurality of different controllers may be configured to implement the process 1300. For example, different aspects of the process can be implemented by the controller. A remotely located system may be configured to implement a portion of the process. For example, the remotely located system may be configured to execute the setup phase 1310 of the system and the control phase 1330 can be executed locally by the controller 13. Although any number of systems, in whole or in part, can implement the process 1300, to simplify discussion, the process 1300 will be described with respect to the controller 13 and particular components of the flow therapy system 10.

In process 1300, at block 1302, a user can initiate a high flow therapy session on a flow therapy apparatus 10. In order to initiate a therapy session, the flow therapy apparatus may require a defined set of information about the patient. For example, the inputs may include one or more patient characteristics, such as, a type of patient (e.g., normal, hypercapnic, or other type), age, weight, height, gender, and/or other patient characteristics. The flow therapy apparatus 10 may also require the user to set a target SpO2 value or range of values for the patient. The flow therapy apparatus may automatically determine the target SpO2 value or range of values for the patient based at least in part on the received patient characteristics. After the information, if any is required, has been received, the therapy session can be initiated by the user and the process can proceed to block 1310.

At block 1310, the controller can execute the setup phase. The setup phase subprocess 1310 will be described with additional reference to FIG. 13B. At block 1312, the controller for waits a defined period of time before proceeding. The wait time can provide a period of time for the patient's SpO2 value to settle. During the wait stage 1212, the oxygen inlet valve can default to the previous FdO2 setting and the valve may be open or closed as required.

At block 1314, during the wait stage the controller measures and records the patient parameters and the device parameters. The patient parameter can be SpO2 and the device parameter can be FdO2. The controller can measure and record the FdO2 and SpO2 data. The controller can determine an oxygen efficiency based on the SpO2 and FdO2.

At block 1316, the controller can determine whether the patient's SpO2 is within or above the target SpO2 range. If the target is already within or above the target SpO2 range, then the process bypasses the step change and the feed forward stage, and proceeds directly to the control phase at block 1322. If the patient's SpO2 value is not within the target range, the process proceeds to block 1317

At block 1317, the controller can determine whether the FdO2 is at an acceptable level. If the FdO2 is already at an acceptable level due to recent changes in the FdO2, then no further adjustment to the FdO2 is required prior to the feed forward stage and the process bypasses the step change and proceeds directly to block 1320. If the FdO2 is not at an acceptable level, the process proceeds to block 1318.

At block 1318, the controller can execute a step change in oxygen concentration. The controller can execute a step change to increase the oxygen concentration of the gases flow to a new level based on the target SpO2 level, the FdO2, and the oxygen efficiency. The new FdO2 value can be determined based on factors such as the current SpO2 of the patient. The new FdO2 may be selected by a clinician, who chooses the FdO2 based on their own expertise and knowledge. The chosen FdO2 can bring the patient's SpO2 close to the target SpO2 level. The FdO2 may be determined automatically by the controller 13.

At block 1320, the controller can execute the feed forward stage. During the feed forward stage 1216, the controller maintains the FdO2 at the determined value for a determined amount of time. When the controller bypasses the step change, the controller can proceed with the feed forward stage without changing the FdO2. The feed forward stage 1216 can continue until a defined maximum time for the feed forward stage is reached (e.g., 120 seconds), or until the measured SpO2 is at a target SpO2 value and/or within the target SpO2 range. After completion of the feed forward stage, the process proceeds to block 1322 and begins the control phase subprocess 1330. The control phase subprocess 1330 is further described with respect to FIG. 13C.

At block 1332, the controller executes a control phase that uses a PID controller to control execution of the flow therapy apparatus 10. The PID controller can be configured to control the FdO2 based on the target SpO2 and the measured SpO2. At block 1334, the controller can predict the SpO2 using a prediction algorithm, such as a Smith predictor. At block 1336, the controller can determine the target FdO2 value based on the predicted patient SpO2 value. At block, 1338, the controller can determine the oxygen efficiency based on the measured SpO2 value and the measured FdO2. At block 1340, the controller can adjust the output of the FdO2 value based on a signal quality indicator associated with the patient sensor. At block 1342, the controller control signal to oxygen valve is adjusted. The difference between the predicted SpO2 and the target SpO2 is calculated, and the result is fed back into the PID controller to control the oxygen valve. At block 1344, the controller determines whether the therapy session is complete. If the therapy session is not complete, the process continues until therapy session ends.

Motor and/or Sensor Module Configuration

Figure 14:
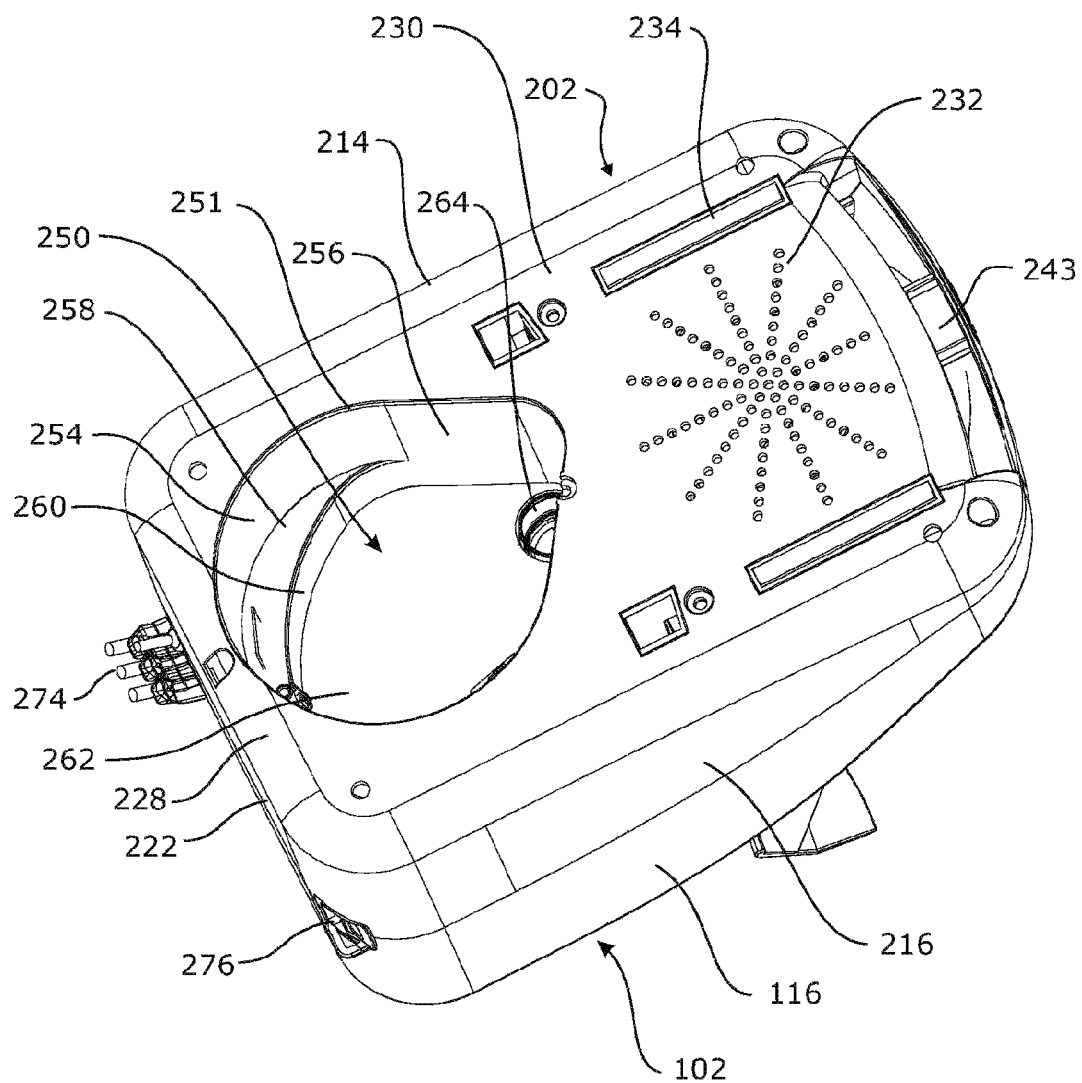
FIG. 14 is a first underside perspective view of the main housing of the flow therapy apparatus showing a recess inside the housing for the motor and/or sensor module sub-assembly.
Figure 15:
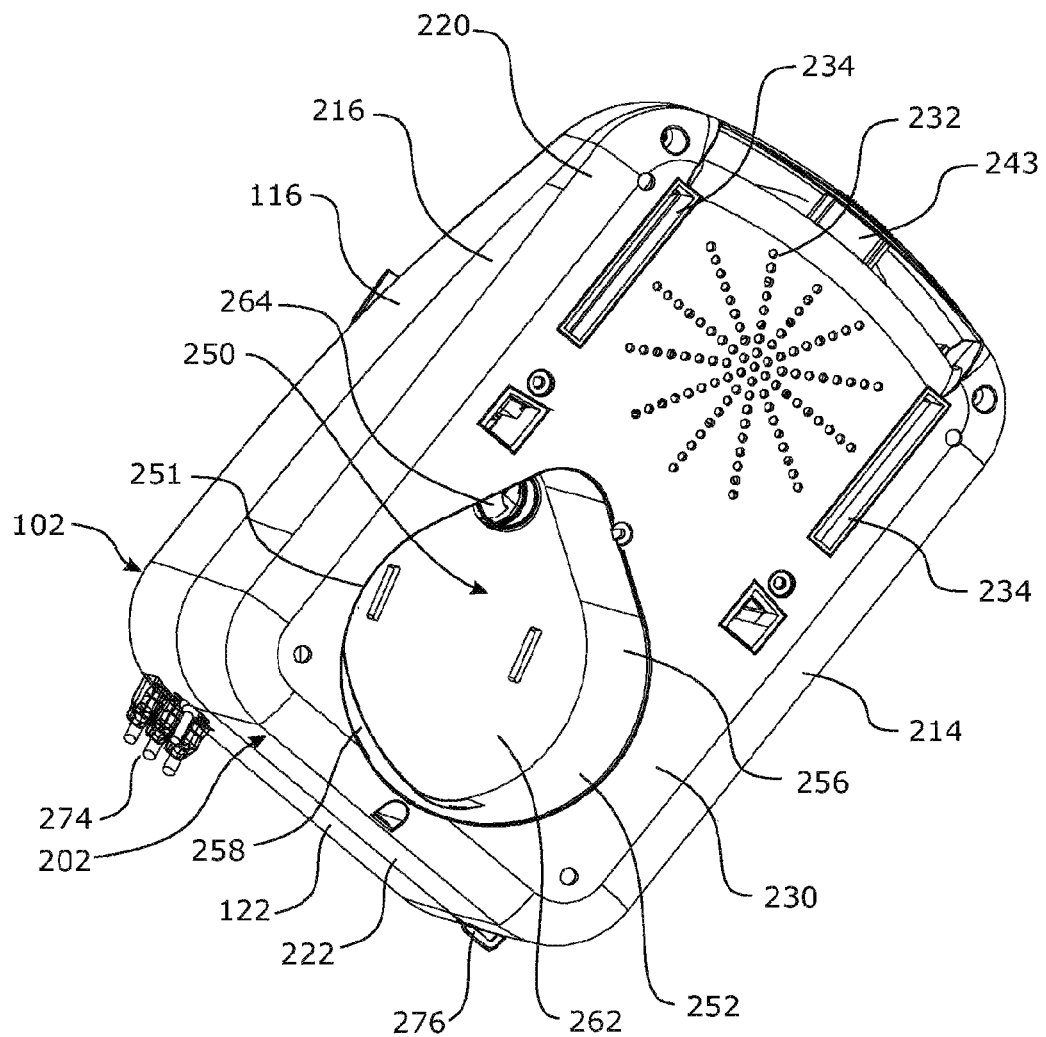
FIG. 15 is a second underside perspective view of the main housing of the flow therapy apparatus showing the recess for the motor and/or sensor module sub-assembly.
Figure 16:
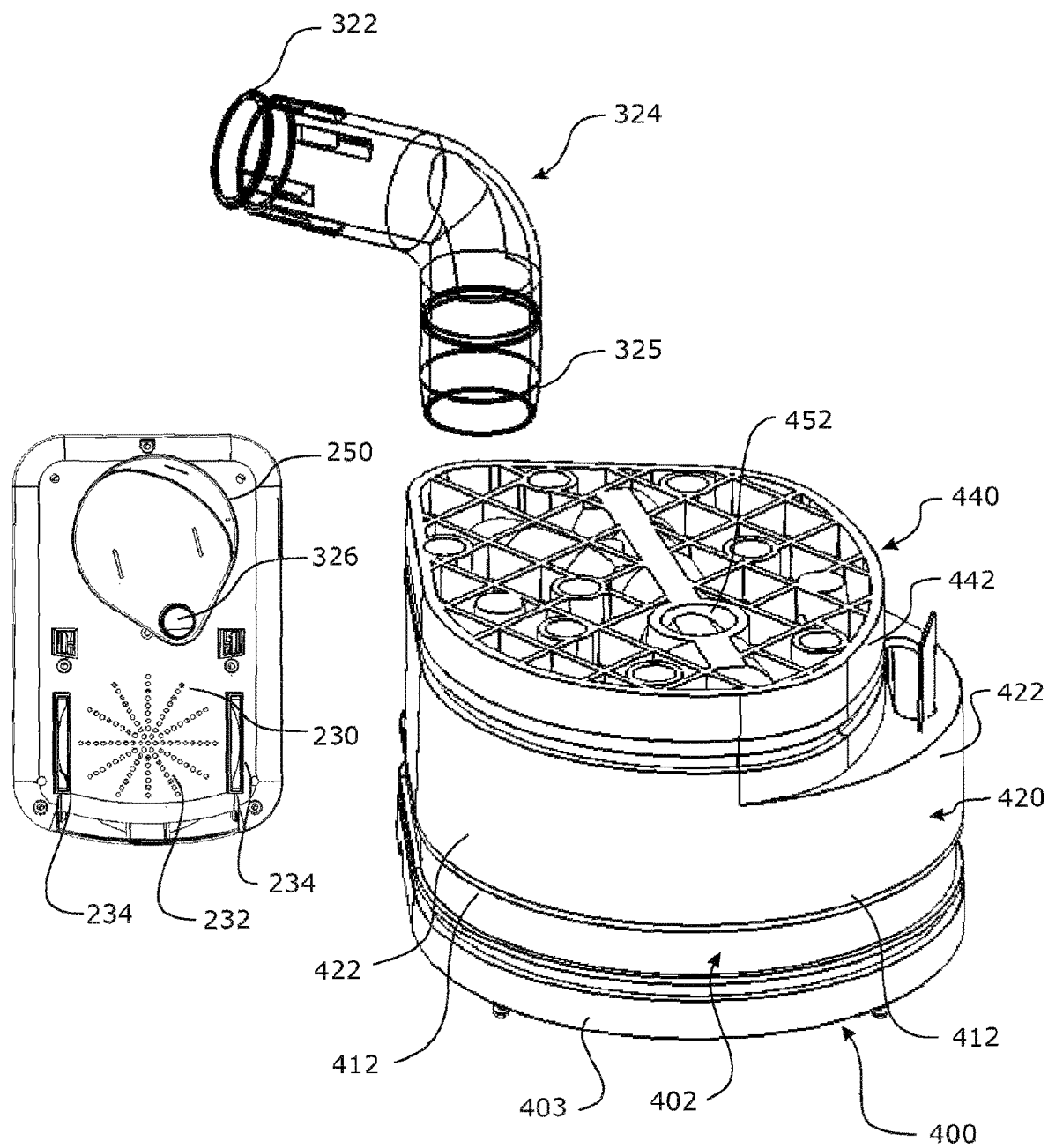
FIG. 16 is a perspective view of the motor and/or sensor subassembly, underside of the main housing, and fixed elbow of the flow therapy apparatus.

A configuration of a flow therapy apparatus 10 is illustrated in FIGS. 14 to 16. The flow therapy apparatus comprises a main housing 100. The main housing 100 has a main housing upper chassis 102 and a main housing lower chassis 202.

As shown in FIGS. 14 and 15, the lower chassis 202 has a motor recess 250 for receipt of a removable or non-removable motor and/or sensor module 400 which is shown in FIGS. 13 to 15 and will be described in further detail below. A recess opening 251 is provided in the bottom wall 230 adjacent a rear edge thereof, for receipt of a removable or non-removable motor/sensor module 400 which is shown in FIGS. 13 and 15 and will be described in further detail below.

FIGS. 16 to 19 show the motor and/or sensor module or sub-assembly 400 in greater detail. As discussed above, the lower chassis 202 comprises a recess 250 for receipt of the motor and/or sensor module 400.

In the form shown in FIGS. 16 to 19, the motor and/or sensor module 400 comprises a stacked arrangement of three main components; a base 403 of the sub-assembly 400 (on which is positioned the motor 402), an outlet gas flow path and sensing layer 420 positioned above the base 403, and a cover layer 440. The base 403, the sensing layer 420, and the cover layer 440 assemble together to form a sub-assembly housing that has a shape that is complementary to that of the recess 250 so that the sub-assembly 400 can be received in the recess 250. The base 403 is configured to close the recess opening 251 when the sub-assembly 400 is positioned in the recess 250. The sub-assembly 400 may be maintained in position in the recess in any suitable way such as with fasteners, clips, or a quick release arrangement for example, or fixed in a non-removable manner.

The sensing layer comprises a gas flow path with one or more sensors, the gas flow path arranged to deliver gas to the outlet port of the housing.

The motor 402 has a body 408 that defines an impeller chamber that contains an impeller. The motor 402 could be any suitable gas blower motor, and may for example be a motor and impeller assembly of the type described in published PCT specification WO2013/009193. The contents of that specification are incorporated herein in their entirety by way of reference.

A gases outlet 406 is in fluid communication with a gases inlet of the outlet gas flow path and sensing layer 420, which is stacked on top of the motor. This layer 420 comprises a body 422 which comprises a plurality of mounting legs 425 that can be inserted into a plurality of mounting slots (not shown) of the base 403 to secure the body 422 to the base 403. In one configuration, the body 422 defines a gas flow path that couples the gases outlet 406 with the gases inlet of the gas flow path and sensing layer 420.

The body 422 defines a lower portion 426 of a sensing and gas flow path. The cover layer 440 has a body 442 that defines the upper portion 446 of the sensing and gas flow path, with the shape of the upper and lower portions 426, 446 corresponding substantially to each other.

Figure 17:
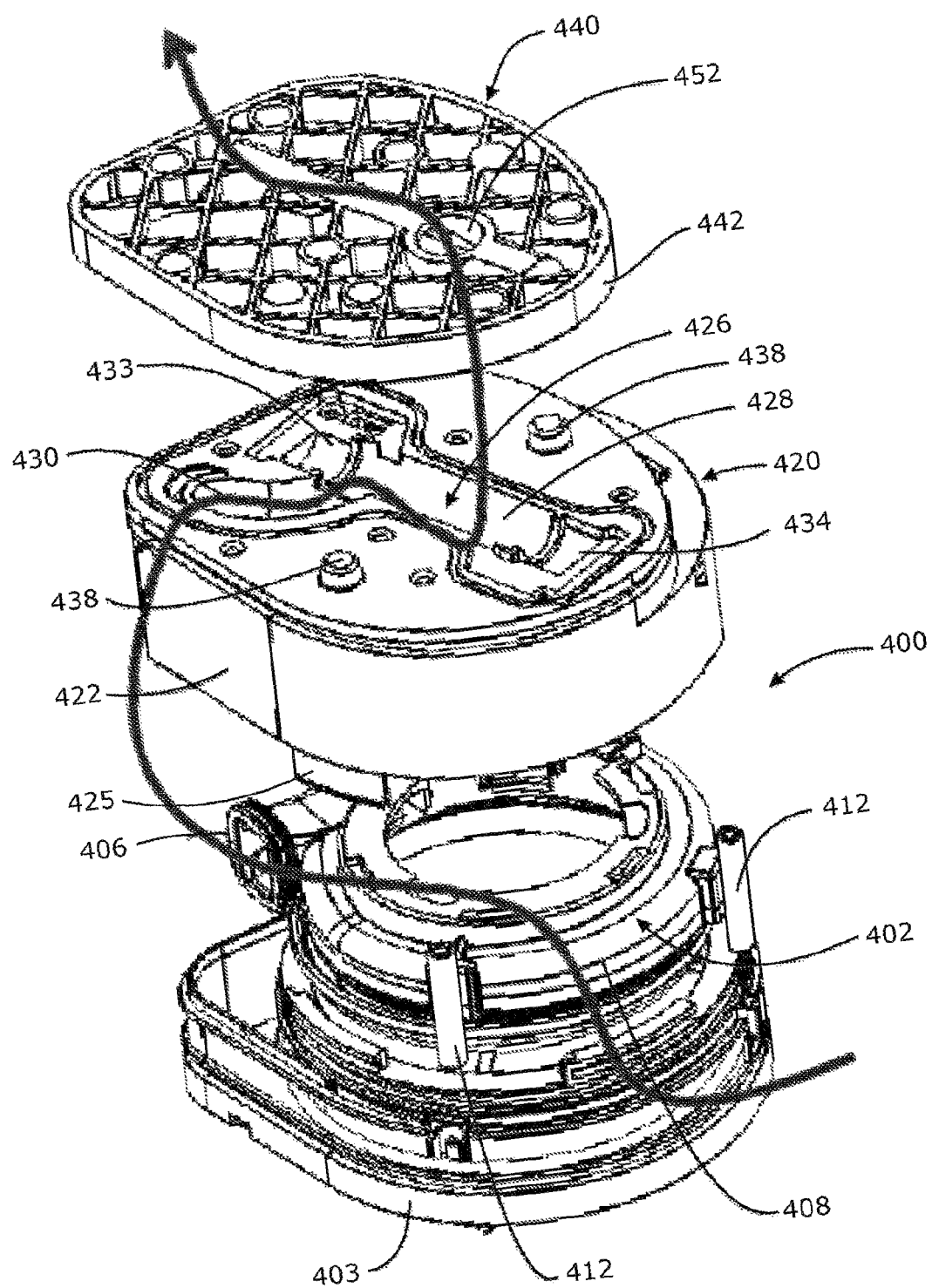
FIG. 17 is an exploded perspective view of components of the motor and/or sensor sub-assembly schematically showing by way of an arrow the gas flow path through the sub-assembly.
Figure 18:
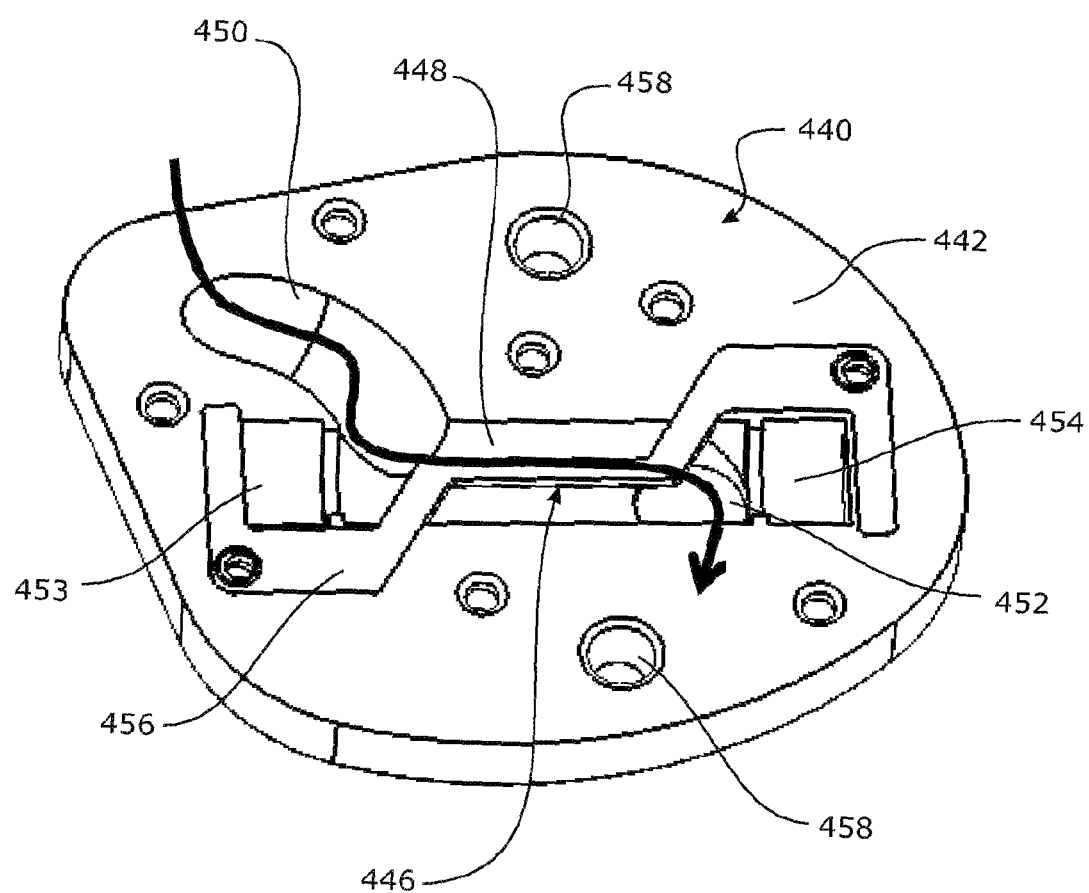
FIG. 18 is an underside view of a cover and sensing PCB of the motor and/or sensor sub-assembly showing the position of sensors.

As shown in FIGS. 17 and 18, the gas flow path comprises a linear elongate gas flow portion 428, 448. The inlet is in fluid communication with a tangential entrance portion 430, 450 of the gas flow path, which is located at or adjacent an entrance end of the linear elongate portion 428, 448 of the gas flow path. Recesses 433, 453 and 434, 454 may be provided at opposite ends of the linear elongate portion of the gas flow path.

A gas flow outlet port 452 extends vertically through the body 442 of the cover layer 440, and is located at or adjacent an opposite exit end of the linear elongate portion 428, 448 of the gas flow path. The gas outlet port 452 is in fluid communication with an upper portion of the motor recess 250, which in turn is in fluid communication with the gas flow passage. Again, due to the wall 252 and ceiling 262 configuration of the recess 250, if there is gas leakage from the motor/sensor module 400, that will be vented to atmosphere rather than entering the portion of the main housing 100 that contains the bulk of the electronics and control equipment. The recess 250 may comprise spacer(s), such as lugs that protrude downwardly from ceiling 262 as shown in FIG. 15, to maintain a suitable spacing for gas flow from the gas outlet port 452 and the ceiling of the recess 262.

It can be seen from FIG. 17 that that at least part of the gas flow path through and out of the motor and/or sensing module 400 has a tortuous or sinuous configuration. For example, the direction of gas flow travel through the elongate portions 428, 448 is generally opposite to the direction of gas flow travel from the gas outlet port 452 to the entrance of the gas flow passage through elbow 324.

Figure 19:
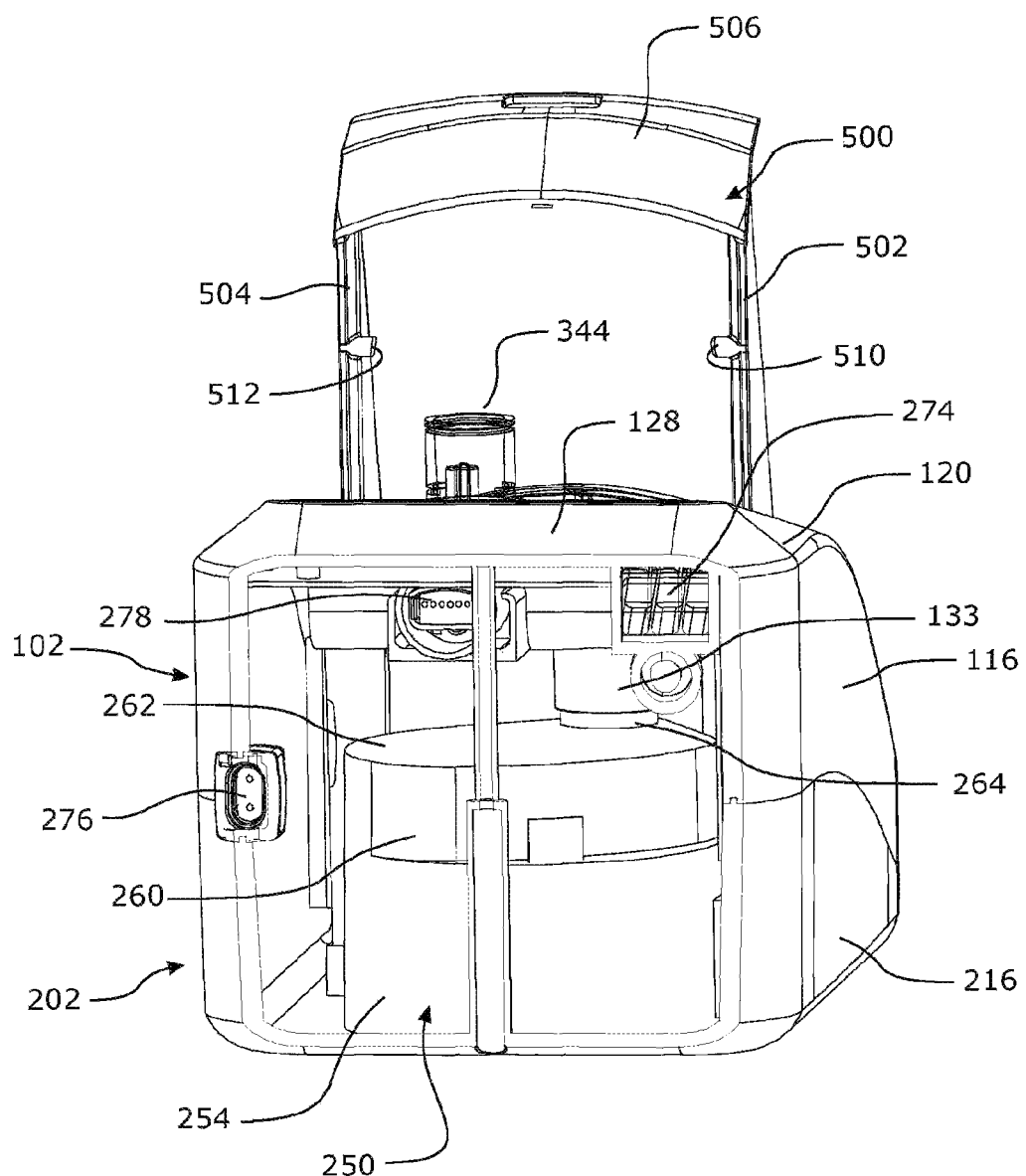
FIG. 19 is a rear perspective view of the flow therapy apparatus sectioned adjacent the rear edge of the apparatus, showing the arrangement of a portion of the main housing that provides the recess for receipt of the motor and/or sensor sub-assembly.
Figure 20:
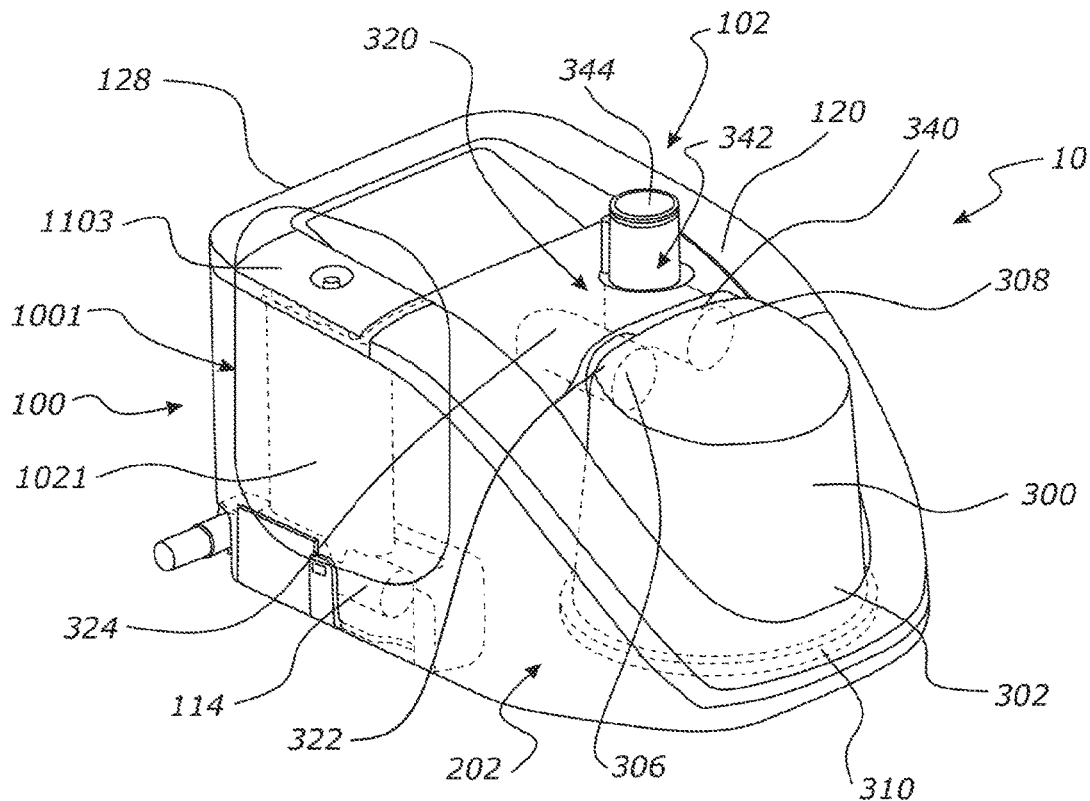
FIG. 20 is a left front perspective view of the flow therapy apparatus.
Figure 21:
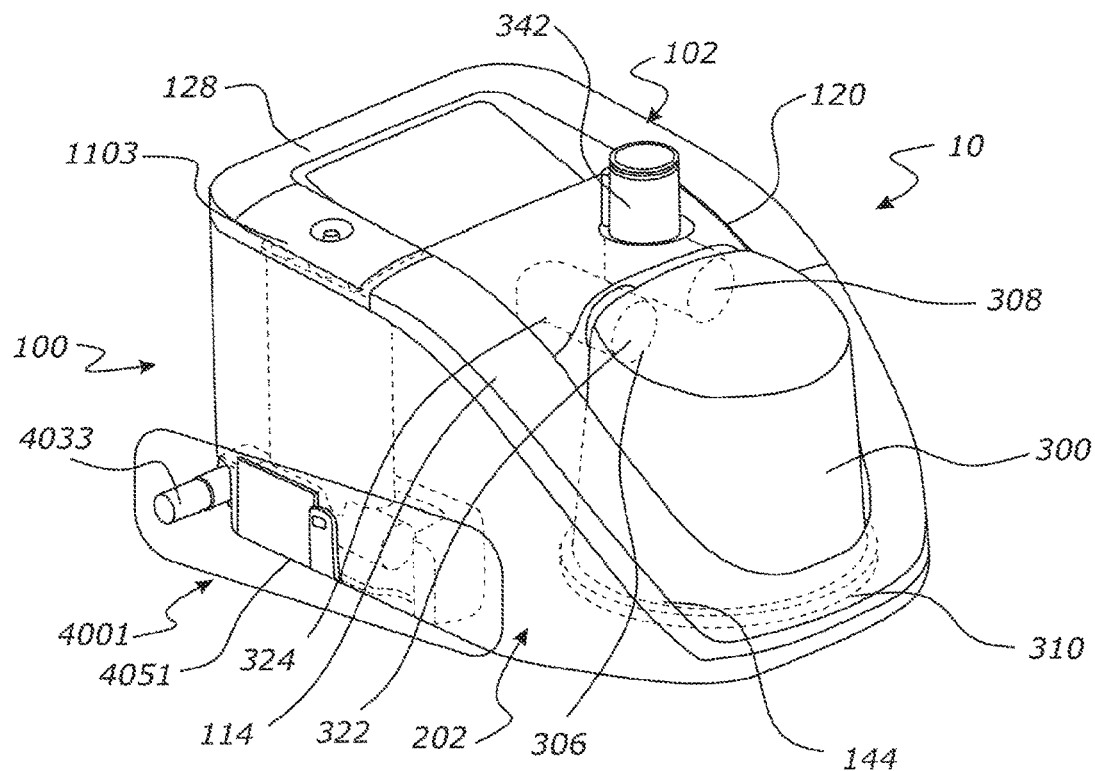
FIG. 21 is a left front perspective view of the flow therapy apparatus.
Figure 22:
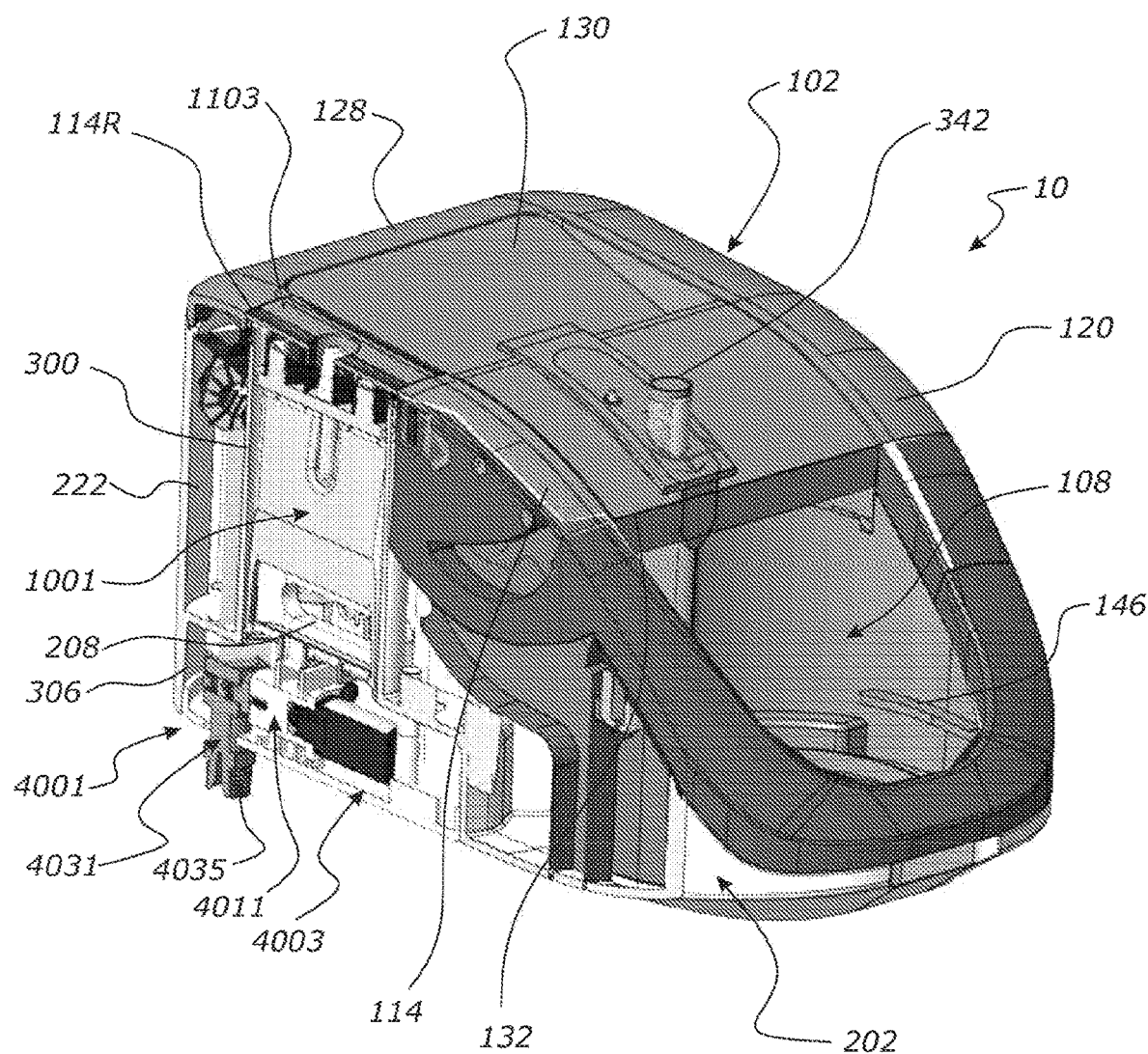
FIG. 22 is a left front perspective partial cutaway view showing the valve module and the filter module.
Figure 23:
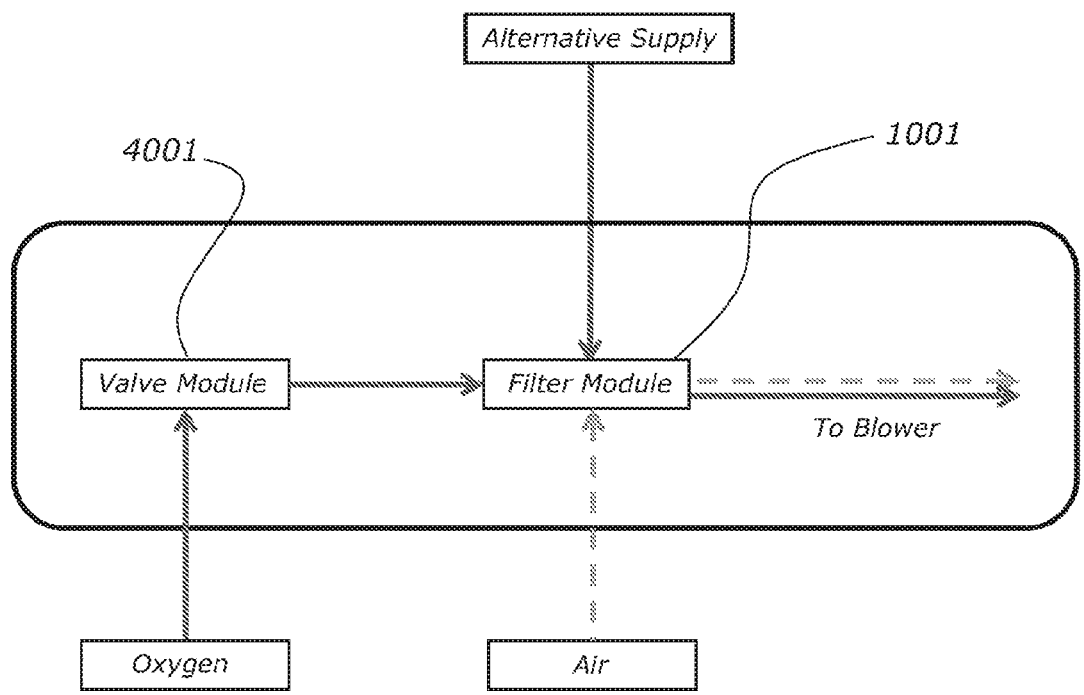
FIG. 23 is a schematic gas flow path diagram for the filter module and the valve module, with the solid line arrows representing the flow of oxygen (or another gas), and the dashed line arrows representing the flow of ambient air.
Figure 24:
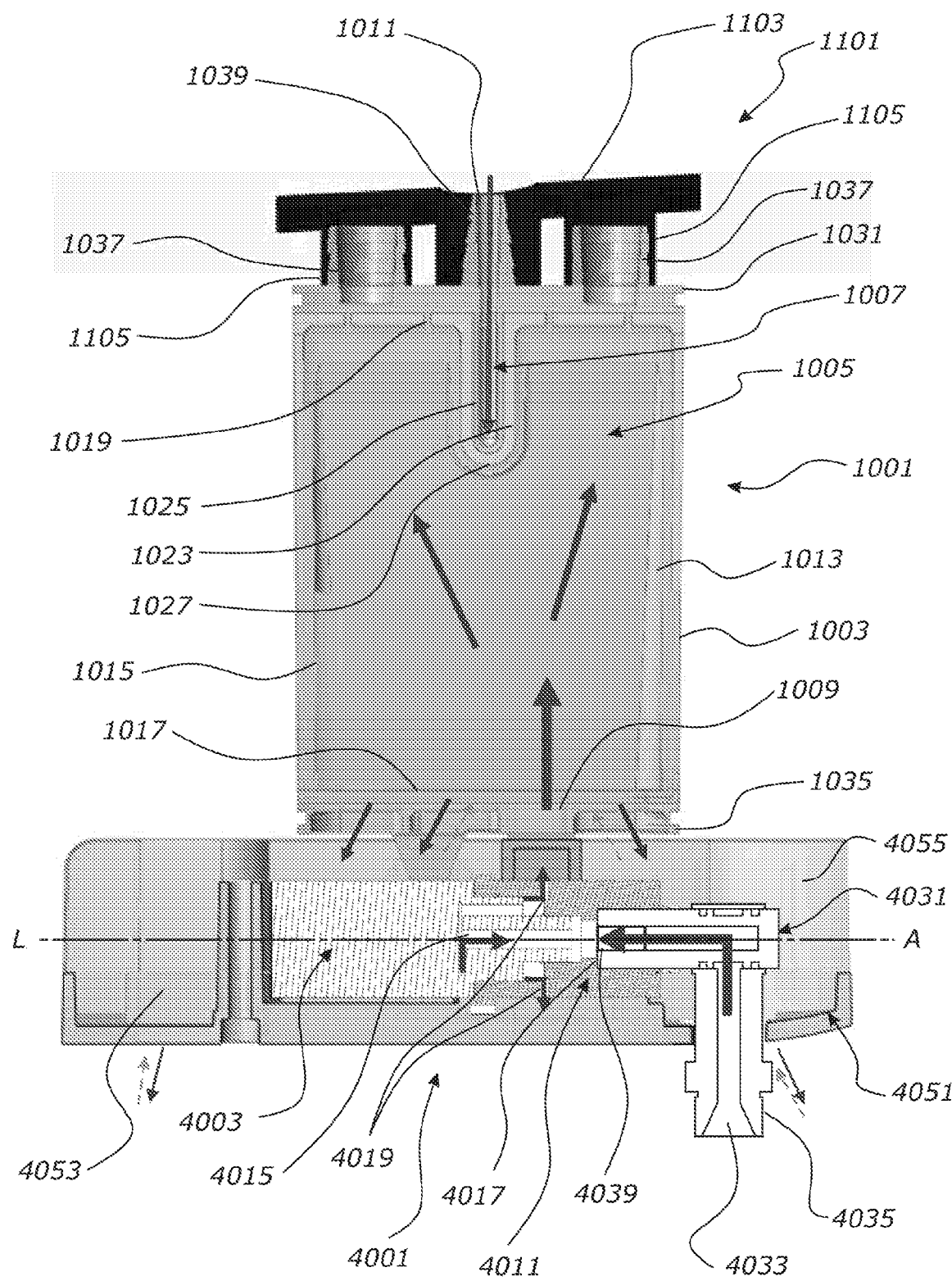
FIG. 24 is a sectional view showing the gas flow path through the filter module and the valve module.
Figure 25:
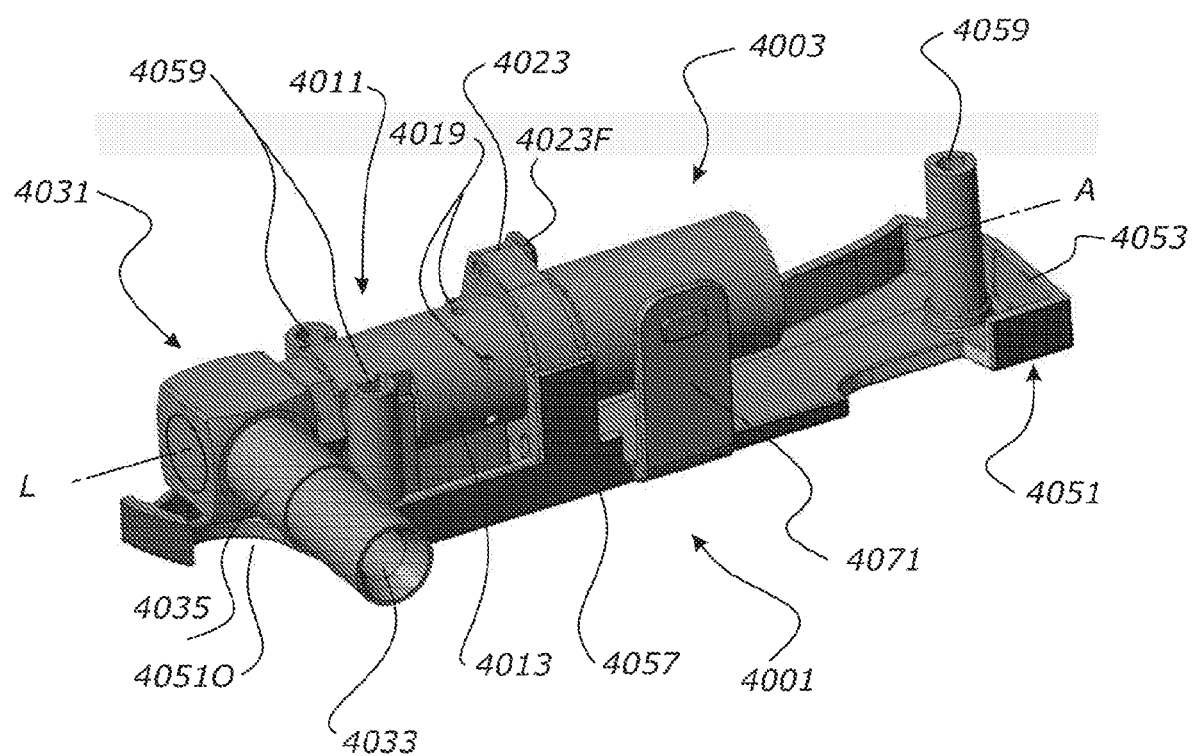
FIG. 25 is a rear side overhead perspective view of a first configuration valve module.
Figure 26:
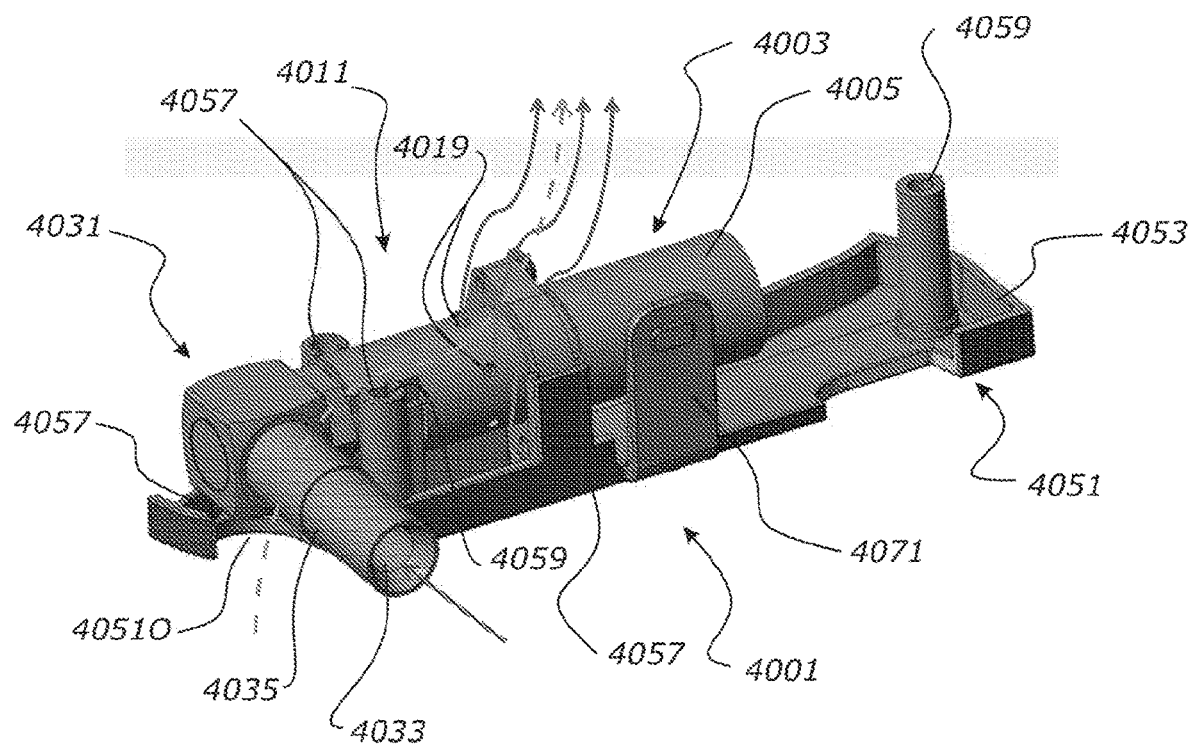
FIG. 26 is a rear side overhead perspective view showing the gas flow paths through the first configuration valve module, with the solid line arrows representing the flow of oxygen (or another gas), and the dashed line arrow representing the flow of ambient air.
Figure 27:
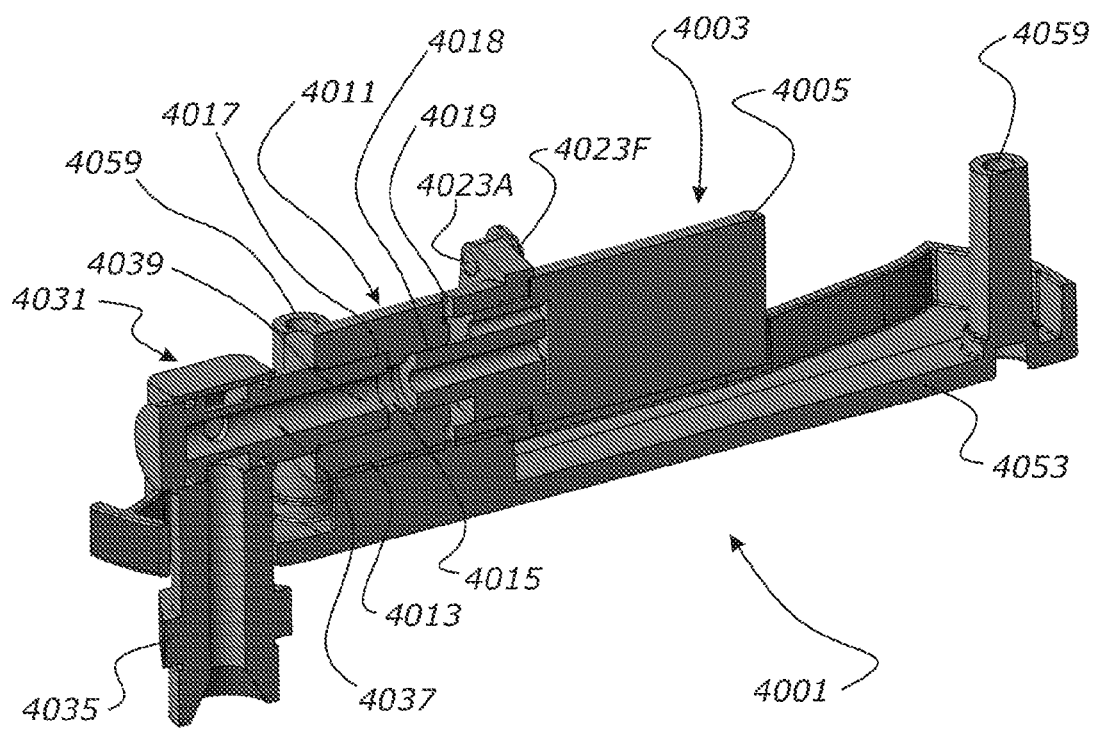
FIG. 27 is a sectional view through the first configuration valve module.
Figure 28:
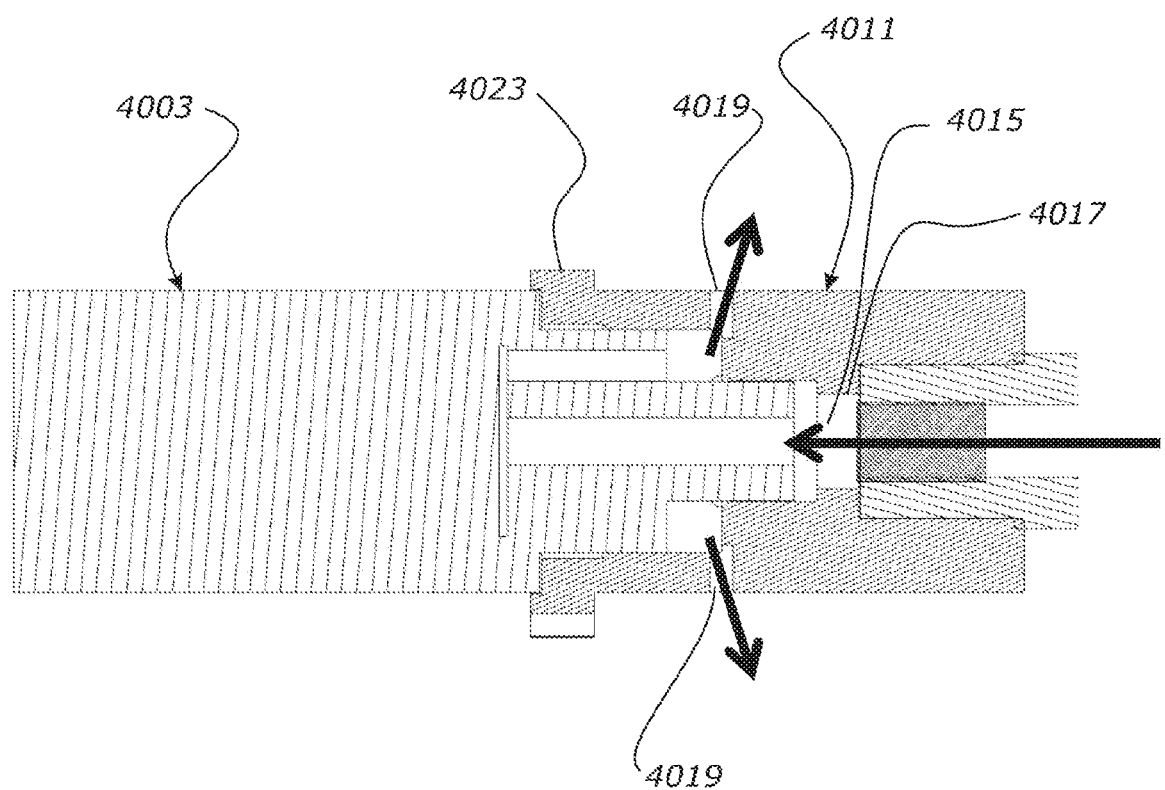
FIG. 28 is a sectional view showing the coupling of, and gas flow path through, the valve and valve manifold of the first configuration valve module.

As shown in FIGS. 18 and 19, the cover layer 440 comprises a sensing printed circuit board (PCB) 456. The cover layer 440 may also comprise one or more temperature sensors such as thermistors that sit in the elongate portion 428, 448 of the gas flow path. One sensor will measure gas temperature and the other can act as a redundant temperature sensor. Alternatively, one of the thermistors could be used as a reference flow sensor (e.g. via use as a constant-temperature thermistor), and the measured temperatures could be used to determine the gas flow rate through the portion 428, 448 of the gas flow path. The one or more temperature sensors may be located on a portion of the sensing PCB 456 that faces the gas flow. The sensing PCB 456 may additionally comprise other sensors including but not limited to pressure sensors, humidity sensors and dew point sensors.

One or both of the electronics boards 272 will be in electrical communication or coupled with the sensors to process information received from the sensors and operate the apparatus 10 based on the information received from the sensors.

In an alternative configuration, the motor/impeller unit may be provided remotely from the apparatus 10. In that configuration, the module received in the recess 250 may only comprise a gas flow path and various sensors, to deliver gases to the fixed elbow 324 and thereby to the liquid chamber 300. In an alternative configuration, the module received in the recess 250 may only comprise the motor and a gas flow path, but no sensors.

In another alternative configuration the motor and/or sensor module 400 may not be removable from the recess 250, but instead may be permanently mounted therein. The benefits of the gas isolation from the electrical/electronics components would still be provided in that configuration.

The flow path is compact, and has reduced turns/sharp turns which reduces flow separation and reduces resistance to flow.

The arrangement of the motor and flow path provides another layer of isolation because of the wall arrangement.

Having a modular motor and/or sensor module enables the various parts of the module to be taken apart if needed for cleaning and/or servicing.

There are advantageously no leak paths in the motor and/or sensor module. While the motor and/or sensor module may be a potential leak point, a leak in that region would result in the oxygen venting to atmosphere or into the liquid chamber.

Valve Module

FIGS. 20 to 28 show a first configuration of a valve module 4001. The valve module 4001 controls the flow of oxygen and/or other gases entering the gas flow path of the apparatus 10, and enables the apparatus 10 to regulate the proportion of oxygen entrained in the airflow. The valve module is formed as a modular unit for ease of manufacture, assembly, servicing, or replacement, for example in the event of malfunction, routine maintenance, or future upgrade/improvement.

The valve module 4001 inserts vertically in an upward direction into the valve module receptacle 306 in the lower chassis 202 of the main housing. In alternative configurations, the valve module may be insertable in a different direction into the housing, such as a forward direction, downward direction, rearward direction, or side direction. The valve module 4001 is removably engageable with the main housing of the apparatus, such that the valve module 4001 is substantially received in the housing and is accessible from the exterior of the housing. In some configurations, the valve module 4001 can be fixed within the main hosing and not removable. Part of the valve module 4001 is arranged to be substantially flush with an external wall of the housing when the valve module is removably engaged with the housing.

Because the valve module is modular and is accessible from the exterior of the housing, the valve module can be replaced without significant disassembly of the apparatus 10 and without compromising seals of the housing of the apparatus. Because the valve module 4001 is substantially received within the housing, when the valve module is engaged with the housing it becomes integrated with the housing and does not increase the size or bulk of the housing. Additionally, the components of the valve module such as the valve 4003 and valve manifold 4011 described below are protected in use because they are positioned within the valve carrier 4051 and main housing of the apparatus in use. This configuration significantly reduces the likelihood of damage of the valve module and valve module components if the apparatus 10 is inadvertently knocked or dropped.

The valve module comprises a flow control valve 4003 that is arranged to control a flow of gas through a valve manifold 4011. The valve is arranged to control a flow of gas into part of the apparatus. For example, the valve may be arranged to control a flow of gas to a filter module 1001. Alternatively, the valve 4003 may be arranged to control a flow of gas to another part of the apparatus. The valve module 4001 and filter module 1001 are positioned upstream of the blower 402 and motor and/or sensor module 400. In some embodiments, the valve module 4001 and filter module 1001 are positioned downstream of the blower 402.

The valve 4003 comprises a cylindrical body 4005 and a valve member in the body.

The flow control valve could be a solenoid valve, could be motor-driven, or could be piezo-operated for example.

In a solenoid valve, the valve member is actuated between open and closed positions. The solenoid valve may be a proportional valve. The extent of gas flow through the valve (i.e. due to the size of the valve opening) is relative to the electrical current supplied to the valve.

Alternatively, the solenoid valve may be controlled with a modulated input signal, so that the valve is modulated between open and closed positions.

The valve 4003 could be a needle valve, plunger valve, gate valve, ball valve, butterfly valve, globe valve, etc. The valve may be of the pressure compensated type.

In some configurations, the valve is a normally-closed valve; that is, the valve is closed when powered off. That will prevent a connected gas supply line continuously releasing oxygen or other gas when the apparatus is powered off. In some alternative configurations, the valve is a normally-open valve.

In some configurations, the valve 4003 is an electrically actuated proportional solenoid valve. For example, the valve may be a µProp valve available from Staiger GmbH & Co. KG of Erligheim, Germany, may be an Asco 202 series Preciflow valve available from Emerson/Asco Valves of New Jersey, or may be any other suitable type of valve.

The valve may have a coaxial inlet-outlet configuration.

The valve module 4001 comprises a valve manifold 4011 which has a body 4013 defining a gas flow path 4015 between a valve manifold gases inlet 4017 and one or more valve manifold gases outlets 4019. The gases inlet 4017 of the valve manifold is axially located at or toward an end of the valve manifold. In some configurations the valve manifold 4011 has a single gases outlet 4019, which is radially located on the valve manifold. In some configurations, the valve manifold 4011 comprises a plurality of valve manifold gases outlets 4019 that are radially located about the valve manifold. The valve manifold outlets 4019 are arranged to deliver gases from the valve manifold gases inlet 4017 to a gases inlet of the filter module 1001. The radial location of outlet(s) 4019 assists with directing oxygen (or other gas) towards the filter module, minimizing loss of oxygen and enhancing entrainment efficiency. The valve 4003 is arranged to control a flow of gas from the valve manifold gases inlet 4017 to the valve manifold gases outlet(s) 4019. When the valve is 'closed', gas flow from the gases inlet 4017 to the gases outlet(s) 4019 is prevented. When the valve is 'open', gas flow from the gases inlet 4017 to the gases outlet(s) 4019 is enabled.

An end 4018 of the valve manifold 4011 opposite to the gases inlet receives and sealingly engages with the valve 4003 such that the valve and valve manifold are in fluid communication. The end 4018 comprises a flange 4023 to mount to the valve. The flange 4023 has apertures 4023A to receive fasteners 4023F to fasten the manifold to the valve 4003. O-ring(s) may be provided about the periphery of the interface between the valve 4003 and the valve manifold 4011 to sealingly engage the valve with the valve manifold.

The valve manifold 4011 directs/disperses oxygen from the valve via radially located gases outlets 4019. In some embodiments, a single gases outlet 4019 is provided in the valve manifold. As oxygen passes through the outlet(s), noise is generated. Because the apparatus may be used in medical and/or home environments in close proximity to the patient, it is desirable to minimize the noise produced.

Additionally, or alternatively, a hood, duct, or channel may be formed around, in proximity to, or in fluid communication with the valve manifold outlet(s) 4019 in order to reduce noise. Additionally and/or alternatively, foam, or the like, may be placed around the valve manifold, in proximity to the valve manifold outlets, to reduce noise.

A small filter may be provided inside the valve manifold gases inlet 4017 inlet to prevent the introduction of dust or particulates into the valve.

An end of the valve manifold corresponding to the gases inlet 4015 is arranged to receive and connect to a connector 4031. In the form shown, the connector 4031 is a swivel connector. Alternatively, the connector 4031 may be arranged such that a gases inlet 4033 of the connector can move in a different way, such as a translational movement or pivoting movement for example.

The valve module 4001 is located at the start of the flow path of the apparatus. If the valve 4003 was to be obstructed (i.e. by dust, particulate, etc.) such that it would be held open, excess pressurized oxygen or other gas would 'dump' out ambient air entry opening(s) in the valve carrier 4051 (e.g. the opening shown beneath the swivel connector in FIG. 26). This would prevent any excess pressure reaching the patient. As such, the system may be considered inherently pressure limited without the use of a pressure relief valve.

Opening(s) 40510 are provided in the valve carrier 4051 to allow ambient air to be drawn in to the gas flow path of the apparatus. The ambient air flow path passes near or adjacent to the valve. In the form shown, the opening 40510 is located around the gases inlet of the swivel connector. Additionally, or alternatively, the opening may be located elsewhere in the valve carrier. When the blower motor 402 of the apparatus is operated, that will create suction through the filter module and valve module, to suck ambient air into the apparatus. The ambient air flow path passes through the valve module and allows ambient air to be entrained with the flow of gas from the flow control valve. The ambient air flow path has a gas outlet adapted to deliver ambient air such that it flows past one or more temperature sensors of the apparatus for delivering a flow of gas.

The apparatus may simultaneously draw in gas from the gases inlet of the valve manifold and ambient air, or the pressurization of gas from the gases inlet may force that gas through the filter. The gases will exit the valve module and enter the gases inlets in the filter. The apparatus may be configured such that the gas from the gases inlet and the ambient air are dynamically entrained/mixed in the apparatus prior to being delivered to the gases outlet of the apparatus.

The valve module may be configured to minimize pressure drop across the valve module by having one or more of: the large opening 40510 for ambient air located around the swivel connector and/or elsewhere; radiuses/rounded/sloped edges in the flow path (i.e. inside the valve manifold, for example) to minimize turbulence and smooth flow.

This valve module 4001 described herein are arranged to directly couple with the filter 1001 to provide a gas flow path from the valve module to the filter. A hose connection is not required between the valve module and the filter module. This minimizes the size of the components and makes it easy to connect and disconnect the modular valve module and filter module.

The filter modules and valve modules described herein may provide varying gas flow paths for the apparatus. For example, the valve module may control the flow of oxygen entering the gas flow path of the apparatus, via the valve module and filter module. Alternatively, the valve module may be bypassed by means of direct connection of an alternative oxygen source to the filter module by the first sub-compartment gases inlet (inlet 1011 of FIG. 24 for example). This may be practical in circumstances where a user may wish to manually adjust the oxygen supply (i.e. such as by the wall supply rotameter).

It will be appreciated that the filter modules and the valve modules described herein may be used separately in apparatuses for delivering a flow of gas. Alternatively, the filter and the valve module may be used together as a filer and valve assembly for improved functionality.

In the configurations shown, the apparatus 10 receives oxygen by at least one of the following: via the valve module (for automatic oxygen regulation by the apparatus), or via the alternative gases inlet provided on the top of the filter (allowing attachment of a manually adjustable oxygen supply—i.e. such as by the wall supply rotameter).

The various configurations described are exemplary configurations only. Any one or more features from any of the configurations may be used in combination with any one or more features from any of the other configurations.

For example, the swivel connector used in the valve module may have additional functionality. In some configurations, the swivel connector may be arranged to swivel about more than one axis; and may for example have two adjacent swivel connection portions with swivel axes that are transverse to each other, so that the gases inlet of the swivel connector can rotate around the two axes. In some configurations, the swivel connector may comprise a ball and socket arrangement or similar, to enable the gases inlet of the swivel connector to rotate in substantially any direction. In some configurations, the swivel connector may be arranged to provide both swiveling and translational movement; so that the gases inlet of the swivel connector may both swivel about one or more axes and may also travel linearly for example. This may be practical for translating the gases inlet from one portion of the apparatus to another, such as from one side of the apparatus to the other of the apparatus for example. In some configurations, the gases inlet may be arranged to translate instead of rotate.

As another example, while the motor and/or sensor sub-assembly recess is described as being in the underside of the main housing, it could alternatively be in a rear, side, front, or top of the housing. With such a variant, the air and/or oxygen inlets may also be positioned differently as required.

As another example, rather than the liquid chamber and chamber bay being configured so that the liquid chamber is inserted into and removed from the chamber bay from a front of the housing, the configuration could be such that the liquid chamber is inserted into and removed from the chamber bay from a side, rear, or top of the housing.

As another example, while the filter modules are described as being inserted into the housing from above and the valve modules inserted into the housing from below, either or both of those components could be inserted into any suitable part of the housing, such as an upper part, lower part, side part, front part, or rear part.

The filter module and valve module are described with reference to a flow therapy apparatus that is capable of delivering heated and humidified gases to a patient or user. The apparatus may be suitable for treating chronic obstructive pulmonary disease (COPD). The apparatus may be configured to deliver gases to a patient interface at a high flow rate (high flow therapy), particularly nasal high flow therapy.

Alternatively, the filter module and/or valve module may be used in an apparatus for a different purpose. The apparatus may be a high flow therapy apparatus, or may be a low flow therapy apparatus. The features may also be provided in an apparatus for providing continuous positive airway pressure (CPAP), which may deliver gases (humidified or otherwise) at positive pressure.

The filter module and/or valve module may alternatively be used with an apparatus that does not require a humidifier and therefore does not require the liquid chamber 300 or chamber bay 108 features. For example, it will be appreciated that the configuration that isolates the motor and gas flow path from the electrical and electronic components has broad applications in other types of gas delivery apparatuses.

The 'flow therapy apparatus' language is intended to cover all such variants.

Reference to any prior art in this specification is not, and should not be taken as, an acknowledgement or any form of suggestion that the prior art forms part of the common general knowledge in the field of endeavour in any country in the world.

Where reference is used herein to directional terms such as 'up', 'down', 'forward', 'rearward', 'horizontal', 'vertical' etc., those terms refer to when the apparatus is in a typical in-use position, and are used to show and/or describe relative directions or orientations.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The terms "approximately," "about," and "substantially" as used herein represent an amount close to the stated amount that still performs a desired function or achieves a desired result. For example, in some embodiments, as the context may permit, the terms "approximately", "about", and "substantially" may refer to an amount that is within less than or equal to 10% of, within less than or equal to 5% of, and within less than or equal to 1% of the stated amount.

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (for example, not all described acts or events are necessary for the practice of the algorithms) Moreover, in certain embodiments, acts or events can be performed concurrently, for example, through multi-threaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. A respiratory apparatus that provides a flow of gases to a patient, wherein the respiratory apparatus is configured to deliver high flow therapy to the patient, the respiratory apparatus comprising:
    a gases composition sensor configured to determine at least a measured fraction of delivered oxygen content (FdO2) of gases flow during operation of the respiratory apparatus, wherein the gases composition sensor is an ultrasonic sensor system;
    a controller configured to control delivery of gases to the patient using closed loop control, wherein the controller is configured to:
        receive patient parameter data indicative of oxygen saturation (SpO2) of the patient from at least one sensor;
        execute a control phase, wherein operation of the respiratory apparatus during a therapy session is based at least in part on the patient parameter data, wherein the control phase includes determining a target FdO2, wherein the target FdO2 is determined based at least in part on a target SpO2, measured SpO2, measured FdO2, and a previous target FdO2.

2. The respiratory apparatus of claim 1 wherein the respiratory apparatus is configured to deliver a nasal high flow (NHF) flow of gases to the patient.

3. The respiratory apparatus of claim 1, wherein the controller is configured to receive device parameter data indicative of an oxygen concentration of the gases flow.

4. The respiratory apparatus of claim 1 further comprising a supplementary gas inlet valve, wherein the controller is configured to control operation of the supplementary gas inlet valve.

5. The respiratory apparatus of claim 4 further comprising an ambient air inlet, wherein the supplementary gas inlet valve is an oxygen inlet valve, wherein the oxygen inlet valve is in fluid communication with a filter module, wherein the respiratory apparatus is configured to entrain oxygen received from the oxygen inlet valve with ambient air from the ambient air inlet in the filter module.

6. The respiratory apparatus of claim 5, wherein the gases composition sensor is positioned downstream of a blower module of the respiratory apparatus, and wherein the filter module is positioned upstream of the blower module of the respiratory apparatus.

7. The respiratory apparatus of claim 1, wherein the gases composition sensor is positioned downstream of a blower module of the respiratory apparatus.

8. The respiratory apparatus of claim 1, wherein the closed loop control includes using a second closed loop control model configured to determine a control signal for an oxygen inlet valve based at least in part on a difference between the target FdO2 and a measured FdO2.

9. The respiratory apparatus of claim 8, wherein the control signal for the oxygen inlet valve is determined further based at least in part on a gases flow rate, wherein the gases flow rate is a total gases flow rate.

10. The respiratory apparatus of claim 1, wherein the controller is configured to transfer to a manual mode of operation when a signal quality of the at least one sensor is below a threshold.

11. The respiratory apparatus of claim 1, wherein the controller is configured to transfer to a manual mode of operation when the patient SpO2 is outside of defined limits.

12. The respiratory apparatus of claim 11, wherein the controller is configured to trigger an alarm when the patient SpO2 is outside of the defined limits.

13. The respiratory apparatus of claim 1 wherein the ultrasonic sensor system comprises a first ultrasonic transducer and a second ultrasonic transducer.

14. The respiratory apparatus of claim 13 wherein each of the first ultrasonic transducer and the second ultrasonic transducer is a receiver and a transmitter.

15. The respiratory apparatus of claim 14 wherein the first ultrasonic transducer and the second ultrasonic transducer send pulses bidirectionally.

16. The respiratory apparatus of claim 13 wherein at least one of the first ultrasonic transducer or the second ultrasonic transducer send pulses along the gases flow.

17. The respiratory apparatus of claim 13 wherein at least one of the first ultrasonic transducer or the second ultrasonic transducer send pulses across the gases flow.

* * * * *